(12) United States Patent
Bannister et al.

(10) Patent No.: US 10,328,078 B2
(45) Date of Patent: Jun. 25, 2019

(54) PTERIDINE DIONE MONOCARBOXYLATE TRANSPORTER INHIBITORS

(71) Applicant: THE SCRIPPS RESEARCH INSTITUTE, La Jolla, CA (US)

(72) Inventors: Thomas D. Bannister, Palm Beach Gardens, FL (US); Hui Wang, Jupiter, FL (US); Chao Wang, Palm Beach Gardens, FL (US); John L. Cleveland, Land O' Lakes, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/545,152

(22) PCT Filed: Jan. 22, 2016

(86) PCT No.: PCT/US2016/014458
§ 371 (c)(1),
(2) Date: Jul. 20, 2017

(87) PCT Pub. No.: WO2016/118823
PCT Pub. Date: Jul. 28, 2016

(65) Prior Publication Data
US 2018/0008605 A1     Jan. 11, 2018

Related U.S. Application Data

(60) Provisional application No. 62/106,472, filed on Jan. 22, 2015.

(51) Int. Cl.
| | | |
|---|---|---|
| *C07D 487/04* | (2006.01) | |
| *A61K 31/519* | (2006.01) | |
| *A61K 45/06* | (2006.01) | |
| *A61K 31/155* | (2006.01) | |
| *A61K 31/525* | (2006.01) | |
| *A61K 31/4985* | (2006.01) | |
| *C07D 475/02* | (2006.01) | |
| *C07D 475/00* | (2006.01) | |
| *A61P 37/06* | (2006.01) | |

(52) U.S. Cl.
CPC .......... *A61K 31/519* (2013.01); *A61K 31/155* (2013.01); *A61K 31/4985* (2013.01); *A61K 31/525* (2013.01); *A61K 45/06* (2013.01); *A61P 37/06* (2018.01); *C07D 475/00* (2013.01); *C07D 475/02* (2013.01); *A61K 2300/00* (2013.01)

(58) Field of Classification Search
CPC .. C07D 487/04; C07D 471/04; C07D 495/04; C07D 475/00; C07D 475/02; A61K 31/535; A61K 31/155; A61K 31/4985; A61K 31/519; A61K 31/525; A61K 47/06
USPC ....................................... 544/257; 514/262.1
See application file for complete search history.

(56) References Cited

PUBLICATIONS

Wang et al., Synthesis and Structure—Activity Relationships of Pteridine Dione and Trione Monocarboxylate Transporter 1 Inhibitors , Journal of Medicinal Chemistry, vol. 57, pp. 7317-7324 (2014).*

Gurrapu et al., Monocarboxylate Transporter 1 Inhibitors as Potential Anticancer Agents, ACS Medicinal Chemistry Letters, 6, pp. 558-561 (2015).*

Simone, Oncology: Introduction, Cecil Textbook of Medicine, 20th Edition, vol. 1, pp. 1004-1010, 1996.*

Gura, Systems for identifying New Drugs Are Often Faulty, Cancer Models, Science, vol. 278, No. 5340, pp. 1041-1042, Nov. 1997.*

Johnson et al., Relationships between drug activity in NCI preclinical in vitro and in vivo models and early clinical trials, British Journal of Cancer (2001) 64(10): 1424-1431.*

Pearce et al., Failure modes in anticancer drug discovery and development, Cancer Drug Design and Discovery Edited by Stephen Neidle, Chapter 18, pp. 424-435 (2008).*

* cited by examiner

*Primary Examiner* — Deepak R Rao
(74) *Attorney, Agent, or Firm* — Geoffrey K. Cooper; Thomas Fitting

(57) ABSTRACT

The invention provides compounds effective as inhibitors of monocarboxylate transporters such as MCT1 and MCT4, which can be used for treatment of medical conditions wherein treatment of the condition with a compound having an inhibitor effect on MCT1, MCT4, or both is medically indicated. Compounds of the invention can have antitumor, antidiabetes, anti-inflammatory, or immunosuppressive pharmacological effects, and can be effective for treatment of cancer and of type II diabetes.

7 Claims, 3 Drawing Sheets

SR 11431
(the product of Example 3)

PTERIDINE DIONE MONOCARBOXYLATE TRANSPORTER INHIBITORS

CROSS-REFERENCE TO RELATED APPLICATION

This application claims the priority of U.S. Provisional Application Ser. No. 62/106,472, filed Jan. 22, 2015, the disclosure of which is incorporated herein by reference in its entirety.

STATEMENT OF GOVERNMENT SUPPORT

This invention was made with government support under R01 CA154739 awarded by the National Institutes of Health. The government has certain rights in the invention.

BACKGROUND

In the 1920s the German biochemist Otto Warburg described metabolic differences between cancerous and normal cells, where he noted that tumor cells rely upon a high rate of aerobic glycolysis rather than oxidative phosphorylation to produce energy for maintenance of cellular functions.[1,2] Indeed, cancer cells have up to a 60-fold enhanced rate of glycolysis relative to normal cells, even with sufficient oxygen.[1] This dependence upon glycolysis, and its consequences, is termed "the Warburg effect".[2]

Malignant cells are highly anabolic and require very high levels nutrients, ATP and building blocks to synthesize components needed for their growth and survival. Use of the glycolytic pathway provides ATP but also drives production of lactate, which is produced from pyruvate at the end of the glycolytic pathway. Massive lactate production by the tumor cell requires an efficient means for its consumption or elimination, to prevent intracellular acidification of the cancer cell.

Two mechanisms for handling excess lactate have been described. First, in some rare tumor types lactate is converted to pyruvate for entry into the TCA cycle. More commonly, however, lactate homeostasis is maintained via a family of twelve-membrane pass cell surface proteins known as the monocarboxylate transporters (MCTs; also known as the SLC16a transporter family). Fourteen MCTs are known, but only MCT1, MCT2, MCT3 and MCT4 transport small monocarboxylates such as lactate, pyruvate and ketone bodies (acetoacetate and β-hydroxybutyrate) across plasma membranes in a proton-linked exchange.[3] Expression analyses have established that most aggressive tumor types express markedly elevated levels of MCT1, MCT4 or both.[4] The chaperone protein CD147, which contains immunoglobulin-like domains, is required for MCT1 and MCT4 cell surface expression and is co-localized with the transporters. MCT1, MCT4 and CD147 are now high priority targets for cancer therapeutics.[4]

The expression of MCT1 and MCT4 is regulated by two major oncogenic transcription factors, MYC and hypoxia inducible factor-1α (HIF-1α), respectively,[4,5] that direct marked increases in the production of key proteins that support aerobic glycolysis, including amino acid transporters and enzymes involved in the catabolism of glutamine and glucose.[6] Malignancies having MYC involvement and hypoxic tumors are generally resistant to current frontline therapies, with high rates of treatment failure, relapse and high patient mortality.[7,8] Importantly, inhibition of MCT1 or MCT4 can kill tumor cells ex vivo and provoke tumor regression in vivo,[4,9] and their potency is augmented by agents such as metformin that force a glycolytic phenotype upon the cancer cell.[4]

Many weak MCT inhibitors (i.e., those effective at high micromolar levels) have been described, including α-cyano-4-hydroxycinnamate[10,11] stilbene disulfonates,[12] phloretin[13] and related flavonoids.[14] Coumarin-derived covalent MCT inhibitors have also recently been disclosed,[15,16] as have pteridinones.[17]

The most advanced MCT1 inhibitors are related pyrrolopyrimidine diones, pyrrolopyridazinones, and thienopyrimidine diones,[18,23] including a compound that has advanced into clinical trials for treating some human malignancies.[24,25] These compounds, and to our knowledge all MCT1 inhibitors yet described, are dual MCT1/MCT2 inhibitors. MCT2 has very high sequence homology with MCT1, yet it likely has a lesser role than MCT1 and MCT4 for monocarboxylate transport in human cancers based upon expression studies. However, MCT2 inhibition may play a role in potential off-target effects of current agents that could arise from blocking lactate transport in normal cells.

The first highly potent MCT inhibitor was initially identified via a cell-based assay seeking immunosuppressive agents that inhibit NFAT1-directed IL-2 transcription.[26] MCT1 inhibition as its mechanism of action was described a full decade later.[18] Several subsequently published analogs are also potent MCT1 inhibitors, with low nanomolar Ki values for MCT1 inhibition and low nanomolar $EC_{50}$ values inn MTT assays for growth of MCT1-expressing tumors.

In many human tumors MCT1 and MCT4 are inversely expressed. Small molecule MCT1 inhibitors are now known to disable tumor cell metabolism, proliferation and survival, and impair tumorigenic potential in vivo in tumors expressing high levels of MCT1.[4] MCT4 inhibitors are likely to be similarly effective for tumors expressing elevated levels of MCT4. Antitumor effects of MCT1 inhibitors are augmented by co-administration of the biguanide metformin, which is thought to further augment reliance by tumor cells upon aerobic glycolysis and thus increase the demand to MCT1-mediated efflux of lactate.[4]

In addition to antitumor effects, inhibitors of MCT1 and/or MCT4 may have other important biological effects, such as immune suppression,[18] anti-inflammatory,[26] and anti-diabetic effects.[27-32] MCT1 is normally expressed at very low levels in pancreatic islets and in beta-cells in particular.[27-28] This scenario explains the very slow uptake of lactate in these cells.[29] A hallmark of exercise-induced hyperinsulinism (EIHI) is inappropriate insulin secretion following vigorous physical activity, which leads to hypoglycemia.[30] In a 2012 study, Rutter and co-workers established that EIHI is associated with elevated expression of MCT1 in beta-cells and that transgenic mice engineered to overexpress MCT1 in part displayed many of the hallmarks of EIH16.[31] While the link between lactate and insulin secretion has been suggested since the late 1980s[32] these more recent studies clarify the central role of MCT1 (and perhaps of the related lactate transporters MCT2 and MCT4).

SUMMARY

The invention provides, in various embodiments, a MCT-inhibitory compound of formula A or of formula B

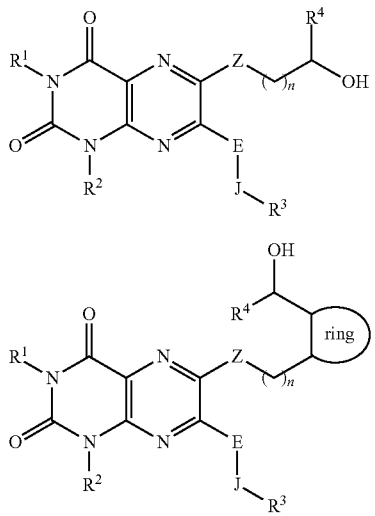

wherein

R¹ and R² are each independently selected from the group consisting of hydrogen, $(C_1-C_6)$alkyl, $(C_3-C_6)$branched alkyl, $(C_3-C_7)$cycloalkyl, $(C_1-C_6)$fluoroalkyl, a $(C_6-C_{10})$aryl ring system, a 5- to 9-membered heteroaryl ring system, a $(C_1-C_6)$alkyl-$(C_6-C_{10})$aryl ring system, and a $(C_1-C_6)$alkyl-(5- to 9-membered)heteroaryl ring system;

provided that when R² comprises an aryl or heteroaryl ring system, the ring system bears 0-2 independently selected substituents from the group consisting of fluoro, chloro, trifluoromethyl, $(C_1-C_6)$alkoxy, and $(C_1-C_6)$fluoroalkoxy;

E is $CH_2$, $CH(C_1-C_6)$alkyl, or $CH(C_3-C_7)$cycloalkyl;

J is O, S, S(O), S(O)$_2$, NH, N$(C_1-C_6)$alkyl, or NC(=O)$(C_1-C_6)$alkyl;

R³ is a monocyclic or bicyclic $(C_6-C_{10})$aryl or a monocyclic or bicyclic (5- to 10-membered) heteroaryl group wherein the aryl or heteroaryl can be substituted or unsubstituted;

R⁴ is hydrogen, $(C_1-C_6)$alkyl, $(C_3-C_6)$branched alkyl, $(C_1-C_6)$fluoroalkyl, $(C_3-C_7)$cycloalkyl, a (4- to 7-membered)heteroaryl, or a monocyclic or bicyclic $(C_6-C_{10})$aryl or a monocyclic or bicyclic (5- to 10-membered) heteroaryl group wherein the aryl or heteroaryl can be substituted or unsubstituted;

Z is a bond, or is —O—, —CH$_2$—, —CH(Me)-, —S—, —NH—, or —N(C1-C6)alkyl;

n=1, 2, 3, or 4;

the cyclic group indicated as "ring" is an aryl or heteroaryl group of any one of the following formulas:

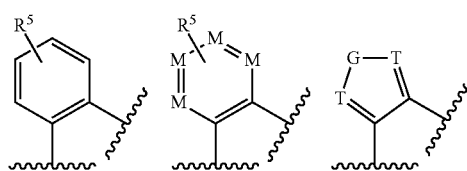

wherein wavy lines indicate points of bonding, and wherein each M is an independently selected CH or N, provided that M group is a nitrogen atom in one or two instances;

G is S, O, NH, NMe, or NCF$_3$;

T is independently at each occurrence CH or N;

wherein R⁵ is optionally present, R⁵ being one to four instances of independently selected F, Cl, Br, CF$_3$, $(C_1-C_6)$alkyl, OCF$_3$, O$(C_1-C_6)$alkyl, or CO—$(C_1-C_6)$alkyl;

or, the cyclic group indicated as "ring" is a $(C_3-C_7)$cycloalkyl or a saturated (3- to 7-membered)heterocyclyl comprising 1-2 heteroatoms selected from the group consisting of O, NH, N(C1-C6)alkyl, and N(C1-C6)fluoroalkyl; wherein the points of bonding may be cis or trans;

or a pharmaceutically acceptable salt thereof.

The invention further provides a pharmaceutical composition comprising a compound of the invention and a pharmaceutically acceptable excipient.

In various embodiments, the invention provides a method of inhibiting monocarboxylate transporter MCT1, monocarboxylate transporter MCT4, or both, comprising contacting the monocarboxylate transporter with an effective amount or concentration of a compound of the invention.

The invention further provides a method of treatment of a condition in a mammal wherein treatment of the condition with a compound having an inhibitor effect on MCT1, MCT4, or both is medically indicated, comprising administering an effective amount of a compound of the invention. For example, the compound can show an antitumor, antidiabetes, anti-inflammatory, or immunosuppressive pharmacological effect.

DETAILED DESCRIPTION

Definitions

Figure 1:
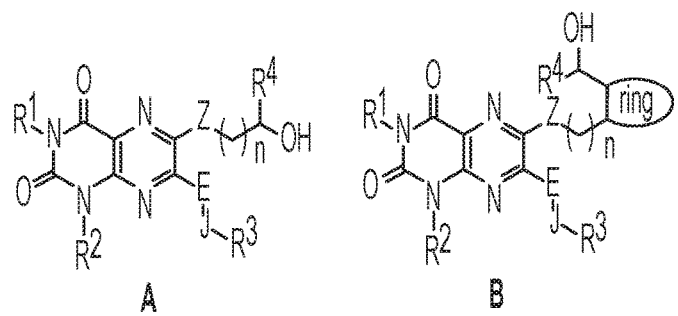
FIG. 1 shows pteridine dione inhibitors of MCT of structures A and B.
Figure 2:
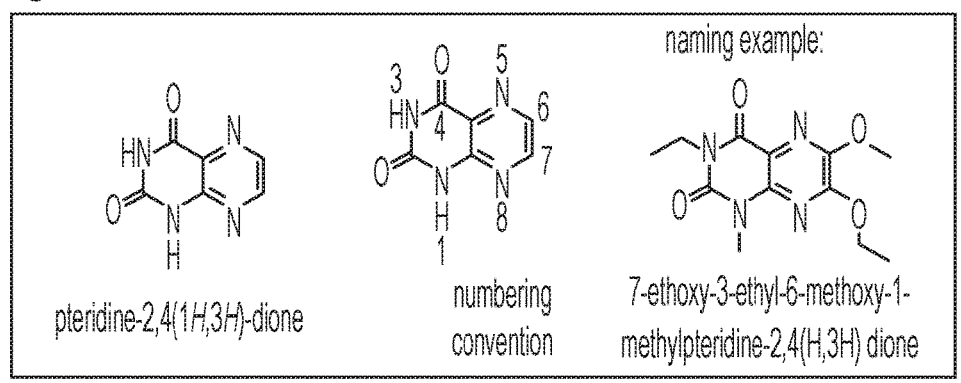
FIG. 2 shows the general scaffold type, termed a "pteridine dione", with the numbering conventions for this ring system and a naming example to illustrate the numbering conventions.

The terms MCT1 and MCT4 refer to monocarboxylate transporter isoform 1 and monocarboxylate transporter isoform 4, respectively.

The term "inhibitor" as used herein refers to a compound that binds to a target and renders it biologically inactive or less active.

The term "heteroatom" as used herein refers to an atom of any element other than carbon or hydrogen. Common heteroatoms include nitrogen, oxygen, phosphorus, sulfur and selenium.

The abbreviation "CNS" as used herein refers to the central nervous system of an organism.

The term "$EC_{50}$" as used herein refers to the dose of a test compound which produces 50% of its maximum response or effect in an assay.

The term "$IC_{50}$" as used herein refers to the dose of a test compound which produces 50% inhibition in a biochemical assay.

The term "alkyl" as used herein throughout the specification, examples, and claims refers to a hydrocarbon group, and includes branched chain variations, or "branched alkyl" groups.

The term "fluoroalkyl" refers to an alkyl group having any chemically possible number of fluorine atoms bonded thereto; thus, the term encompasses mono-, di-, and trifluoromethyl, perfluoroalkyl groups, and the like.

The term "fluoroalkoxy" refers to an alkoxy group having any chemically possible number of fluorine atoms bonded thereto; thus, the term encompasses mono-, di-, and trifluoromethoxy, perfluoroalkoxy groups, and the like.

The term "cycloalkyl" as used herein throughout the specification, examples, and claims refers to a cyclic hydrocarbon group, and may include alkyl substituents on the cyclic hydrocarbon group.

The term "substituted alkyl" as used herein refers to alkyl moieties having substituents replacing a hydrogen atom on one or more carbon atoms of the hydrocarbon backbone. Such substituents can include, for example, a halogen, a halogenated alkyl (e.g., $CF_3$), a hydroxyl, a carbonyl, an amino, an amido, an amidine, an imine, an alkoxy, a halogenated alkoxy (e.g., $OCF_3$, $OCHF_2$, etc.) a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic group. It will be understood by those skilled in the art that the moieties substituted on the hydrocarbon chain can themselves be substituted, if appropriate.

The term "aryl" and "heteroaryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls. The terms ortho, meta and para apply to 1,2-, 1,3- and 1,4-disubstituted benzenes, respectively. For example, the names "1,2-dimethylbenzene" and "ortho, meta-dimethylbenzene" are synonymous.

The term "aralkyl" as used herein refers to an alkyl group substituted with an aryl group (e.g., an aromatic or heteroaromatic group). Examples include $CH_2Ph$, $CH_2CH_2Ph$, $CH_2CH_2$-indole, and the like. The aromatic ring can be substituted at one or more ring positions with such substituents, as described above.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "heterocyclyl" or "heterocyclic group" as used herein refer to 3- to 10-membered ring structures, more preferably 3- to 7-membered rings that include one to four heteroatoms. Heterocycles can also be polycycles. Heterocyclyl groups include, for example, azetidine, azepine, thiophene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "halogen" designates —F, —Cl, —Br or —I.

As used herein, the term "hydroxyl" means —OH.

As used herein, the term "sulfonyl" means —$SO_2$—.

The terms "amine" and "amino" as used herein are recognized in the art and refer to both unsubstituted and substituted amines, e.g., a moiety that can be represented by the general formulas —$NH_2$, —NHR, —NRR", where R and R' are alkyl, cycloalkyl, aryl, or heterocyclyl groups, as example.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like.

The term "ether" as used herein refers to two hydrocarbons groups covalently linked by an oxygen atom.

The term "sulfonamido" is art recognized and includes a moiety that can be represented by the general formula —$SO_2$—N(R)(R') wherein where R, and R' are alkyl, cycloalkyl, aryl, or heterocyclyl groups, as examples.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The phrase "protecting group" as used herein means temporary substituents which protect a potentially reactive functional group from undesired chemical transformations. Examples of such protecting groups include carbamates of amines, esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

The term "Example" as used herein indicates the procedures followed for the preparation of a claimed compound, In general, the compounds of the present invention may be prepared by the methods illustrated in the general reaction schemes as, for example, described in the examples, or by modifications thereof, using readily available starting materials, reagents and conventional synthesis procedures not mentioned here.

It is understood that certain claimed molecules may stably exist in with isotopic variants among specific substituents, such as deuterium or tritium in the place of hydrogen. Such isotopic variants also fall within the scope of the invention.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

It is understood that certain groups such as amines bear a net charge. When such a group or groups are present in a "claimed compound", pharmaceutically acceptable salt forms of the structure are implicitly encompassed in the claims as well. For example, a claim for a compound with one or more amino groups present in the structure also implicitly claims all pharmaceutically acceptable salt forms, such as hydrochloride, methanesulfonyl, formate, oxalate, tartrate salts, and the like.

It is understood that certain "claimed compounds" may stably exist as hydrates or solvates. Such differing forms are also implicitly encompassed in the claims. Hydrates refer to molecules of water present in the crystal lattice. Solvates refer to molecules of a relatively benign solvent, such as ethanol, present in the crystal lattice.

It is understood that certain "claimed compounds" in any form, including as a salt, hydrate, or solvate, may stably exist in multiple solid crystalline and/or amorphous forms. Such forms may confer different physical properties (e.g., rate of dissolution, stability, hydroscopicity). Such differing solid forms are also implicitly encompassed in the claims.

The invention provides, in various embodiments, a MCT-inhibitory compound of formula A or of formula R

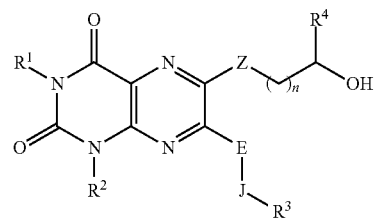

A

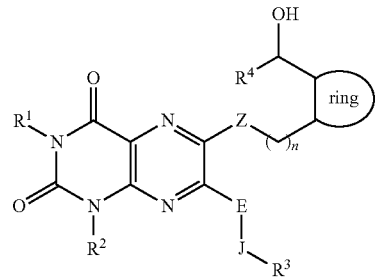

B wherein $R^1$ and $R^2$ are each independently selected from the group consisting of hydrogen, $(C_1-C_6)$alkyl, $(C_3-C_6)$branched alkyl, $(C_3-C_7)$cycloalkyl, $(C_1-C_6)$fluoroalkyl, a $(C_6-C_{10})$aryl ring system, a 5- to 9-membered heteroaryl ring system, a $(C_1-C_6)$alkyl-$(C_6-C_{10})$aryl ring system, and a $(C_1-C_6)$alkyl-(5- to 9-membered)heteroaryl ring system;

provided that when $R^2$ comprises an aryl or heteroaryl ring system, the ring system bears 0-2 independently selected substituents from the group consisting of fluoro, chloro, trifluoromethyl, $(C_1-C_6)$alkoxy, and $(C_1-C_6)$fluoroalkoxy;

E is $CH_2$, $CH(C_1-C_6)$alkyl, or $CH(C_3-C_7)$cycloalkyl;

J is Q, S, S(O), $S(O)_2$, NH, $N(C_1-C_6)$alkyl, or NC(=O)$(C_1-C_6)$alkyl;

$R^3$ is a monocyclic or bicyclic $(C_6-C_{10})$aryl or a monocyclic or bicyclic (5- to 10-membered) heteroaryl group wherein the aryl or heteroaryl can be substituted or unsubstituted;

$R^4$ is hydrogen, $(C_1-C_6)$alkyl, $(C_3-C_6)$branched alkyl, $(C_1-C_6)$fluoroalkyl, $(C_3-C_7)$cycloalkyl, a (4- to 7-membered)heteroaryl, or a monocyclic or bicyclic $(C_6-C_{10})$aryl or a monocyclic or bicyclic (5- to 10-membered) heteroaryl group wherein the aryl or heteroaryl can be substituted or unsubstituted;

Z is a bond, or is —O—, —$CH_2$—, —CH(Me)-, —S—, —NH—, or —N(C1-C6)alkyl;

n=1, 2, 3, or 4;

the cyclic group indicated as "ring" is an aryl or heteroaryl group of any one of the following formulas:

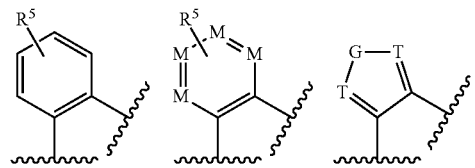

wherein wavy lines indicate points of bonding, and wherein each M is an independently selected CH or N, provided that M group is a nitrogen atom in one or two instances;

G is S, O, NH, N(C$_1$-C$_6$)alkyl, or NCF$_3$.

T is independently at each occurrence CH or N;

wherein R$^5$ is optionally present, R$^5$ being one to four instances of independently selected F, Cl, Br, CF$_3$, (C$_1$-C$_6$)alkyl, OCF$_3$, O(C$_1$-C$_6$)alkyl, or CO—(C$_1$-C$_6$)alkyl;

or, the cyclic group indicated as "ring" is a (C$_3$-C$_7$)cycloalkyl or a saturated (3- to 7-membered)heterocyclyl comprising 1-2 heteroatoms selected from the group consisting of O, NH, N(C1-C6)alkyl, and N(C1-C6)fluoroalkyl; wherein the points of bonding may be cis or trans;

or a pharmaceutically acceptable salt thereof.

In various embodiments, R$^3$ is monocyclic, and the core ring system can consist of 5 or 6 atoms in total, with 1-6 carbon atoms, 0-4 nitrogen atoms, 0-2 oxygen atoms, and 0-1 sulfur atoms. Representative examples of a monocyclic R$^3$ group include:

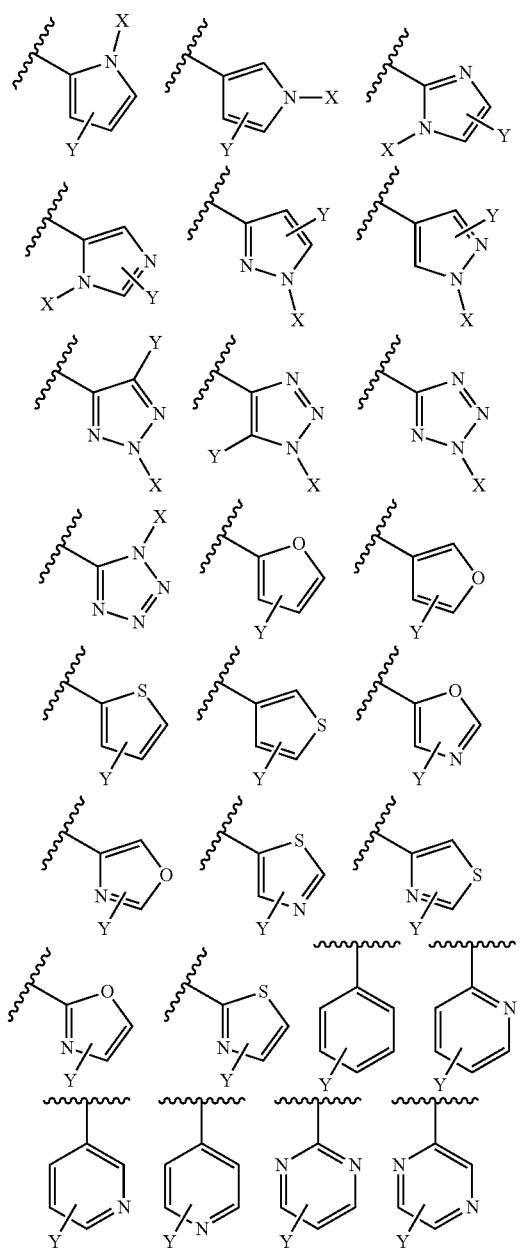

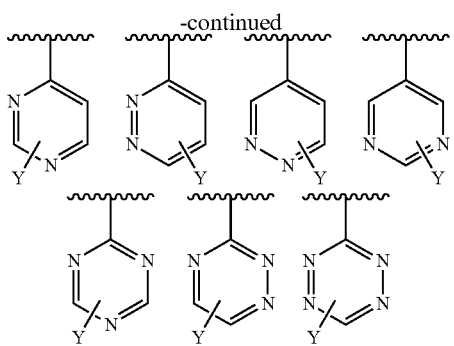

wherein X is H, (C$_1$-C$_6$)alkyl, or CF$_3$;

wherein Y is optionally present and, when present, Y is 1-3 instances of a substituent selected from the group consisting of H, F, Cl, Br, CF$_3$, (C1-C6)alkyl, NH$_2$, NHMe, NMe$_2$, NH(C$_1$-C$_6$)alkyl, N((C$_1$-C$_6$)alkyl)$_2$, O(C$_1$-C$_6$)alkyl; NH—(CH$_2$)$_j$—CH$_2$-Q, and

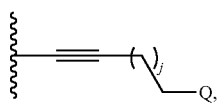

wherein j=2-6, and Q is one of the following:

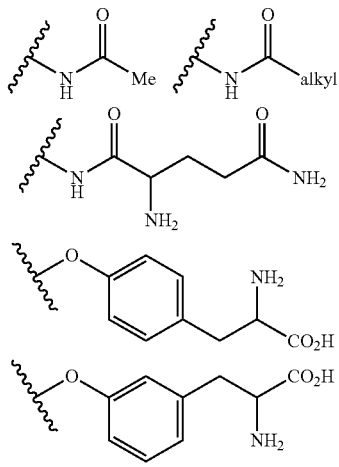

wherein a wavy line indicates a point of bonding.

In various embodiments, R$^3$ is a bicyclic group, wherein the core ring system can consist of 9 or 10 atoms in total, with 4-10 carbon atoms, 0-6 nitrogen atoms, 0-2 oxygen atoms, and 0-2 sulfur atoms.

Examples of 9-atom ring systems include the following:

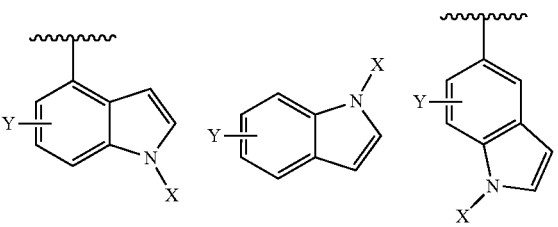

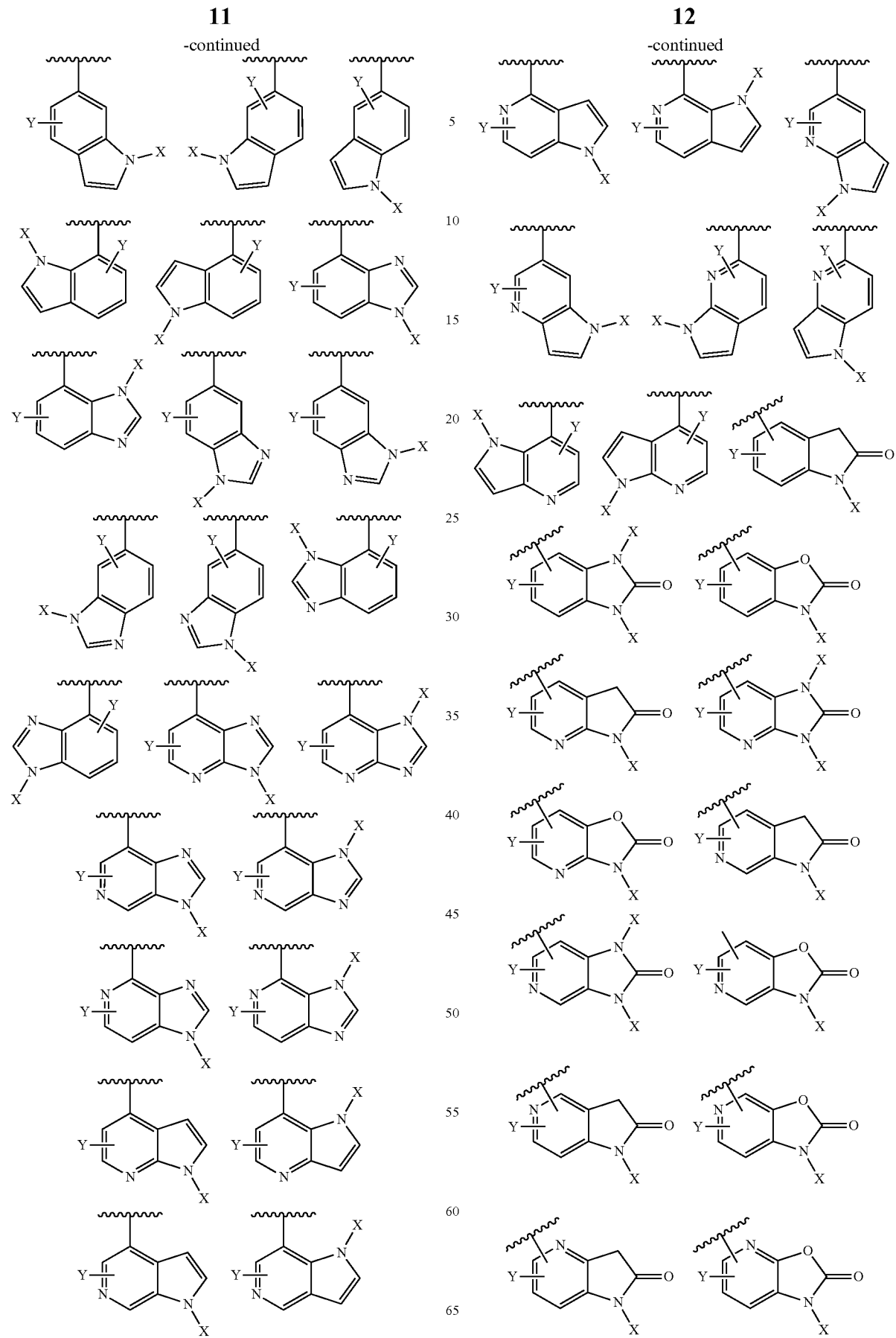

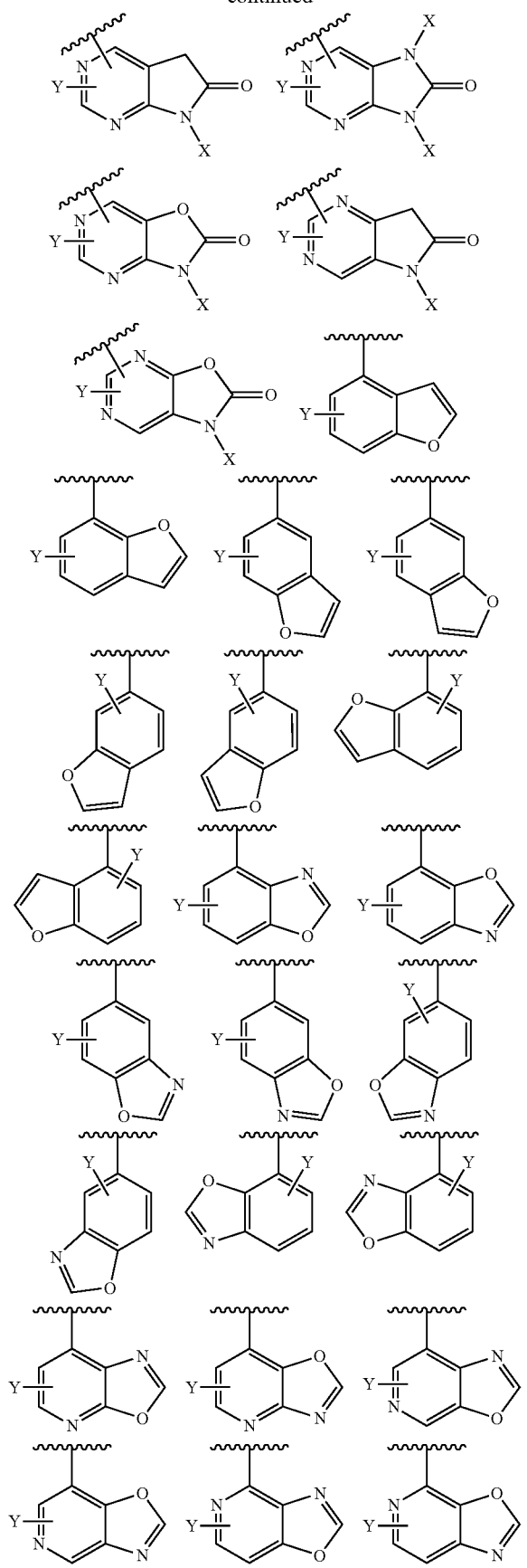
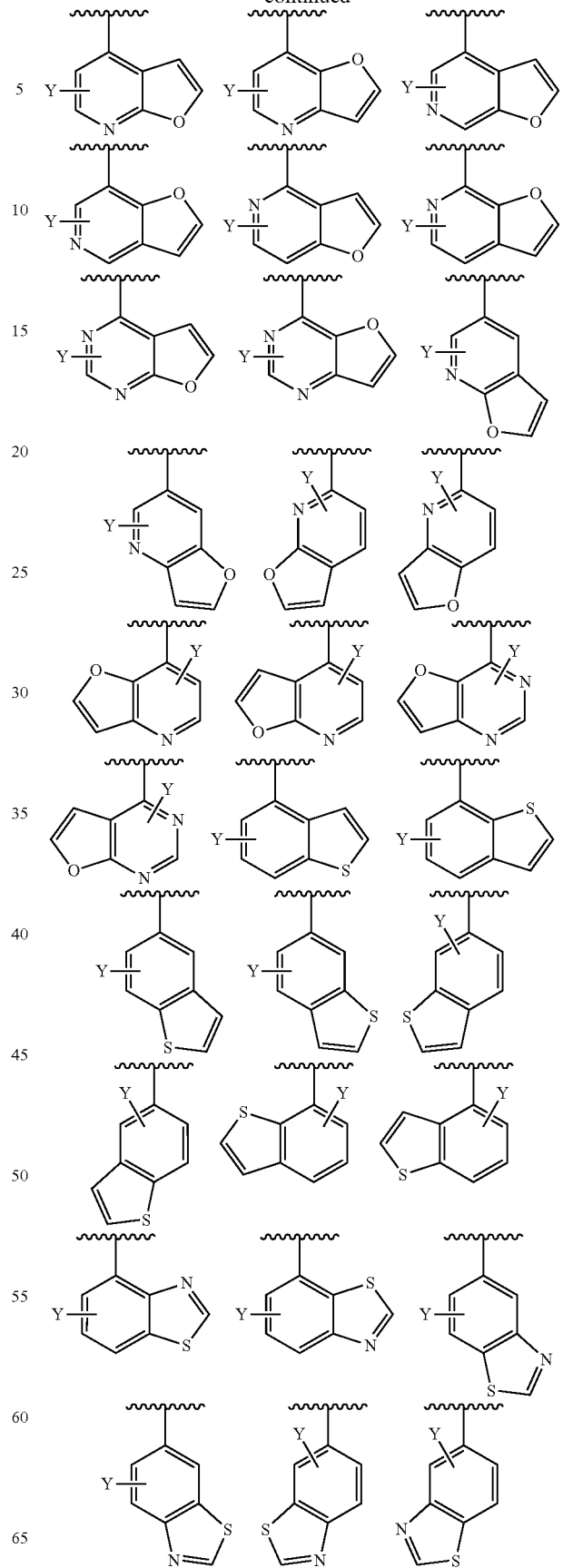

-continued

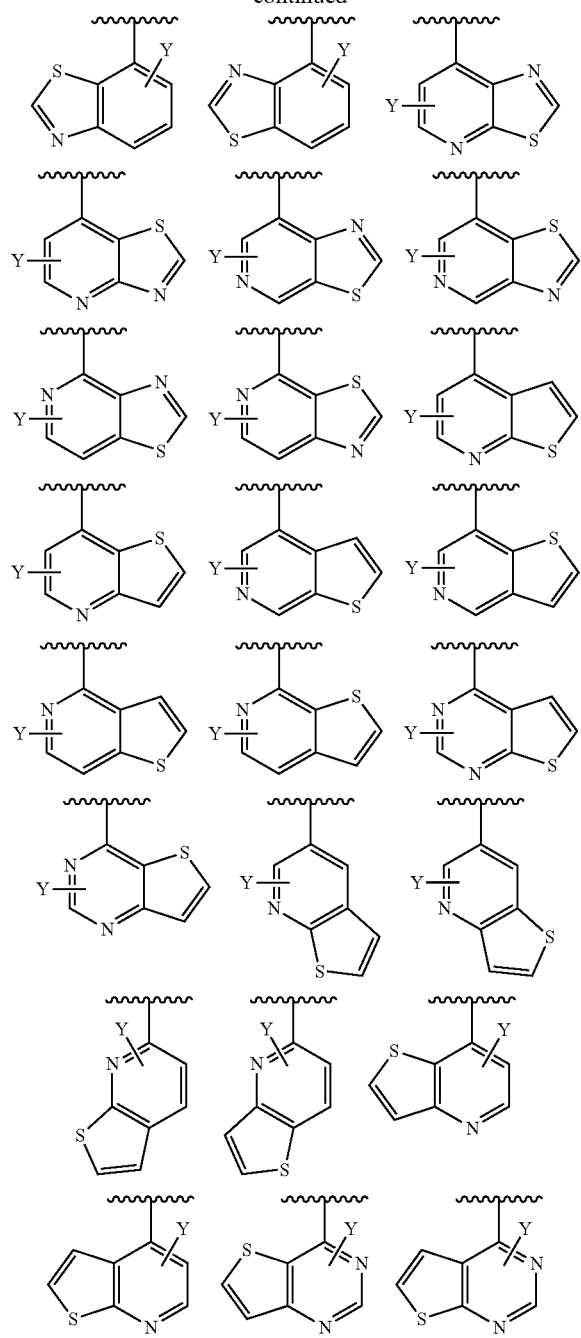

wherein X is H, (C$_1$-C$_6$)alkyl, or CF$_3$;

wherein Y is optionally present and, when present, Y is 1-3 instances of a substituent selected from the group consisting of H, F, Cl, Br, CF$_3$, (C1-C6)alkyl, NH$_2$, NHMe, NMe$_2$, NH(C$_1$-C$_6$)alkyl, N((C$_1$-C$_6$)alkyl)$_2$, O(C$_1$-C$_6$)alkyl; NH—(CH$_2$)$_j$—CH$_2$-Q, and

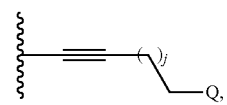

wherein j=2-6, and Q is one of the following:

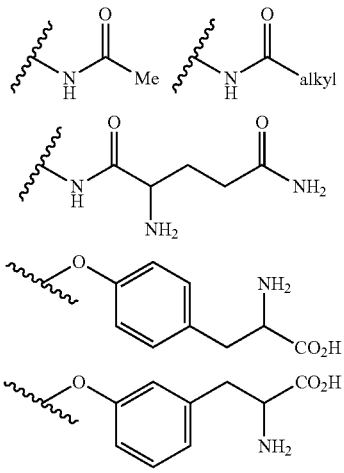

wherein a wavy line indicates a point of bonding, and wherein the group or groups Y, when indicated on a bicyclic ring system above, can be present on either ring, or in both rings.

Examples of 10-atom ring systems include the following:

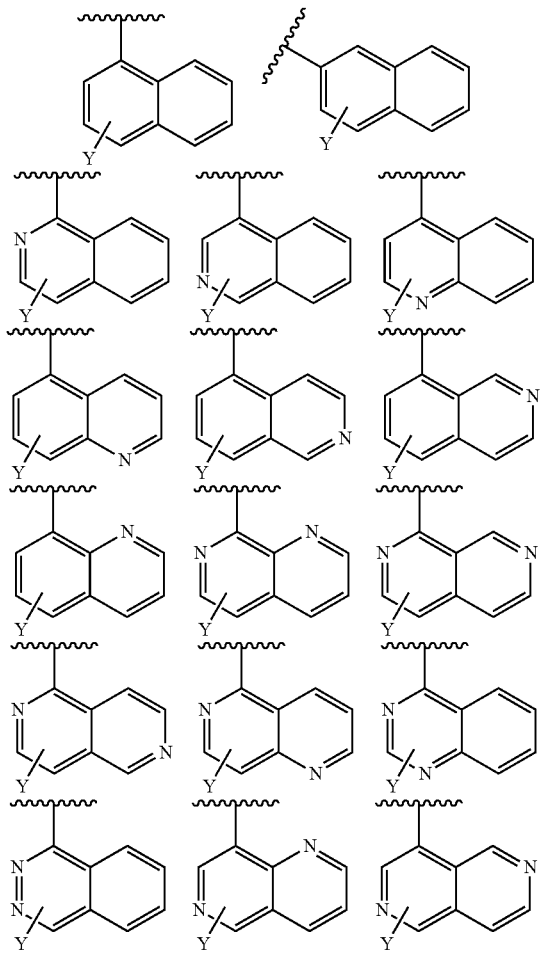

-continued

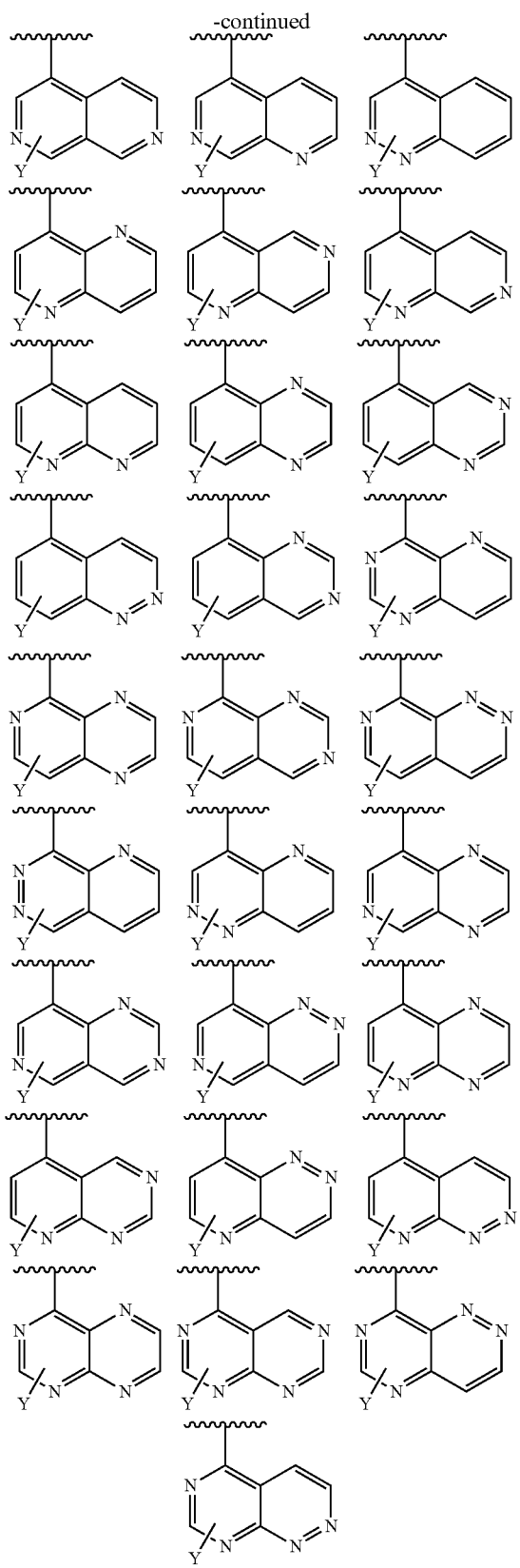

wherein X is H, (C$_1$-C$_6$)alkyl, or CF$_3$;

wherein Y is optionally present and, when present, Y is 1-3 instances of a substituent selected from the group consisting of H, F, Cl, Br, CF$_3$, (C1-C6)alkyl, NH$_2$, NHMe, NMe$_2$, NH(C$_1$-C$_6$)alkyl, N((C$_1$-C$_6$)alkyl)$_2$, O(C$_1$-C$_6$)alkyl; NH—(CH$_2$)$_j$—CH$_2$-Q, and

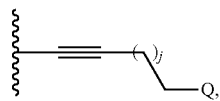

wherein j=2-6, and Q is one of the following:

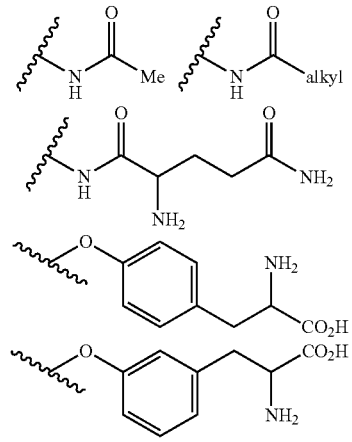

wherein a wavy line indicates a point of bonding, and wherein the group or groups Y, when indicated on a bicyclic ring system above, can be present on either ring, or in both rings.

EXAMPLES

Chemistry Methods

All reactions were performed in flame-dried glassware fitted with rubber septa under positive pressure of nitrogen or argon, unless otherwise noted. Tetrahydrofuran, DMF, acetonitrile, and methylene chloride were purchased from Aldrich and used as received. Commercially available reagents were used without further purification. Thin layer chromatography (TLC) analyses were performed on pre-coated 250 µM silica 60 F254 glass-backed plates. Flash chromatography was performed on pre-packed columns of silica gel (230-400 mesh, 40-63 µm) by CombiFlash with EA/hexane or MeOH/DCM as eluents. Preparative HPLC was performed on a Shimadzu LC-8A preparative HPLC instrument on SunFire C$_{18}$ OBD 10 µm (30×250 mm) with CH$_3$CN+50% MeOH/H$_2$O+0.1% TFA as eluents to purify the targeted compounds. LC-MS was performed on Agilent Technologies 1200 series analytical HPLC instrument paired with a 6140 quadrupole mass spectrometer or with a Thermo Scientific UltiMate 3000 mass spectrometer. Analytical HPLC was performed on Agilent technologies 1200 series with CH$_3$CN (Solvent B)/H$_2$O+0.9% CH$_3$CN+0.1% TFA (solvent A) as eluents, and the targeted products were detected by UV in the detection range of 215-310 nm. $^1$H and $^{13}$C NMR spectra were recorded on a Bruker NMR spectrometer at 400 MHz (H) or 100 MHz ($^{13}$C). Unless otherwise specified, CDCl$_3$ was used as the NMR solvent. Resonances were reported in parts per million downfield from TMS standard, and were referenced to either the residual solvent peak (typically $^1$H: CHCl$_3$ δ 7.27; $^{13}$C: CDCl$_3$ δ 77.23).

Certain abbreviations for common chemicals used in the Examples are defined as follows:
EA=ethyl acetate
ESI=Electrospray ionization mass spectroscopy
NMR=nuclear magnetic resonance spectroscopy
DMSO=dimethyl sulfoxide
DMF=N,N-dimethylformamide
Hex=hexanes
LC-MS=liquid chromatography-mass spectroscopy
HPLC=high performance liquid chromatography
NMO=N-methylmorpholine N-oxide
NMP=N-methyl pyrrolidinone
TEA=triethylamine
DIAD=diisopropyl azodicarboxylate
Tf=trifluoromethansulfonyl
TFA=trifluoroacetic acid Certain compounds of the invention can be made from the synthetic intermediate 7-(((tert-butyldimethylsilyl)oxy)methyl)-1-isobutyl-3-methyl-2,4-dioxo-1,2,3,4-tetrahydropteridin-6-yl trifluoromethanesulfonate (compound 6), prepared as described in Scheme 1 and Example 1. In this case $R^1$ of structures A and B is equal to Me, $R^2$ is equal to i-butyl, E is equal to $CH_2$, and J=O.

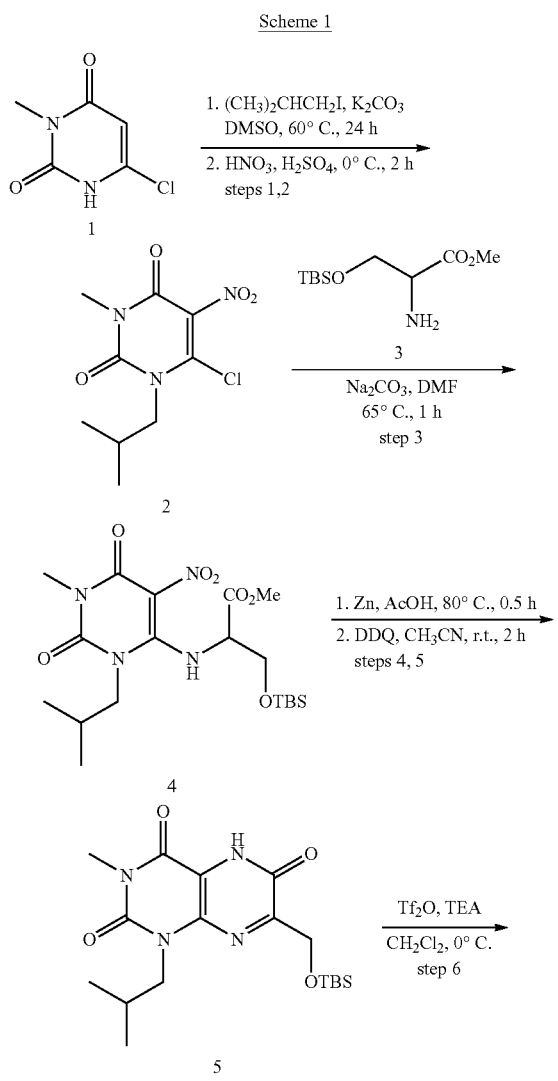

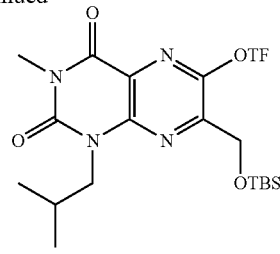

Example 1. 7-(((tert-butyldimethylsilyl)oxy)methyl)-1-isobutyl-3-methyl-2,4-dioxo-1,2,3,4-tetrahydro-pteridin-6-yl trifluoromethanesulfonate Step 1

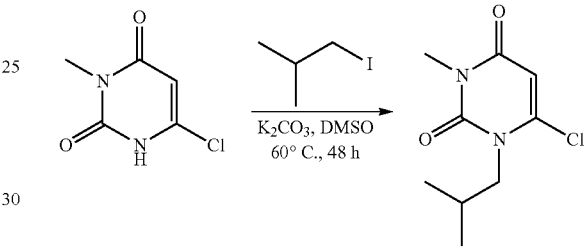

6-Chloro-1-isobutyl-3-methylpyrimidine-2,4(1H,3H)-dione: $K_2CO_3$ (62.19 g, 450.0 mmol) was added to the suspension of 6-chloro-3-methylpyrimidine-2,4(1H,3H)-dione (40.14 g, 250.0 mmol) in DMSO (300 mL). The mixture was stirred at room temperature for 5 min, then 1-iodo-2-methylpropane (46.03 g, 250.0 mmol) was added and the resultant mixture was heated to 60° C. for 24 h. More 1-iodo-2-methylpropane (4.60 g, 25.0 mmol) was added and stirred for an additional 24 h. Water was added to quench the reaction, extracted with EA. The combined organic extracts were washed with $H_2O$ and brine, dried over $Na_2SO_4$. The solvent was removed and the residue was purified by flash column (Hex:EA=4:1 to 3:2) to afford 46.89 g (87%) of 6-Chloro-1-isobutyl-3-methylpyrimidine-2,4(1H,3H)-dione as a colorless solid. $R_f$=0.25 (hex:EA=4:1); LC-MS (ESI): m/z 217 [M+1]$^+$; $^1$H NMR (400 MHz, $CDCl_3$) δ (ppm) 0.96 (d, J=6.8 Hz, 6H), 2.16 (sep, J=6.9 Hz, 1H), 3.33 (s, 3H), 3.90 (d, J=7.0 Hz, 2H), 5.91 (s, 1H).

Step 2

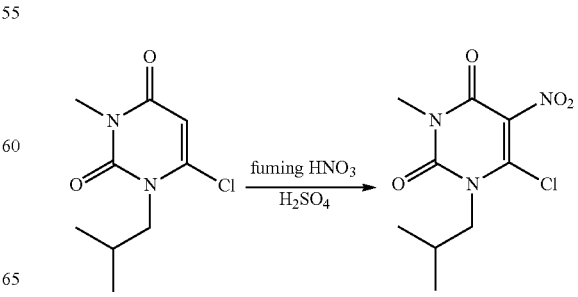

6-Chloro-1-isobutyl-3-methyl-5-nitropyrimidine-2,4(1H,3H)-dione: H$_2$SO$_4$ (340 mL) was cooled to 0° C. and added dropwise to 6-Chloro-1-isobutyl-3-methylpyrimidine-2,4 (1H,3H)-dione (45.40 g, 209.5 mmol) at 0° C. Fuming HNO$_3$ (26.40 g, 419.0 mmol) was added dropwise with vigorous stirring. The resultant mixture was stirred at 0° C. for 1 h, then room temperature for 2 h. Cooled to 0° C. The reaction mixture was slowly poured into ice, extracted with EA. The combined organic extracts were washed with H$_2$O, sat'd NaHCO$_3$, and brine, dried over Na$_2$SO$_4$. The solvent was removed and the residue was purified by column (hex:EA=6:1) to afford 41.94 g (77%) of 6-Chloro-1-isobutyl-3-methyl-5-nitropyrimidine-2,4(1H,3H)-dione as a yellow solid. R$_f$=0.30 (hex:EA=4:1); $^1$H NMR (400 MHz, CDCl$_3$) δ (ppm) 1.01 (d, J=6.8 Hz, 6H), 2.19 (sep, J=6.8 Hz, 1H), 3.42 (s, 3H), 4.01 (d, J=7.6 Hz, 2H).

Step 3

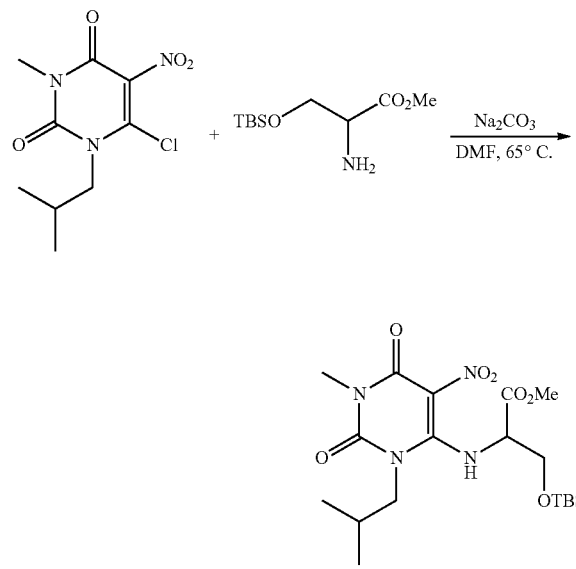

Methyl O-(tert-butyldimethylsilyl)-N-(3-isobutyl-1-methyl-5-nitro-2,6-dioxo-1,2,3,6-tetrahydro-pyrimidin-4-yl)serinate: A mixture of 6-Chloro-1-isobutyl-3-methyl-5-nitropyrimidine-2,4(1H,3H)-dione (18.32 g, 70.0 mmol), methyl O-(tert-butyldimethylsilyl)serinate (17.97 g, 77.0 mmol), Na$_2$CO$_3$ (18.55 g, 175.0 mmol) in DMF (140 mL) was heated to 65° C. for 1 h. The reaction mixture was cooled to room temperature, quenched with saturated NH$_4$Cl, extracted with EA. The combined organic extracts were washed with brine three times and dried over Na$_2$SO$_4$. The solvent was removed and the residue was purified by column (hex:EA=3:2 to 1:1) to afford 24.62 g (76%) of methyl O-(tert-butyldimethylsilyl)-N-(3-isobutyl-1-methyl-5-nitro-2,6-dioxo-1,2,3,6-tetrahydropyrimidin-4-yl)serinate as a yellow solid. R$_f$=0.60 (hex:EA=1:1); LC-MS (ESI): m/z 459 [M+1]$^+$; $^1$H NMR (400 MHz, CDCl$_3$) δ (ppm) 0.01 (s, 6H), 0.83 (s, 9H), 0.97 (d, J=6.8 Hz, 6H), 2.17 (sep, J=6.8 Hz, 1H), 3.33 (s, 3H), 3.70 (s, 1H), 3.77-4.10 (m, 5H).

Step 4

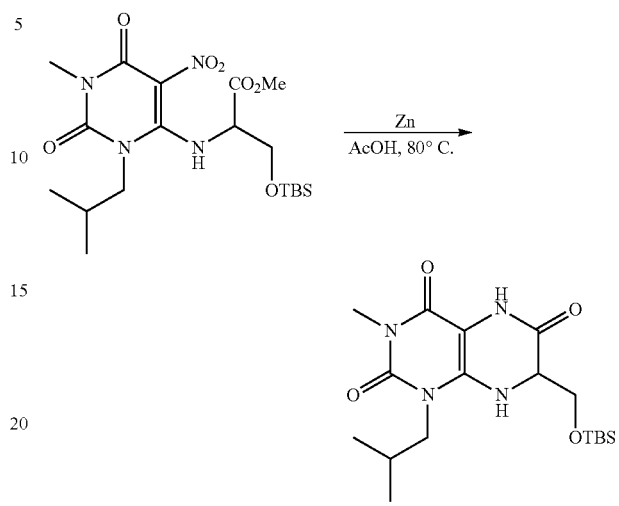

7-(((tert-butyldimethylsilyl)oxy)methyl)-1-isobutyl-3-methyl-1,5,7,8-tetrahydropteridine-2,4,6(3H)-trione: A solution of methyl O-(tert-butyldimethylsilyl)-N-(3-isobutyl-1-methyl-5-nitro-2,6-dioxo-1,2,3,6-tetrahydropyrimidin-4H) serinate (24.62 g, 53.69 mmol) in AcOH (322 mL) was heated to 80° C. under N$_2$. Zinc (42.12 g, 644.0 mmol) was added portionwise. The resultant mixture was stirred at 80° C. for 30 min. The reaction was cooled to room temperature and filtered. The filtrate was concentrated. The residue was dissolved in EA, washed with H$_2$O, saturated NaHCO$_3$, and brine, dried over Na$_2$SO$_4$. The solvent was removed to afford 23.94 g of 7-(((tert-butyldimethylsilyl)oxy)methyl)-1-isobutyl-3-methyl-1,5,7,8-tetrahydropteridine-2,4,6(3H)-trione as an orange oil, which was used directly for the next step. LC-MS (ESI): m/z 397 [M+1]$^+$.

Step 5

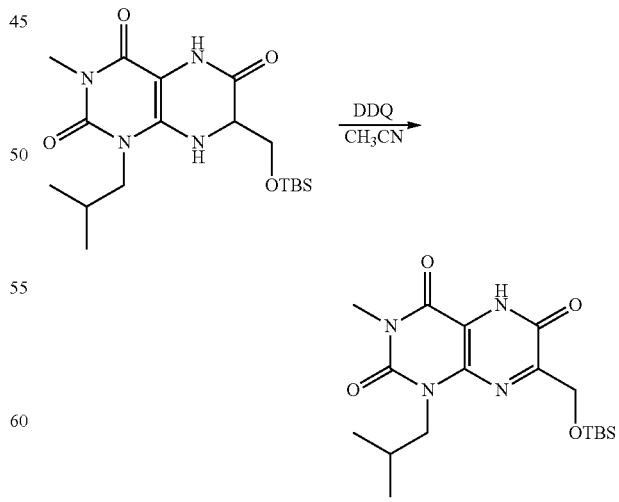

7-(((tert-butyldimethylsilyl)oxy)methyl)-1-isobutyl-3-methyl-1,5-dihydropteridine-2,4,6(3H)-trione: A solution of 7-(((tert-butyldimethylsilyl)oxy)methyl)-1-isobutyl-3- methyl-1,5,7,8-tetrahydropteridine-2,4,6(3H)-trione (23.94 g) in CH$_3$CN (430 mL) was treated with DDQ (12.19 g, 53.69 mmol) portionwise. The reaction mixture was stirred at room temperature for an additional 1 h. The precipitate was collected by filtration to afford 16.40 g (77% for 2 steps) of 7-(((tert-butyldimethylsilyl)oxy)methyl)-1-isobutyl-3-methyl-1,5-dihydropteridine-2,4,6(3H)-trione as a yellow solid. LC-MS (ESI): m/z 395 [M+1]$^+$; $^1$H NMR (400 MHz, CDCl$_3$) δ (ppm) 0.00 (s, 6H), 0.78 (d, J=6.8 Hz, 6H), 0.83 (s, 9H), 2.13 (sep, J=6.8 Hz, 1H), 3.34 (s, 3H), 4.03 (d, J=7.2 Hz, 2H), 4.90 (s, 2H).

Step 6

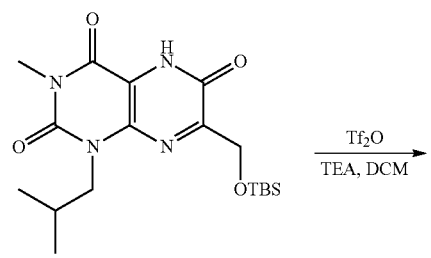

$\xrightarrow{\text{Tf}_2\text{O}}{\text{TEA, DCM}}$

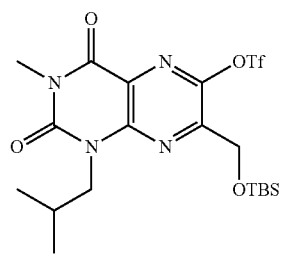

General Scheme 2

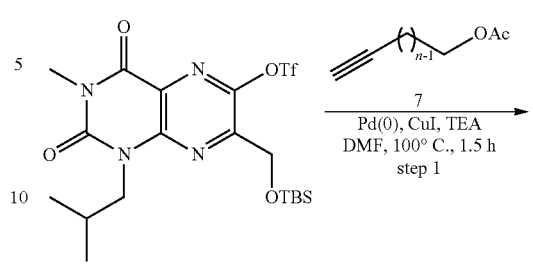

$\xrightarrow[\text{DMF, 100° C., 1.5 h}]{\text{Pd(0), CuI, TEA}}$
step 1

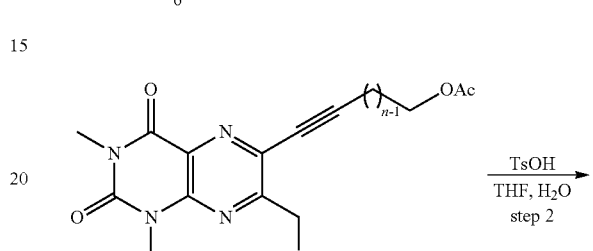

$\xrightarrow[\text{THF, H}_2\text{O}]{\text{TsOH}}$
step 2

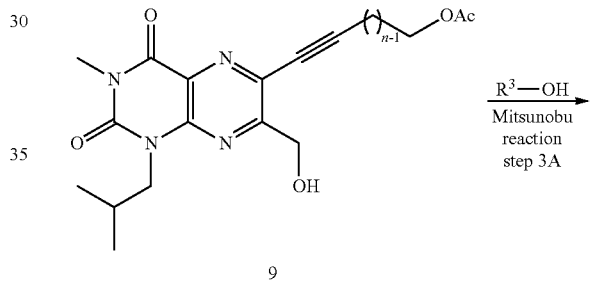

$\xrightarrow[\text{Mitsunobu reaction}]{\text{R}^3\text{—OH}}$
step 3A

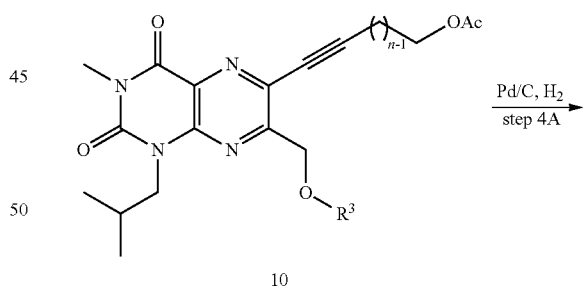

$\xrightarrow{\text{Pd/C, H}_2}$
step 4A

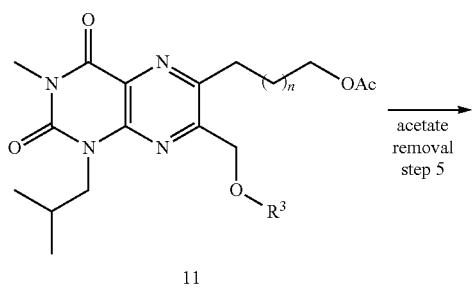

$\xrightarrow[\text{removal}]{\text{acetate}}$
step 5

The product of Example 1: 7-(((tert-butyldimethylsilyl)oxy)methyl)-1-isobutyl-3-methyl-2,4-dioxo-1,2,3,4-tetrahydropteridin-6-yl trifluoromethanesulfonate: A suspension of 7-(((tert-butyldimethylsilyl)oxy)methyl)-1-isobutyl-3-methyl-1,5-dihydropteridine-2,4,6(3H)-trione (5.77 g, 14.63 mmol) in CH$_2$Cl$_2$ (120 mL) was cooled to 0° C. under N$_2$. TEA (4.44 g, 43.89 mmol) was added followed by Tf$_2$O (7.43 g, 26.33 mmol). The resultant mixture was stirred at 0° C. for 1 h, diluted with EA, washed with brine, dried over Na$_2$SO$_4$. The solvent was removed and the residue was purified by column (Hex:EA=4:1) to afford 5.07 g (66%) of 7-(((tert-butyldimethylsilyl)oxy)methyl)-1-isobutyl-3-methyl-2,4-dioxo-1,2,3,4-tetrahydropteridin-6-yl trifluoromethanesulfonate as a yellow oil. LC-MS (ESI): m/z 527 [M+1]$^+$; $^1$H NMR (400 MHz, CDCl$_3$) δ (ppm) 0.00 (s, 6H), 0.78-0.81 (m, 15H), 2.10 (sep, J=6.8 Hz, 1H), 3.37 (s, 3H), 4.04 (d, J=7.2 Hz, 2H), 4.80 (s, 2H); $^{19}$F NMR (400 MHz, CDCl$_3$) δ (ppm) −71.6.

Certain compounds of the invention were made using the product of Example 1 as the starting material and following the procedures of General Scheme 2:

25
-continued

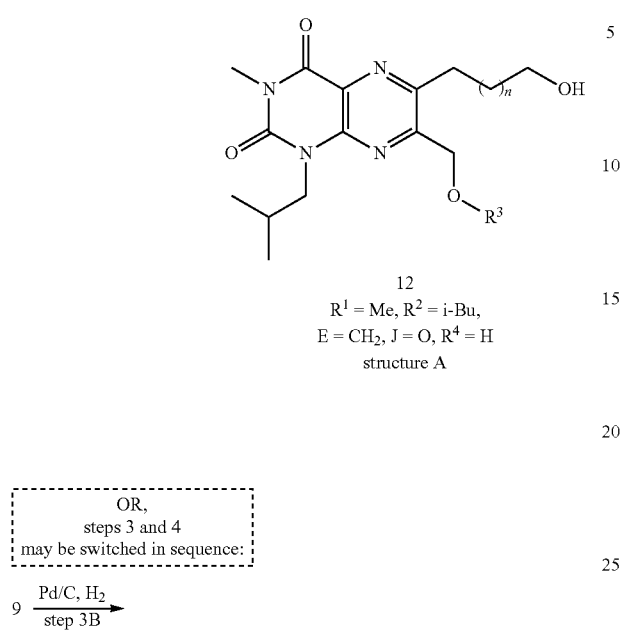

12
$R^1$ = Me, $R^2$ = i-Bu,
E = $CH_2$, J = O, $R^4$ = H
structure A

OR,
steps 3 and 4
may be switched in sequence:

9 $\xrightarrow{\text{Pd/C, H}_2}_{\text{step 3B}}$

26
-continued

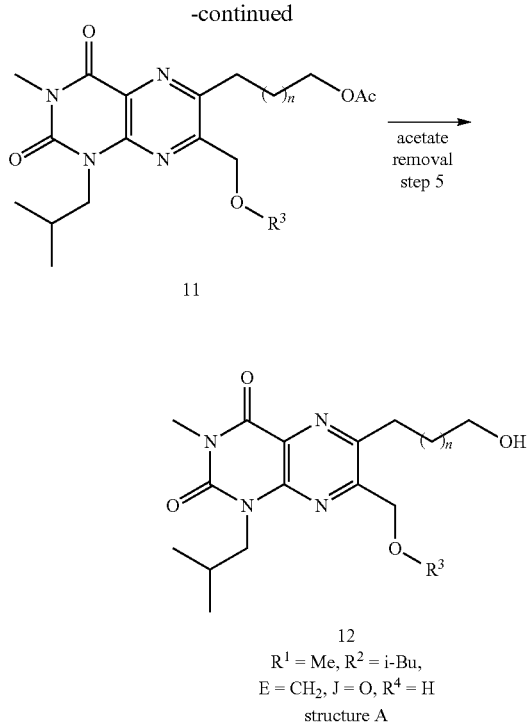

11 $\xrightarrow{\text{acetate removal step 5}}$

12
$R^1$ = Me, $R^2$ = i-Bu,
E = $CH_2$, J = O, $R^4$ = H
structure A

The following compounds were made according to the methods of General Scheme 2:

13 $\xrightarrow{\text{R}^3-\text{OH}}_{\substack{\text{Mitsunobu}\\\text{reaction}\\\text{step 4B}}}$

A

TABLE 1

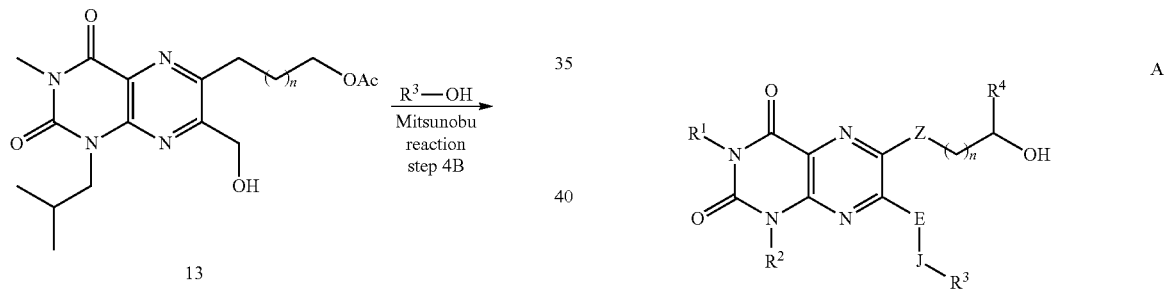

| example | chemical structure | type | groups present |
|---|---|---|---|
| 2 | 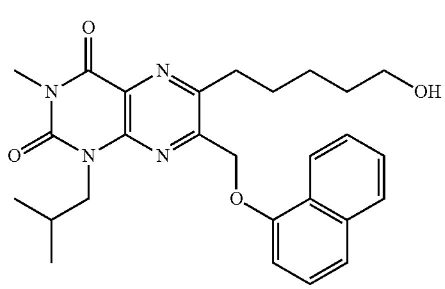 [SMILES: CC(C)Cn1c(=O)n(C)c(=O)c2nc(CCCCCO)c(COc3cccc4ccccc34)nc21] | A | $R^1$ = Me, $R^2$ = i-Bu, $R^4$ = H, Z = $CH_2$, n = 3, E = $CH_2$, J = O, $R^3$ = Y— [naphthyl] wherein Y = H |

TABLE 1-continued

| example | chemical structure | type | groups present |
|---|---|---|---|
| 3 | 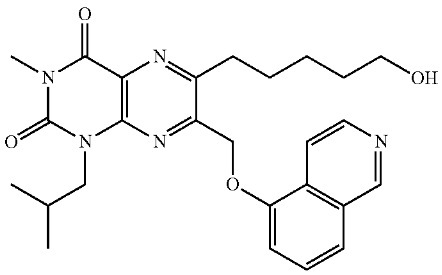 [SMILES: CC(C)Cn1c(=O)n(C)c(=O)c2nc(CCCCCO)c(COc3cccc4cnccc34)nc21] | A | $R^1$ = Me, $R^2$ = i-Bu, $R^4$ = H, Z = $CH_2$, n = 3, E = $CH_2$, J = O, $R^3$ = 5-isoquinolinyl wherein Y = H |
| 4 | 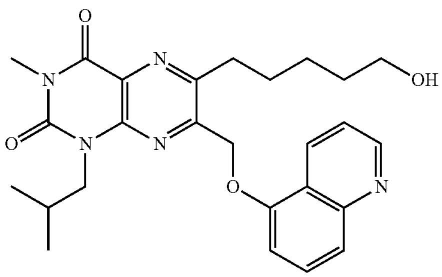 [SMILES: CC(C)Cn1c(=O)n(C)c(=O)c2nc(CCCCCO)c(COc3cccc4ncccc34)nc21] | A | $R^1$ = Me, $R^2$ = i-Bu, $R^4$ = H, Z = $CH_2$, n = 3, E = $CH_2$, J = O, $R^3$ = 5-quinolinyl wherein Y = H |
| 5 | 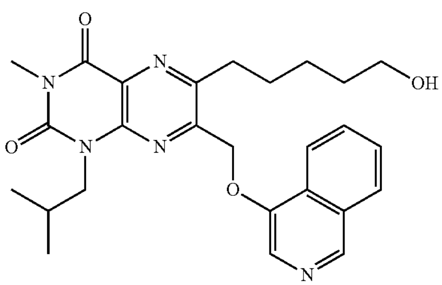 [SMILES: CC(C)Cn1c(=O)n(C)c(=O)c2nc(CCCCCO)c(COc3cncc4ccccc34)nc21] | A | $R^1$ = Me, $R^2$ = i-Bu, $R^4$ = H, Z = $CH_2$, n = 3, E = $CH_2$, J = O, $R^3$ = 4-isoquinolinyl wherein Y = H |
| 6 | 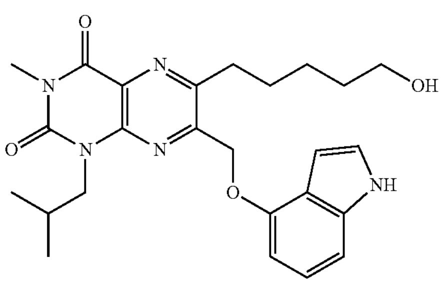 [SMILES: CC(C)Cn1c(=O)n(C)c(=O)c2nc(CCCCCO)c(COc3cccc4[nH]ccc34)nc21] | A | $R^1$ = Me, $R^2$ = i-Bu, $R^4$ = H, Z = $CH_2$, n = 3, E = $CH_2$, J = O, $R^3$ = 4-indolyl wherein Y = H |
| 7 | 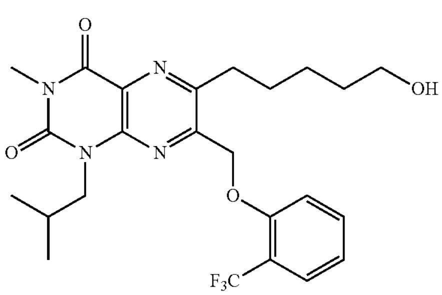 [SMILES: CC(C)Cn1c(=O)n(C)c(=O)c2nc(CCCCCO)c(COc3ccccc3C(F)(F)F)nc21] | A | $R^1$ = Me, $R^2$ = i-Bu, $R^4$ = H, Z = $CH_2$, n = 3, E = $CH_2$, J = O, $R^3$ = phenyl wherein Y = ortho-$CF_3$ |

TABLE 1-continued

| example | chemical structure | type | groups present |
|---|---|---|---|
| 8 | 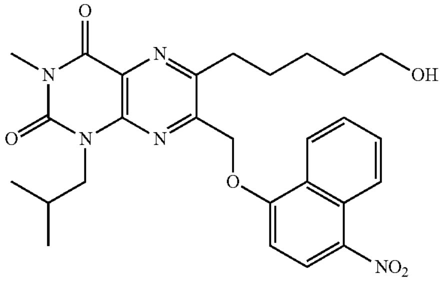 | A | $R^1$ = Me, $R^2$ = i-Bu, $R^4$ = H, Z = $CH_2$, n = 3, E = $CH_2$, J = O, $R^3$ = naphthyl wherein Y = $NO_2$ |
| 9 | 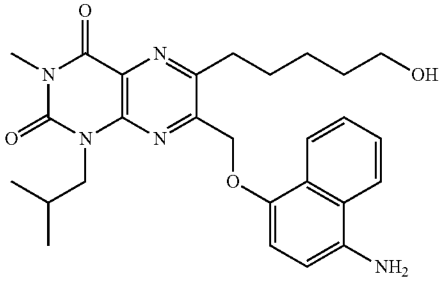 | A | $R^1$ = Me, $R^2$ = i-Bu, $R^4$ = H, Z = $CH_2$, n = 3, E = $CH_2$, J = O, $R^3$ = naphthyl wherein Y = $NH_2$ |
| 10 | 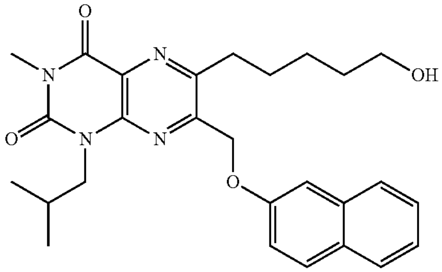 [SMILES: CC(C)Cn1c(=O)n(C)c(=O)c2nc(CCCCCO)c(COc3ccc4ccccc4c3)nc21] | A | $R^1$ = Me, $R^2$ = i-Bu, $R^4$ = H, Z = $CH_2$, n = 3, E = $CH_2$, J = O, $R^3$ = naphthyl wherein Y = H |
| 11 | 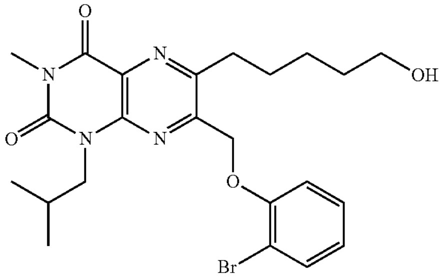 [SMILES: CC(C)Cn1c(=O)n(C)c(=O)c2nc(CCCCCO)c(COc3ccccc3Br)nc21] | A | $R^1$ = Me, $R^2$ = i-Bu, $R^4$ = H, Z = $CH_2$, n = 3, E = $CH_2$, J = O, $R^3$ = phenyl wherein Y = ortho-Br |
| 12 | 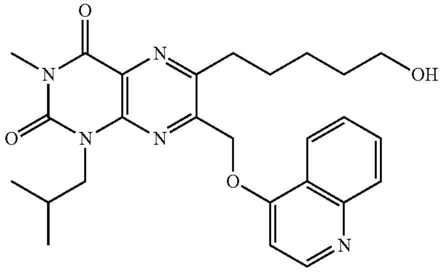 [SMILES: CC(C)Cn1c(=O)n(C)c(=O)c2nc(CCCCCO)c(COc3ccnc4ccccc34)nc21] | A | $R^1$ = Me, $R^2$ = i-Bu, $R^4$ = H, Z = $CH_2$, n = 3, E = $CH_2$, J = O, $R^3$ = quinolinyl wherein Y = H |

TABLE 1-continued

| example | chemical structure | type | groups present |
|---|---|---|---|
| 13 | 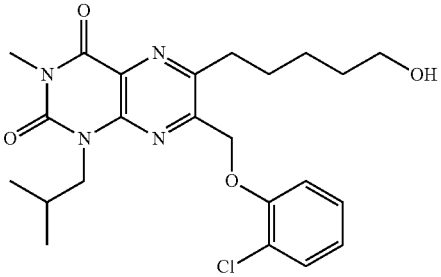 [SMILES: CC(C)Cn1c(=O)n(C)c(=O)c2nc(CCCCCO)c(COc3ccccc3Cl)nc21] | A | $R^1$ = Me, $R^2$ = i-Bu, $R^4$ = H, Z = $CH_2$, n = 3, E = $CH_2$, J = O, <br><br> $R^3$ =  wherein Y = ortho-Cl |
| 14 | 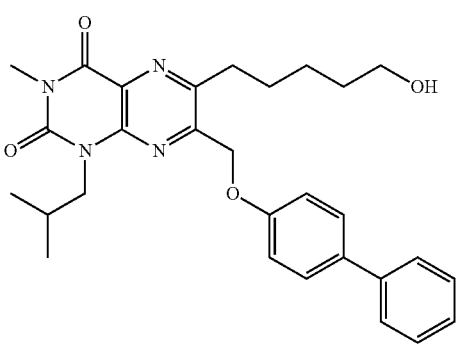 [SMILES: CC(C)Cn1c(=O)n(C)c(=O)c2nc(CCCCCO)c(COc3ccc(-c4ccccc4)cc3)nc21] | A | $R^1$ = Me, $R^2$ = i-Bu, $R^4$ = H, Z = $CH_2$, n = 3, E = $CH_2$, J = O, <br><br> $R^3$ =  wherein Y = para-phenyl |
| 15 | 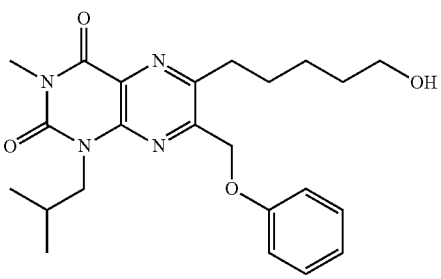 [SMILES: CC(C)Cn1c(=O)n(C)c(=O)c2nc(CCCCCO)c(COc3ccccc3)nc21] | A | $R^1$ = Me, $R^2$ = i-Bu, $R^4$ = H, Z = $CH_2$, n = 3, E = $CH_2$, J = O, <br><br> $R^3$ =  wherein Y = H |
| 16 | 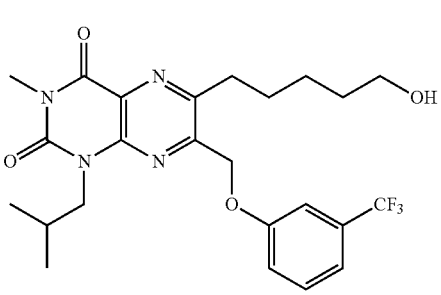 [SMILES: CC(C)Cn1c(=O)n(C)c(=O)c2nc(CCCCCO)c(COc3cccc(C(F)(F)F)c3)nc21] | A | $R^1$ = Me, $R^2$ = i-Bu, $R^4$ = H, Z = $CH_2$, n = 3, E = $CH_2$, J = O, <br><br> $R^3$ =  wherein Y = meta-$CF_3$ |
| 17 | 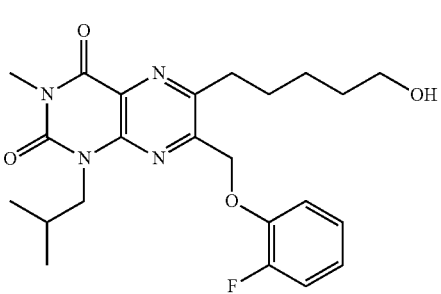 [SMILES: CC(C)Cn1c(=O)n(C)c(=O)c2nc(CCCCCO)c(COc3ccccc3F)nc21] | A | $R^1$ = Me, $R^2$ = i-Bu, $R^4$ = H, Z = $CH_2$, n = 3, E = $CH_2$, J = O, <br><br> $R^3$ =  wherein Y = ortho-F |

TABLE 1-continued

| example | chemical structure | type | groups present |
|---|---|---|---|
| 18 | 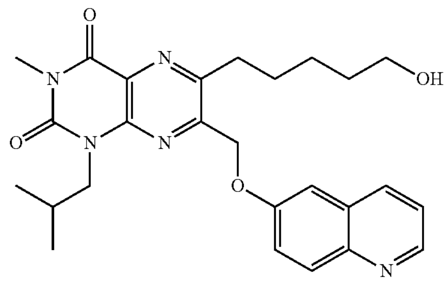 [SMILES: CC(C)Cn1c(=O)n(C)c(=O)c2nc(CCCCCO)c(COc3ccc4ncccc4c3)nc21] | A | $R^1$ = Me, $R^2$ = i-Bu, $R^4$ = H, Z = $CH_2$, n = 3, E = $CH_2$, J = O, $R^3$ = 6-quinolinyl wherein Y = H |
| 19 | 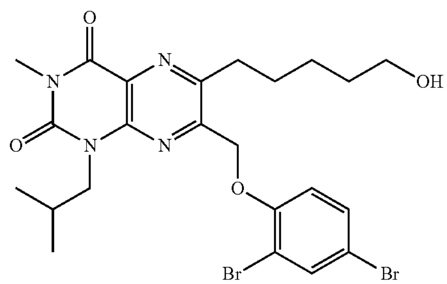 | A | $R^1$ = Me, $R^2$ = i-Bu, $R^4$ = H, Z = $CH_2$, n = 3, E = $CH_2$, J = O, $R^3$ = phenyl wherein Y = ortho, para-dibromo |
| 20 | 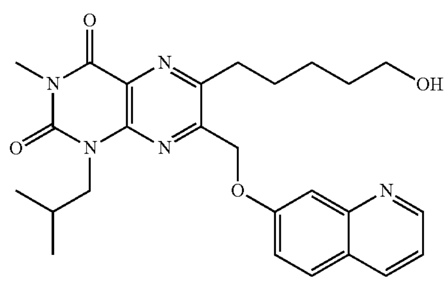 [SMILES: CC(C)Cn1c(=O)n(C)c(=O)c2nc(CCCCCO)c(COc3ccc4cccnc4c3)nc21] | A | $R^1$ = Me, $R^2$ = i-Bu, $R^4$ = H, Z = $CH_2$, n = 3, E = $CH_2$, J = O, $R^3$ = 7-quinolinyl wherein Y = H |
| 21 | 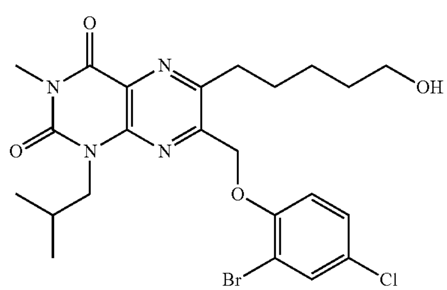 [SMILES: CC(C)Cn1c(=O)n(C)c(=O)c2nc(CCCCCO)c(COc3ccc(Cl)cc3Br)nc21] | A | $R^1$ = Me, $R^2$ = i-Bu, $R^4$ = H, Z = $CH_2$, n = 3, E = $CH_2$, J = O, $R^3$ = phenyl wherein Y = ortho-Cl, para-Br |
| 22 | 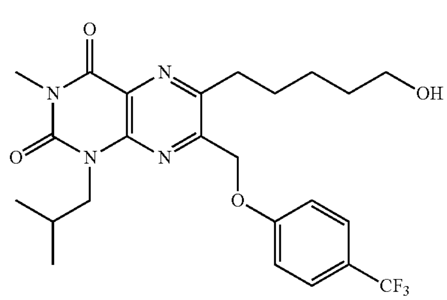 [SMILES: CC(C)Cn1c(=O)n(C)c(=O)c2nc(CCCCCO)c(COc3ccc(C(F)(F)F)cc3)nc21] | A | $R^1$ = Me, $R^2$ = i-Bu, $R^4$ = H, Z = $CH_2$, n = 3, E = $CH_2$, J = O, $R^3$ = phenyl wherein Y = ortho, para-$CF_3$ |

TABLE 1-continued

| example | chemical structure | type | groups present |
|---|---|---|---|
| 23 | 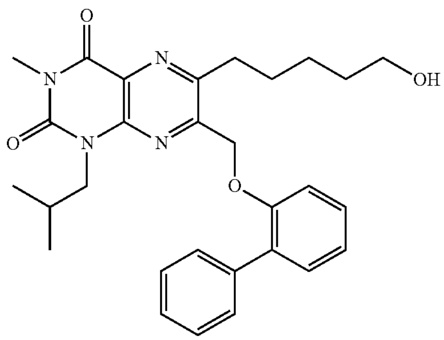 [SMILES: CC(C)Cn1c(=O)n(C)c(=O)c2nc(CCCCCO)c(COc3ccccc3-c3ccccc3)nc21] | A | $R^1$ = Me, $R^2$ = i-Bu, $R^4$ = H, Z = $CH_2$, n = 3, E = $CH_2$, J = O, $R^3$ = phenyl with Y, wherein Y = ortho-phenyl |
| 24 | 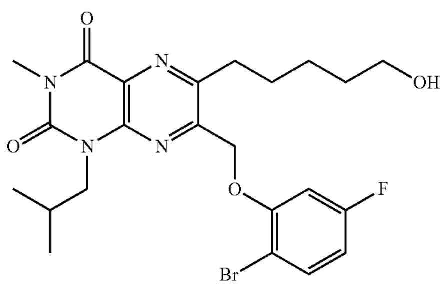 [SMILES: CC(C)Cn1c(=O)n(C)c(=O)c2nc(CCCCCO)c(COc3cc(F)ccc3Br)nc21] | A | $R^1$ = Me, $R^2$ = i-Bu, $R^4$ = H, Z = $CH_2$, n = 3, E = $CH_2$, J = O, $R^3$ = phenyl with Y, wherein Y = ortho-Br, meta'-F |
| 25 | 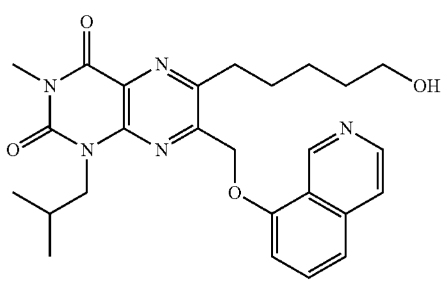 [SMILES: CC(C)Cn1c(=O)n(C)c(=O)c2nc(CCCCCO)c(COc3cccc4ccncc34)nc21] | A | $R^1$ = Me, $R^2$ = i-Bu, $R^4$ = H, Z = $CH_2$, n = 3, E = $CH_2$, J = O, $R^3$ = isoquinolinyl with Y, wherein Y = H |
| 26 | 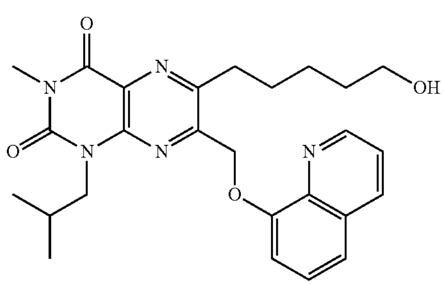 [SMILES: CC(C)Cn1c(=O)n(C)c(=O)c2nc(CCCCCO)c(COc3cccc4cccnc34)nc21] | A | $R^1$ = Me, $R^2$ = i-Bu, $R^4$ = H, Z = $CH_2$, n = 3, E = $CH_2$, J = O, $R^3$ = quinolinyl with Y, wherein Y = H |
| 27 | 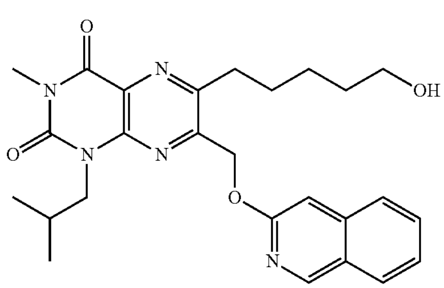 [SMILES: CC(C)Cn1c(=O)n(C)c(=O)c2nc(CCCCCO)c(COc3cc4ccccc4cn3)nc21] | A | $R^1$ = Me, $R^2$ = i-Bu, $R^4$ = H, Z = $CH_2$, n = 3, E = $CH_2$, J = O, $R^3$ = isoquinolinyl with Y, wherein Y = H |

TABLE 1-continued

| example | chemical structure | type | groups present |
| --- | --- | --- | --- |
| 28 | 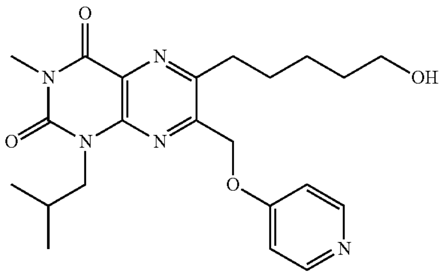 [SMILES: CC(C)Cn1c(=O)n(C)c(=O)c2nc(CCCCCO)c(COc3ccncc3)nc21] | A | $R^1$ = Me, $R^2$ = i-Bu, $R^4$ = H, Z = $CH_2$, n = 3, E = $CH_2$, J = O, $R^3$ = 4-pyridyl wherein Y = H |
| 29 | 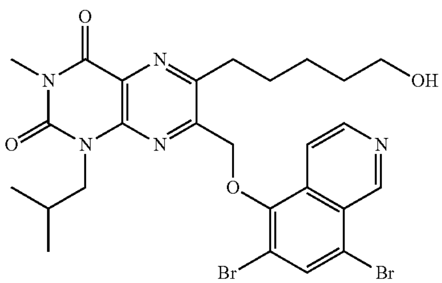 [SMILES: CC(C)Cn1c(=O)n(C)c(=O)c2nc(CCCCCO)c(COc3c(Br)cc(Br)c4cnccc34)nc21] | A | $R^1$ = Me, $R^2$ = i-Bu, $R^4$ = H, Z = $CH_2$, n = 3, E = $CH_2$, J = O, $R^3$ = isoquinolin-5-yl wherein Y = dibromo |
| 30 | 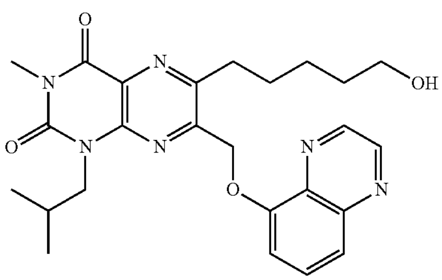 [SMILES: CC(C)Cn1c(=O)n(C)c(=O)c2nc(CCCCCO)c(COc3cccc4nccnc34)nc21] | A | $R^1$ = Me, $R^2$ = i-Bu, $R^4$ = H, Z = $CH_2$, n = 3, E = $CH_2$, J = O, $R^3$ = quinoxalin-5-yl wherein Y = H |
| 31 | 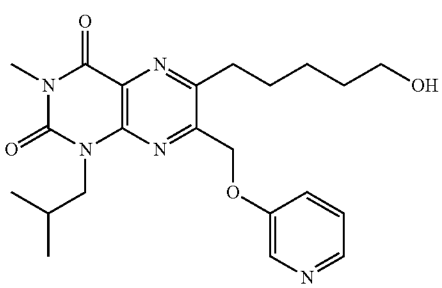 [SMILES: CC(C)Cn1c(=O)n(C)c(=O)c2nc(CCCCCO)c(COc3cccnc3)nc21] | A | $R^1$ = Me, $R^2$ = i-Bu, $R^4$ = H, Z = $CH_2$, n = 3, E = $CH_2$, J = O, $R^3$ = 3-pyridyl wherein Y = H |
| 32 | 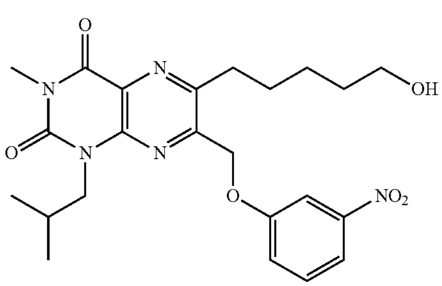 [SMILES: CC(C)Cn1c(=O)n(C)c(=O)c2nc(CCCCCO)c(COc3cccc([N+](=O)[O-])c3)nc21] | A | $R^1$ = Me, $R^2$ = i-Bu, $R^4$ = H, Z = $CH_2$, n = 3, E = $CH_2$, J = O, $R^3$ = phenyl wherein Y = meta-$NO_2$ |

TABLE 1-continued

| example | chemical structure | type | groups present |
|---|---|---|---|
| 33 | 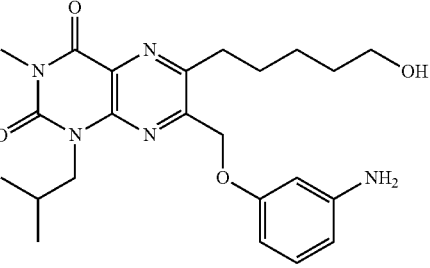 | A | $R^1$ = Me, $R^2$ = i-Bu, $R^4$ = H, Z = $CH_2$, n = 3, E = $CH_2$, J = O, $R^3$ =  wherein Y = meta-$NH_2$ |
| 34 | 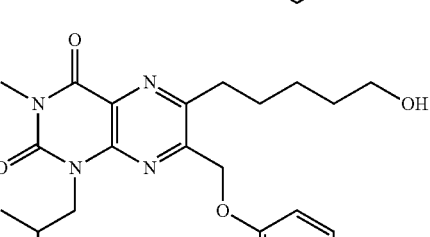 | A | $R^1$ = Me, $R^2$ = i-Bu, $R^4$ = H, Z = $CH_2$, n = 3, E = $CH_2$, J = O, $R^3$ = 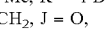 wherein Y = ortho-CN |

Example 2. 6-(5-hydroxypentyl)-1-isobutyl-3-methyl-7-((naphthalen-1-yloxy)methyl)pteridine-2,4(1H,3H)-dione

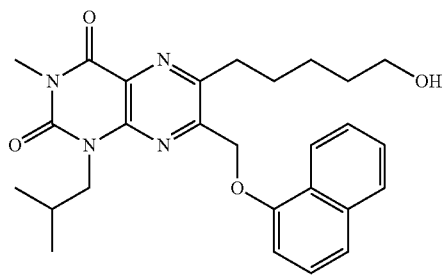

Step 1

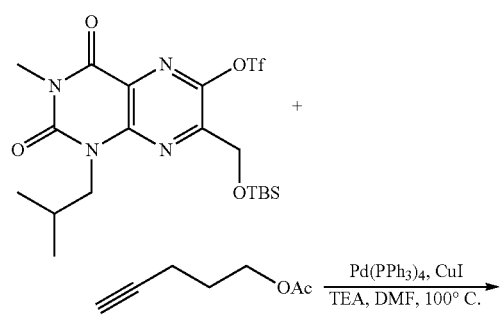

-continued 5-7-(((tert-butyldimethylsilyl)oxy)methyl)-1-isobutyl-3-methyl-2,4-dioxo-1,2,3,4-tetrahydropteridin-6-yl)pent-4-yn-1-yl acetate: A mixture of 7-(((tert-butyldimethylsilyl)oxy)methyl)-1-isobutyl-3-methyl-2,4-dioxo-1,2,3,4-tetrahydropteridin-6-yl trifluoromethanesulfonate (5.07 g, 9.63 mmol), pent-4-yn-1-yl acetate (2.19 g, 17.33 mmol), and CuI (275 mg, 1.44 mmol) in DMF (144 mL) was degassed. $Pd(PPh_3)_4$ (556 mg, 0.482 mmol) was added followed by TEA (5.85 g, 57.78 mmol), and degassed. The reaction was stirred at 100° C. for 1.5 hours, then cooled to room temperature. The reaction was quenched with saturated $NH_4Cl$, extracted with EA. The combined organic extracts were washed with brine, dried over $Na_2SO_4$. The solvent was removed and the residue was purified by column (Hex:EA=2:1) to afford 2.32 g (48%) of 5-7-(((tert-butyldimethylsilyl)oxy)methyl)-1-isobutyl-3-methyl-2,4-dioxo-1,2,3,4-tetrahydropteridin-6-yl)pent-4-yn-1-ylacetate as a yellow oil. $R_f$=0.55 (Hex:EA=1:1); LC-MS (ESI): m/z 503 [M+1]$^+$. $^1$H NMR (400 MHz, $CDCl_3$) δ (ppm) s (0.00, 6H), 0.79 (d, J=6.8 Hz, 6H), 0.81 (s, 9H), 1.81-8.92 (m, 4H), 1.93 (s, 3H), 2.14 (sep, J=6.8 Hz, 1H), 2.47 (t, J=7.0 Hz, 2H), 3.39 (s, 3H), 4.07-4.10 (m, 2H), 4.87 (s, 2H).

Step 2

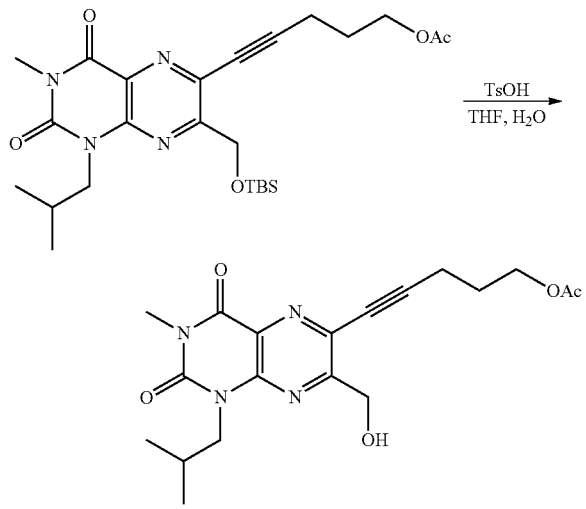

5-7-(hydroxymethyl)-1-isobutyl-3-methyl-2,4-dioxo-1,2,3,4-tetrahydropteridin-6-yl)pent-4-yn-1-yl acetate: A solution of 5-7-(((tert-butyldimethylsilyl)oxy)methyl)-1-isobutyl-3-methyl-2,4-dioxo-1,2,3,4-tetrahydropteridin-6-yl)pent-4-yn-1-ylacetate (1.485 g, 2.95 mmol) in THF (100 mL) was treated with a solution of TsOH (0.45 g, 2.36 mmol) in H$_2$O (20 mL). The reaction was stirred at room temperature for 24 hours. The reaction was diluted with EA, washed with brine, dried over Na$_2$SO$_4$. The solvent was removed and the residue was purified by column (Hex:EA=2:1) to afford 924 mg (81%) of 5-7-(hydroxymethyl)-1-isobutyl-3-methyl-2,4-dioxo-1,2,3,4-tetrahydropteridin-6-yl)pent-4-yn-1-yl acetate as a pink solid. R$_f$=0.25 (Hex:EA=1:1); LC-MS (ESI): m/z 389 [M+1]$^+$. $^1$H NMR (400 MHz, CDCl$_3$) δ (ppm) 0.97 (d, J=6.8 Hz, 6H), 1.99-2.03 (m, 2H), 2.10 (s, 3H), 2.27 (sep, J=6.8 Hz, 1H), 2.64 (t, J=7.2 Hz, 2H), 3.56 (s, 3H), 4.21-4.26 (m, 4H), 5.00 (d, J=4.8 Hz, 2H); $^{13}$C NMR (100 MHz, CDCl$_3$) δ (ppm) 20.2, 21.0, 25.9, 27.5, 28.0, 28.4, 29.1, 32.6, 49.5, 61.8, 64.2, 125.4, 145.5, 150.2, 150.6, 156.0, 160.0, 171.2.

Step 3 (Version 3A)

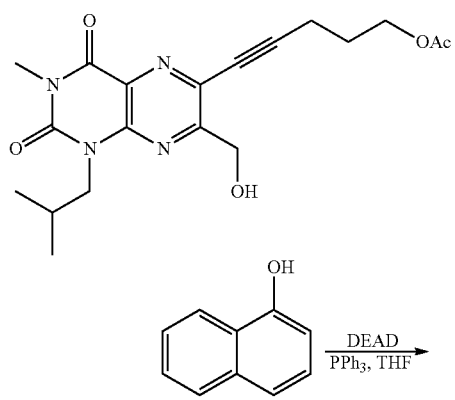

5-(1-isobutyl-3-methyl-7-((naphthalen-1-yloxy)methyl)-2,4-dioxo-1,2,3,4-tetrahydropteridin-6-yl)pent-4-yn-1-yl acetate: A mixture of 5-7-(hydroxymethyl)-1-isobutyl-3-methyl-2,4-dioxo-1,2,3,4-tetrahydropteridin-6-yl)pent-4-yn-1-ylacetate (165 mg, 0.425 mmol), naphthalen-1-ol (612 mg, 4.25 mmol), and PPh$_3$ (669 mg, 2.55 mmol) in THF (15 mL) was treated with DEAD (555 mg, 40% wt solution in toluene, 1.28 mmol). The reaction was stirred at room temperature for 24 hours. The reaction was diluted with EA, washed with brine, dried over Na$_2$SO$_4$. The solvent was removed and the residue was purified by column (Hex:EA=3:2) to afford 5-(1-isobutyl-3-methyl-7-((naphthalen-1-yloxy)methyl)-2,4-dioxo-1,2,3,4-tetrahydropteridin-6-yl)pent-4-yn-1-yl acetate as a yellow solid. R$_f$=0.40 (Hex:EA=1:1); LC-MS (ESI): m/z 515 [M+1]$^+$. $^1$H NMR (400 MHz, CDCl$_3$) δ (ppm) 0.64 (d, J=6.4 Hz, 6H), 1.85-1.97 (m, 3H), 2.06 (s, 3H), 2.55 (t, J=7.0 Hz, 2H), 3.52 (s, 3H), 3.94 (d, J=7.6 Hz, 2H), 4.15 (t, J=6.2 Hz, 2H), 5.64 (s, 2H), 6.80 (d, J=7.6 Hz, 1H), 7.31-7.54 (m, 4H), 7.81 (d, J=7.2 Hz, 1H), 8.35 (d, J=7.2 Hz, 1H).

Step 4 (Version 4A)

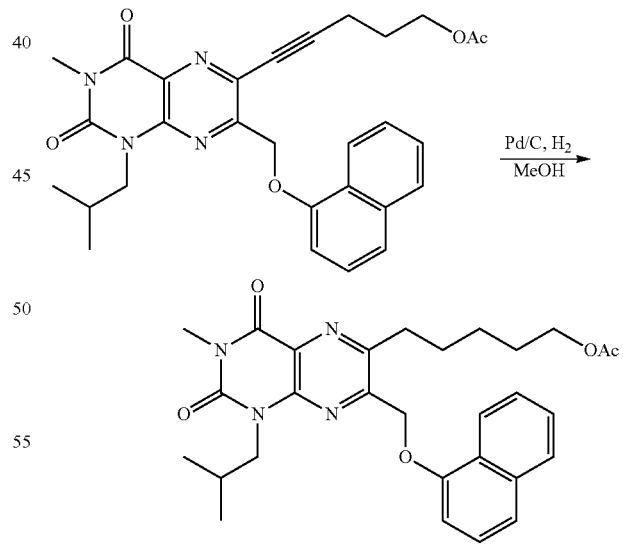

5-(1-isobutyl-3-methyl-7-((naphthalen-1-yloxy)methyl)-2,4-dioxo-1,2,3,4-tetrahydropteridin-6-yl)pentyl acetate: A mixture of 5-(1-isobutyl-3-methyl-7-((naphthalen-1-yloxy)methyl)-2,4-dioxo-1,2,3,4-tetrahydropteridin-6-yl)pent-4-yn-1-ylacetate (50 mg, 0.097 mmol) and Pd/C (30 mg, 10% on charcoal) in MeOH (10 mL) was stirred under H$_2$ (Parr hydrogenator, 50 psi) for 1 hour. The reaction was filtered.

The filtrate was concentrated and purified by column (Hex:EA=3:2) to afford 44 mg (87%) of 5-(1-isobutyl-3-methyl-7-((naphthalen-1-yloxy)methyl)-2,4-dioxo-1,2,3,4-tetrahydropteridin-6-yl)pentyl acetate as a yellow solid. $R_f$=0.40 (Hex:EA=1:1); LC-MS (ESI): m/z 519 [M+1]$^+$. $^1$H NMR (400 MHz, CDCl$_3$) δ (ppm) 0.84 (d, J=6.4 Hz, 6H), 1.46-1.51 (m, 2H), 1.60-1.69 (m, 2H), 1.85-1.91 (m, 2H), 2.03 (s, 3H), 2.14 (sep, J=6.8 Hz, 1H), 3.09 (t, J=7.2 Hz, 2H), 3.55 (s, 3H), 4.01 (t, J=6.4 Hz, 2H), 4.09 (d, J=7.6 Hz, 2H), 5.52 (s, 2H), 6.90 (d, J=7.6 Hz, 1H), 7.34-7.55 (m, 4H), 7.83 (d, J=7.2 Hz, 1H), 8.25 (d, J=8.0 Hz, 1H).

Step 5

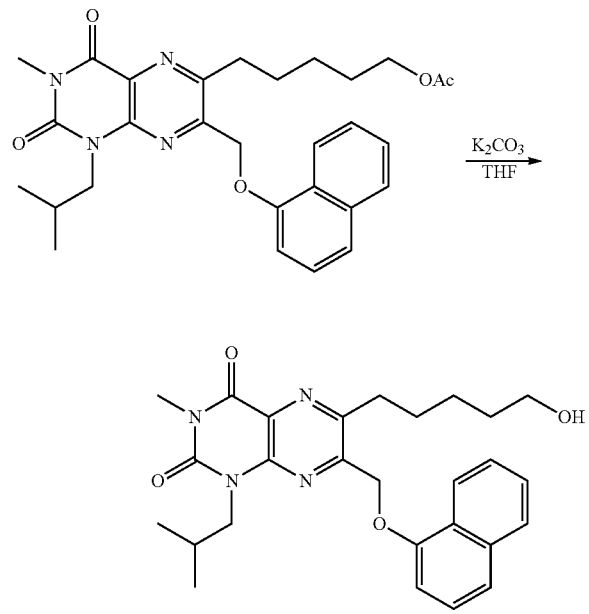

6-(5-hydroxypentyl)-1-isobutyl-3-methyl-7-((naphthalene-1-yloxy)methyl)pteridine-2,4(1H,3H)-dione: A solution of 5-(1-isobutyl-3-methyl-7-((naphthalen-1-yloxy)methyl)-2,4-dioxo-1,2,3,4-tetrahydropteridin-6-yl)pentyl acetate (8 mg, 0.015 mmol) in THF (3 mL) and MeOH (3 mL) was treated with K$_2$CO$_3$ (9 mg, 0.060 mmol). The reaction was stirred at room temperature for 2 hours. The reaction was diluted with EA, washed with brine, dried over Na$_2$SO$_4$. The filtrate was concentrated and purified by preparative HPLC to afford 4 mg of 6-(5-hydroxypentyl)-1-isobutyl-3-methyl-7-((naphthalene-1-yloxy)methyl)pteridine-2,4(1H,3H)-dione as a white solid. $R_f$=0.15 (Hex:EA=1:1); Single peak in analytical HPLC; LC-MS (ESI): m/z 477 [M+1]$^+$. $^1$H NMR (400 MHz, CDCl$_3$) δ (ppm) 0.73 (d, J=6.4 Hz, 6H), 1.39-1.48 (m, 4H), 1.80-1.91 (m, 2H), 2.04 (sep, J=6.8 Hz, 1H), 3.02 (t, J=7.2 Hz, 2H), 3.45 (s, 3H), 3.54 (t, J=6.4 Hz, 2H), 4.00 (d, J=7.2 Hz, 2H), 5.43 (s, 2H), 6.80 (d, J=7.6 Hz, 1H), 7.24-7.45 (m, 4H), 7.75 (d, J=7.6 Hz, 1H), 8.16 (d, J=7.6 Hz, 1H).

Example 3. 6-(5-hydroxypentyl)-1-isobutyl-7-((isoquinolin-5-yloxy)methyl)-3-methylpteridine-2,4(1H,3H)-dione

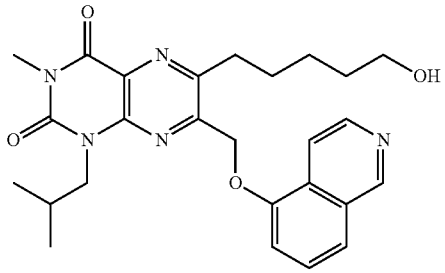

Prepared following the methods of Example 2, with the exception of the switching of steps 3 and 4, with reduction (step 3B) preceding Mitsunobu reaction with 5-hydroxyisoquinoline (step 4B), which was followed by acetate removal (step 5) under conditions of KCN/95% ethanol.

Steps 1-2: As in Example 2

Step 3B as in Step 4 of Example 2

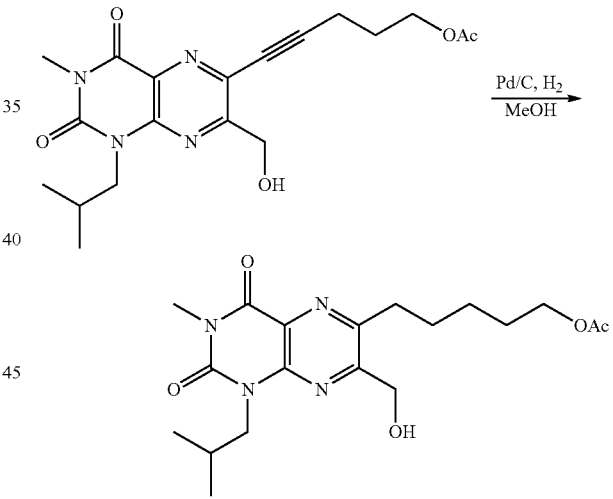

5-(7-(hydroxymethyl)-1-isobutyl-3-methyl-2,4-dioxo-1,2,3,4-tetrahydropteridin-6-yl)pentyl acetate: A mixture of 5-7-(hydroxymethyl)-1-isobutyl-3-methyl-2,4-dioxo-1,2,3,4-tetrahydropteridin-6-yl)pent-4-yn-1-ylacetate (1.218 g, 3.14 mmol) and Pd/C (340 mg, 10% on charcoal) in THF (14 mL) and MeOH (70 mL) was stirred under H$_2$ (Parr hydrogenator, 50 psi) for 3 hours. The reaction was filtered. The filtrate was concentrated and purified by column (Hex:EA=3:2) to afford 789 mg (64%) of 5-(7-(hydroxymethyl)-1-isobutyl-3-methyl-2,4-dioxo-1,2,3,4-tetrahydropteridin-6-yl)pentyl acetate as a yellow solid. $R_f$=0.15 (Hex:EA=1:1); LC-MS (ESI): m/z 393 [M+1]$^+$. $^1$H NMR (400 MHz, CDCl$_3$) δ (ppm) 0.94 (d, J=6.8 Hz, 6H), 1.46-1.51 (m, 2H), 1.64-1.72 (m, 2H), 1.76-1.84 (m, 2H), 2.05 (s, 3H), 2.25 (sep, J=6.8 Hz, 1H), 2.84 (t, J=8.0 Hz, 2H), 3.54 (s, 3H), 4.06 (t, J=6.6 Hz, 2H), 4.018 (d, J=7.6 Hz, 2H), 4.91 (s, 2H).

Step 4B, as in Step 3 of Example 2, with Slightly Modified Mitsunobu Conditions

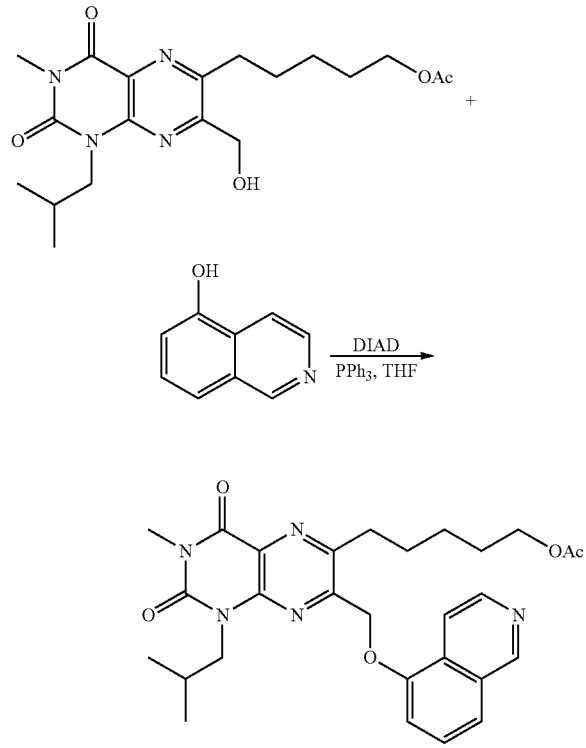

5-(1-isobutyl-7-((isoquinolin-5-yloxy)methyl)-3-methyl-2,4-dioxo-1,2,3,4-tetrahydropteridin-6-yl)pentyl acetate: A mixture of 5-(7-(hydroxymethyl)-1-isobutyl-3-methyl-2,4-dioxo-1,2,3,4-tetrahydropteridin-6-yl)pentyl acetate (981 mg, 2.50 mmol), 5-hydroxyisoquinoline (435 mg, 3.00 mmol), and PPh₃ (918 mg, 3.50 mmol) in THF (100 mL) was treated with DIAD (708 mg, 3.50 mmol). The reaction was stirred at room temperature for 24 hours. The reaction was diluted with EA, washed with brine, and dried over Na₂SO₄. The solvent was removed and the residue was purified by column (Hex:EA=2:3) to afford 1.071 g (82%) of 5-(1-isobutyl-7-((isoquinolin-5-yloxy)methyl)-3-methyl-2,4-dioxo-1,2,3,4-tetrahydropteridin-6-yl)pentyl acetate as a white solid. $R_f$=0.20 (EA); LC-MS (ESI): m/z 520 [M+1]⁺.

Step 5

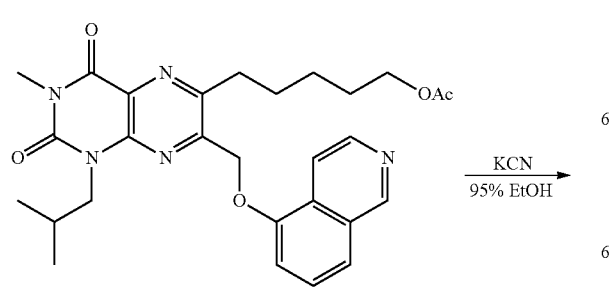

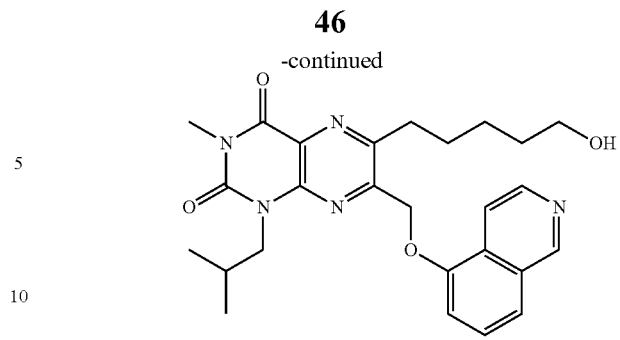

6-(5-hydroxypentyl-1-isobutyl-3-methyl-7-((isoquinolin-5-yloxy)methyl)pteridine-2,4-(1H,3H)-dione: A solution of 5-(1-isobutyl-3-methyl-2,4-dioxo-7-((isoquinolin-5-yloxy)methyl)-1,2,3,4-tetrahydropteridin-6-yl)pentyl acetate (790 mg, 1.52 mmol) in 95% EtOH (100 mL) was treated with KCN (800 mg). The reaction was stirred at room temperature for 40 hours. The reaction was concentrated and purified by preparative HPLC to afford 326 mg (45%) of 6-(5-hydroxypentyl-1-isobutyl-3-methyl-7-((isoquinolin-5-yloxy)methyl)pteridine-2,4-(1H,3H)-dione as white solid (TFA salt). Single peak in analytical HPLC; LC-MS (ESI): m/z 478 [M+1]⁺. ¹H NMR (400 MHz, CDCl₃) δ (ppm) 0.79 (d, J=6.8 Hz, 6H), 1.49-1.62 (m, 4H), 1.88-1.93 (m, 2H), 2.08 (sep, J=6.8 Hz, 1H), 3.10 (t, J=7.6 Hz, 2H), 3.54 (s, 3H), 3.66 (t, J=6.2 Hz, 2H), 4.06 (d, J=7.6 Hz, 2H), 5.54 (s, 2H), 6.95 (d, J=7.6 Hz, 1H), 7.42-7.45 (m, 1H), 7.60 (t, J=8.2 Hz, 1H), 7.77 (d, J=8.4 Hz, 1H), 8.60 (d, J=8.4 Hz, 1H), 8.95 (s, 1H).

Example 4. 6-(5-hydroxypentyl)-1-isobutyl-7-((isoquinolin-4-yloxy)methyl)-3-methylpteridine-2,4(1H,3H)-dione

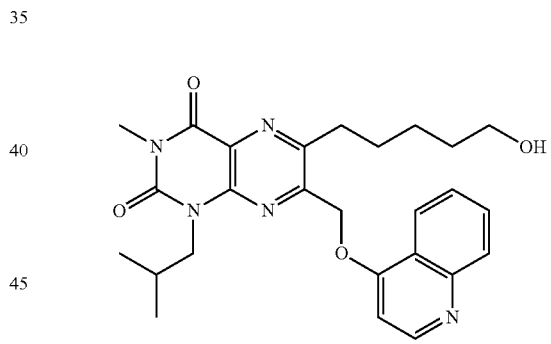

Step 4B Product, 5-(1-isobutyl-3-methyl-2,4-dioxo-7-((quinolin-4-yloxy)methyl)-1,2,3,4-tetrahydropteridin-6-yl)pentyl acetate

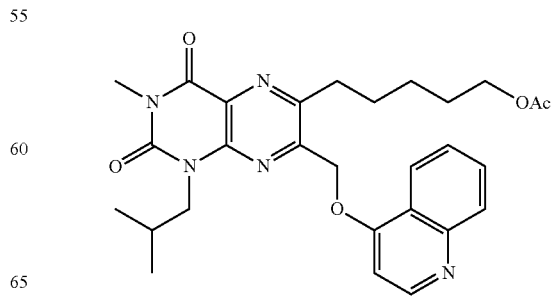

White solid. $R_f$=0.20 (EA); LC-MS (ESI): m/z 520 [M+1]$^+$. $^1$H NMR (400 MHz, CDCl$_3$) δ (ppm) 0.63 (d, J=6.0 Hz, 6H), 1.40-1.50 (m, 2H), 1.55-1.64 (m, 2H), 1.79-1.90 (m, 3H), 1.90 (s, 3H), 2.99 (s, 2H), 3.46 (s, 3H), 3.85 (d, J=6.0 Hz, 2H), 3.98 (s, 2H), 5.76 (s, 2H), 7.30 (s, 1H), 7.73-7.77 (m, 1H), 7.95-7.98 (m, 1H), 8.31 (d, J=8.0 Hz, 1H), 8.42 (d, J=8.8 Hz, 1H), 9.10 (s, 1H).

Step 5 (final) product, 6-(5-hydroxypentyl-1-isobutyl-3-methyl-7-((quinolin-4-yloxy)methyl)pteridine-2,4-(1H,3H)-dione (acetate removal conditions: K$_2$CO$_3$, THF, room temperature, 1 h): White solid (TFA salt). Single peak in analytical HPLC; LC-MS (ESI): m/z 478 [M+1]$^+$ $^1$H NMR (400 MHz, CDCl$_3$) δ (ppm) 0.60 (d, J=6.8 Hz, 6H), 1.40-1.60 (m, 4H), 1.80-1.89 (m, 2H), 1.92 (sep, J=6.8 Hz, 1H), 2.98 (s, 2H), 3.44 (s, 3H), 3.58 (s, 2H), 3.83 (d, J=7.6 Hz, 2H), 5.79 (s, 2H), 7.28 (s, 1H), 7.72-7.76 (m, 1H), 7.93-7.97 (m, 1H), 8.31-8.33 (m, 2H) 9.08 (s, 1H).

Example 5. 6-(5-hydroxypentyl-1-isobutyl-7-((isoquinolin-4-yloxy)methyl)-3-methyl-pteridine-2,4-(1H,3H)-dione

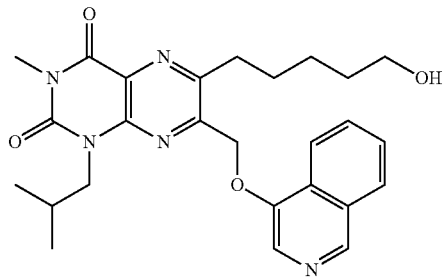 [SMILES: CC(C)Cn1c(=O)n(C)c(=O)c2nc(CCCCCO)c(COc3cncc4ccccc34)nc21]

Follows Example 3 using the appropriate heteroaryl alcohol in the Mitsunobu step. Step 4B product, 5-(1-isobutyl-7-((isoquinolin-4-yloxy)methyl)-3-methyl-2,4-dioxo-1,2,3,4-tetrahydropteridin-6-yl)pentyl acetate:

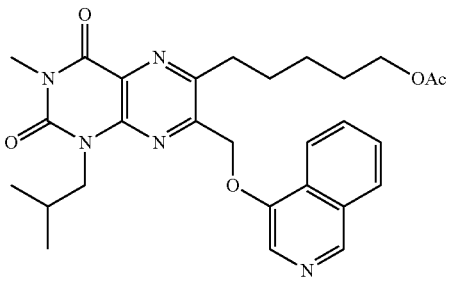 [SMILES: CC(=O)OCCCCCc1nc2c(=O)n(C)c(=O)n(CC(C)C)c2nc1COc1cncc2ccccc12]

Yellow solid. $R_f$=0.10 (Hex:EA=1:1); LC-MS (ESI): m/z 520 [M+1]$^+$.

Step 5 (final) product 6-(5-hydroxypentyl-1-isobutyl-7-((isoquinolin-4-yloxy)methyl)-3-methyl-pteridine-2,4-(1H, 3H)-dione: white solid (TFA salt). Single peak in analytical HPLC; LC-MS (ESI): m/z 478 [M+1]$^+$. $^1$H NMR (400 MHz, CD$_3$OD) δ (ppm) 0.48 (d, J=6.8 Hz, 6H), 1.42-1.51 (m, 4H), 1.75-1.88 (m, 3H), 2.97 (t, J=7.8 Hz, 2H), 3.62 (s, 3H), 3.45 (t, J=6.4 Hz, 2H), 3.76 (d, J=7.6 Hz, 2H), 5.81 (s, 2H), 7.90-7.95 (m, 1H), 8.04-8.08 (m, 1H), 8.21 (s, 1H), 8.32 (d, J=8.4 Hz, 1H), 8.43 (d, J=8.4 Hz, 1H), 9.23 (s, 1H).

Example 6. 7-(((1H-indol-4-yl)oxy)methyl)-6-(5-hydroxypentyl)-1-isobutyl-3-methylpteridine-2,4(1H,3H)-dione

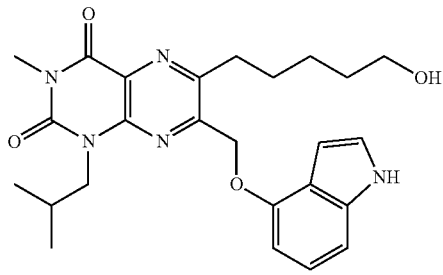 [SMILES: CC(C)Cn1c(=O)n(C)c(=O)c2nc(CCCCCO)c(COc3cccc4[nH]ccc34)nc21]

Follows Example 3 using the appropriate heteroaryl alcohol in the Mitsunobu step. Step 4B product, 5-(7-(((1H-indol-4-yl)oxy)methyl)-1-isobutyl-3-methyl-2,4-dioxo-1,2,3,4-tetrahydropteridin-6-yl)pentyl acetate:

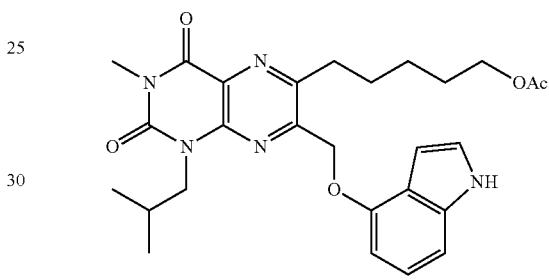

colorless oil. $R_f$=0.30 (Hex:EA=1:1); LC-MS (ESI): m/z 508 [M+1]$^+$.

Step 5 (final) product 7-(((1H-indol-4-yl)oxy)methyl)-6-(5-hydroxypentyl)-1-isobutyl-3-methylpteridine-2,4-(1H,3H)-dione: brown solid (TFA salt). Single peak in analytical HPLC; LC-MS (ESI): m/z 466 [M+1]$^+$. $^1$H NMR (400 MHz, CD$_3$OD) δ (ppm) 0.68 (d, J=6.8 Hz, 6H), 1.36-1.45 (m, 4H), 1.72-1.77 (m, 2H), 1.96 (sep, J=6.8 Hz, 1H), 2.97 (t, J=8.0 Hz, 2H), 3.36 (s, 3H), 3.41 (t, J=6.4 Hz, 2H), 3.93 (d, J=7.6 Hz, 2H), 5.43 (s, 2H), 6.39-6.43 (m, 2H), 6.84-7.03 (m, 3H); $^{13}$C NMR (100 MHz, CDCl$_3$) δ (ppm) 19.9, 25.4, 27.2, 28.4, 29.0, 32.3, 33.4, 49.3, 62.4, 68.8, 99.8, 100.8, 105.3, 118.7, 122.5, 123.1, 125.9, 137.5, 145.7, 150.7, 151.6, 152.9, 153.8, 160.4.

Example 7. 6-(5-hydroxypentyl)-1-isobutyl-3-methyl-7-((2-(trifluoromethyl)phenoxy)methyl)pteridine-2,4(1H,3H)-dione

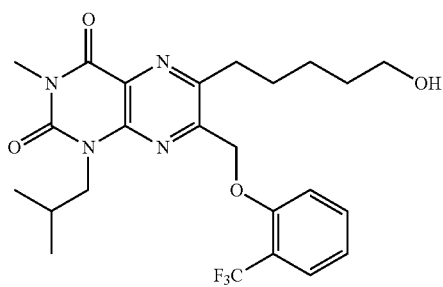 [SMILES: CC(C)Cn1c(=O)n(C)c(=O)c2nc(CCCCCO)c(COc3ccccc3C(F)(F)F)nc21]

Follows Example 3 using the appropriate heteroaryl alcohol in the Mitsunobu step. Step 4B product, 5-(1-isobutyl-3-methyl-2,4-dioxo-7-((2-trifluoromethyl)phenoxy)methyl)-1,2,3,4-tetrahydropteridin-6-yl)pentyl acetate:

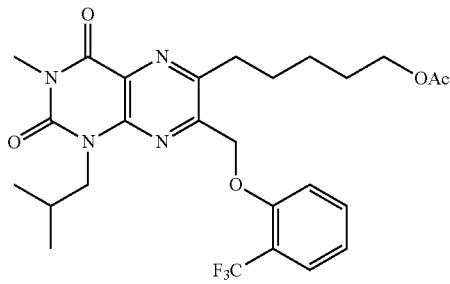 [SMILES: CC(=O)OCCCCCc1nc2c(=O)n(C)c(=O)n(CC(C)C)c2nc1COc1ccccc1C(F)(F)F]

Colorless oil. $R_f$=0.40 (Hex:EA=1:1); LC-MS (ESI): m/z 537 [M+1]$^+$.

Step 5 (final) product 6-(5-hydroxypentyl)-1-isobutyl-3-methyl-7-((2-(trifluoromethyl)phenoxy)methyl)pteridine-2,4-(1H,3H)-dione: white solid. Single peak in analytical HPLC; LC-MS (ESI): m/z 495 [M+1]$^+$. $^1$H NMR (400 MHz, CDCl$_3$) δ (ppm) 0.84 (d, J=6.8 Hz, 6H), 1.50-1.70 (m, 4H), 1.85-1.93 (m, 2H), 2.07 (sep, J=6.8 Hz, 1H), 3.06 (t, J=7.6 Hz, 2H), 3.53 (s, 3H), 3.70 (t, J=5.6 Hz, 2H), 4.08 (d, J=7.6 Hz, 2H), 5.43 (s, 2H), 7.03-7.10 (m, 2H), 7.43 (dt, J=1.2, 7.8 Hz, 1H), 7.63 (dd, J=1.2, 7.6 Hz, 1H); $^{19}$F NMR (400 MHz, CDCl$_3$) δ (ppm) −62.1; $^{13}$C NMR (100 MHz, CDCl$_3$) δ (ppm) 19.8, 25.4, 27.0, 27.8, 29.0, 32.2, 33.0, 49.2, 62.3, 68.6, 112.9, 119.0, 121.0, 122.1, 124.8, 126.1, 127.5, 133.2, 145.8, 150.6, 152.2, 155.8, 160.2.

Example 8. 6-(5-hydroxypentyl)-1-isobutyl-3-methyl-7-(((4-nitronaphthalen-1-yl)oxy)methyl)pteridine-2,4(1H,3H)-dione

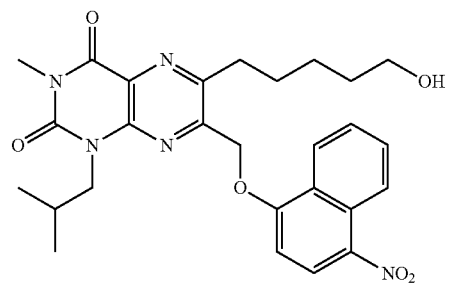

Follows Example 3 using the appropriate heteroaryl alcohol in the Mitsunobu step. Step 4B product, 5-(1-isobutyl-3-methyl-7-(((4-nitronaphthalen-1-yl)oxy)methyl)-2,4-dioxo-1,2,3,4-tetrahydropteridin-6-yl)pentyl acetate:

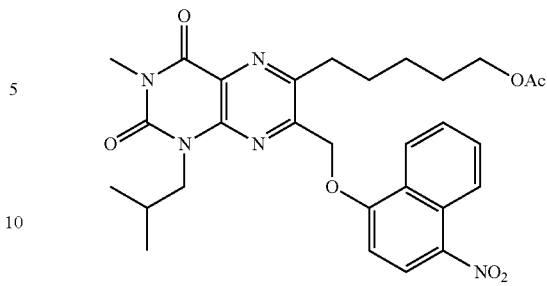

Yellow solid. $R_f$=0.20 (Hex:EA=1:1); LC-MS (ESI): m/z 564 [M+1]$^+$. (400 MHz, CDCl$_3$) δ (ppm) 0.77 (d, J=6.8 Hz, 6H), 1.45-1.54 (m, 2H), 1.60-1.70 (m, 2H), 1.83-1.92 (m, 2H), 2.04 (s, 3H), 2.08 (sep, J=6.4 Hz, 1H), 3.08 (t, J=8.0 Hz, 2H), 3.54 (s, 3H), 4.02-4.05 (m, 4H), 5.65 (s, 2H), 6.93 (d, J=8.4 Hz, 1H), 7.62-7.66 (m, 1H), 7.77-7.81 (m, 1H), 8.34 (d, J=8.8 Hz, 1H), 8.40 (d, J=8.0 Hz, 1H), 8.77 (d, J=8.8 Hz, 1H).

Step 5 (final) product 6-(5-hydroxypentyl)-1-isobutyl-3-methyl-7-(((4-nitronaphthalen-1-yl)oxy)methylpteridine-2,4-(1H,3H)-dione (acetate removal conditions: K$_2$CO$_3$, MeOH, room temperature, 1 h): yellow solid. >95% purity in analytical HPLC; LC-MS (ESI): m/z 492 [M+1]$^+$. $^1$H NMR (400 MHz, CDCl$_3$) δ (ppm) 0.67 (d, J=6.8 Hz, 6H), 1.40-1.54 (m, 4H), 1.75-1.86 (m, 2H), 1.97 (sep, J=6.4 Hz, 1H), 3.00 (t, J=7.6 Hz, 2H), 3.45 (s, 3H), 3.57 (t, J=6.2 Hz, 2H), 3.93 (d, J=7.2 Hz, 2H), 5.55 (s, 2H), 6.82 (d, J=8.8 Hz, 1H), 7.53-7.57 (m, 1H), 7.68-7.72 (m, 1H), 8.26 (d, J=8.8 Hz, 1H), 8.32 (d, J=8.4 Hz, 1H), 8.69 (d, J=8.8 Hz, 1H).

Example 9. 7-(((4-aminonaphthalen-1-yl)oxy)methyl)-6-(5-hydroxypentyl)-1-isobutyl-3-methylpteridine-2,4(1H,3H)-dione

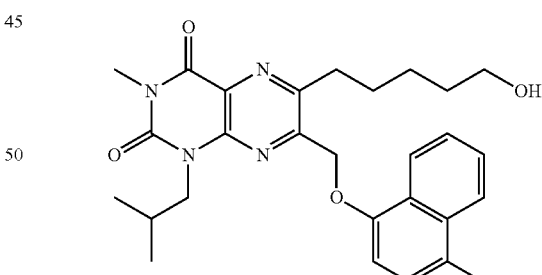

Prepared from the product of Example 8 by catalytic hydrogenation using Pd/C. Data: light brown solid (TFA salt). Single peak in analytical HPLC; LC-MS (ESI): m/z 522 [M+1]$^+$. $^1$H NMR (400 MHz, CDCl$_3$) δ (ppm) 0.60 (d, J=6.8 Hz, 6H), 1.36-1.46 (m, 4H), 1.72-1.85 (m, 2H), 1.93 (sep, J=6.4 Hz, 1H), 2.97 (t, J=7.8 Hz, 2H), 3.77 (s, 3H), 3.42 (t, J=6.4 Hz, 2H), 3.87 (d, J=7.6 Hz, 2H), 5.56 (s, 2H), 6.86 (d, J=8.0 Hz, 1H), 7.09 (d, J=8.0 Hz, 1H), 7.50-7.59 (m, 2H), 7.84 (d, J=8.4 Hz, 1H), 8.27 (d, J=8.4 Hz, 1H).

Example 10. 6-(5-hydroxypentyl)-1-isobutyl-3-methyl-7-((naphthalen-2-yloxy)methyl)pteridine-2,4(1H,3H)-dione

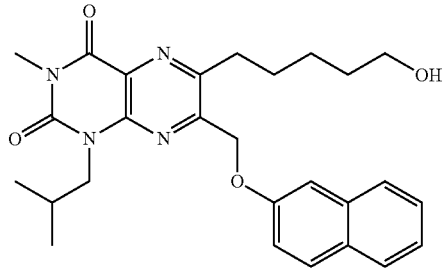

Follows Example 3 using the appropriate heteroaryl alcohol in the Mitsunobu step. Step 4B product, 5-(1-isobutyl-3-methyl-7-((naphthalen-2-yloxy)methyl)-2,4-dioxox-1,2,3,4-tetrahydropteridin-6-yl)pentyl acetate:

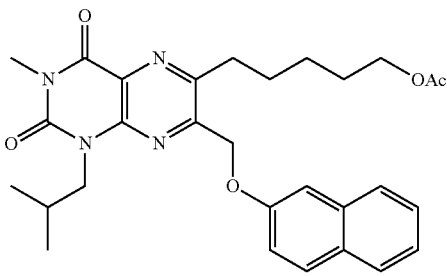 [SMILES: CC(=O)OCCCCCc1nc2c(=O)n(C)c(=O)n(CC(C)C)c2nc1COc1ccc2ccccc2c1]

Yellow solid. R_f=0.50 (Hex:EA=1:1); LC-MS (ESI): m/z 519 [M+1]+.

Step 5 (final) product 6-(5-hydroxypentyl)-1-isobutyl-3-methyl-7-((naphthalene-2-yloxy)methyl)pteridine-2,4-(1H,3H)-dione (acetate removal conditions: K_2CO_3, MeOH, room temperature, 1 h): white solid. Single peak in analytical HPLC; LC-MS (ESI): m/z 477 [M+1]+. $^1$H NMR (400 MHz, CDCl_3) δ (ppm) 0.89 (d, J=6.4 Hz, 6H), 1.52-1.67 (m, 4H), 1.88-1.94 (m, 2H), 2.18 (sep, J=6.4 Hz, 1H), 3.10 (t, J=7.6 Hz, 2H), 3.55 (s, 3H), 3.69 (t, J=6.2 Hz, 2H), 4.13 (d, J=7.6 Hz, 2H), 5.45 (s, 2H), 7.20-7.24 (m 2H), 7.37-7.50 (m, 2H), 7.71 (d, J=8.4 Hz, 1H), 7.80 (d, J=8.8 Hz, 1H).

Example 11. 7-((2-bromophenoxy)methyl)-6-(5-hydroxypentyl)-1-isobutyl-3-methylpteridine-2,4(1H,3H)-dione

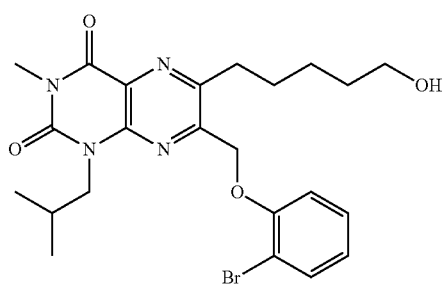

Follows Example 3 using the appropriate heteroaryl alcohol in the Mitsunobu step. Step 4B product, 5-(7-((2-bromophenoxy)methyl)-1-isobutyl-3-methyl-2,4-dioxo-1,2,3,4-tetrahydropteridin-6-yl)pentyl acetate:

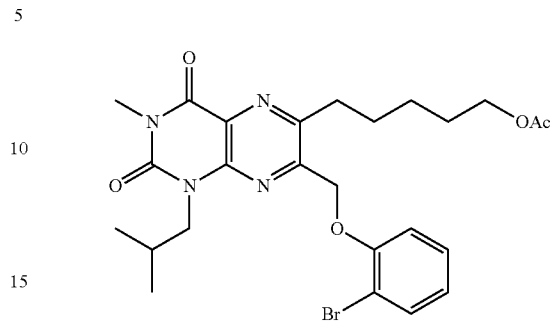

Colorless oil. R_f=0.50 (Hex:EA=1:1); LC-MS (ESI): m/z 547 [M+1]+.

Step 5 (final) product 7-((2-bromophenoxy)methyl)-6-(5-hydroxypentyl)-1-isobutyl-3-methylpteridine-2,4-(1H,3H)-dione: white solid. >98% purity in analytical HPLC; LC-MS (ESI): m/z 505 [M+1]+. $^1$H NMR (400 MHz, CDCl_3) δ (ppm) 0.86 (d, J=6.8 Hz, 6H), 1.48-1.69 (m, 4H), 1.83-1.95 (m, 2H), 2.09 (sep, J=6.8 Hz, 1H), 3.08 (t, J=7.6 Hz, 2H), 3.51 (s, 3H), 3.67 (t, J=6.2 Hz, 2H), 4.05 (d, J=7.6 Hz, 2H), 5.40 (s, 2H), 6.87 (dt, J=1.2, 7.8 Hz, 1H), 6.92 (dd, J=1.2, 8.0 Hz, 1H), 7.19-7.23 (m, 1H), 7.55 (dd, J=1.6, 8.0 Hz, 1H); $^{13}$C NMR (100 MHz, CDCl_3) δ (ppm) 19.9, 25.5, 27.1, 28.1, 29.0, 32.3, 33.3, 49.3, 62.3, 69.1, 112.1, 113.5, 122.8, 126.0, 128.4, 133.8, 145.7, 150.6, 152.4, 152.6, 154.3, 160.2.

Example 12. 6-(5-hydroxypentyl)-1-isobutyl-3-methyl-7-((quinolin-4-yloxy)methyl)pteridine-2,4(1H,3H)-dione

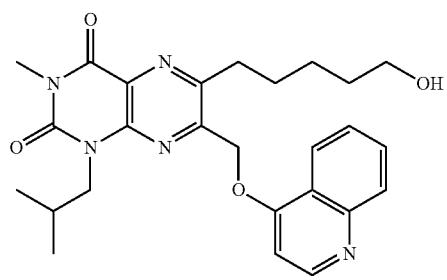

Follows Example 3 using the appropriate heteroaryl alcohol in the Mitsunobu step. Step 4B product, 5-(1-isobutyl-3-methyl-2,4-dioxo-7-((quinolin-4-yloxy)methyl)-1,2,3,4-tetrahydropteridin-6-yl)pentyl acetate:

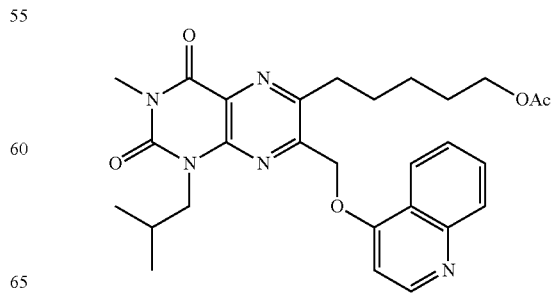

White solid. $R_f$=0.20 (EA); LC-MS (ESI): m/z 520 [M+1]$^+$. $^1$H NMR (400 MHz, CDCl$_3$) δ (ppm) 0.63 (d, J=6.0 Hz, 6H), 1.40-1.50 (m, 2H), 1.55-1.64 (m, 2H), 1.79-1.90 (m, 3H), 1.90 (s, 3H), 2.99 (s, 2H), 3.46 (s, 3H), 3.85 (d, J=6.0 Hz, 2H), 3.98 (s, 2H), 5.76 (s, 2H), 7.30 (s, 1H), 7.73-7.77 (m, 1H), 7.95-7.98 (m, 1H), 8.31 (d, J=8.0 Hz, 1H), 8.42 (d, J=8.8 Hz, 1H), 9.10 (s, 1H).

Step 5 (final) product 6-(5-hydroxypentyl)-1-isobutyl-3-methyl-7-((quinolin-4-yloxy)methyl)pteridine-2,4(1H,3H)-dione (acetate removal conditions: K$_2$CO$_3$, MeOH, room temperature, 1 h): white solid (TFA salt). Single peak in analytical HPLC; LC-MS (ESI): m/z 478 [M+1]$^+$. $^1$H NMR (400 MHz, CDCl$_3$) δ (ppm) 0.60 (d, J=6.8 Hz, 6H), 1.40-1.60 (m, 4H), 1.80-1.89 (m, 2H), 1.92 (sep, J=6.8 Hz, 1H), 2.98 (s, 2H), 3.44 (s, 3H), 3.58 (s, 2H), 3.83 (d, J=7.6 Hz, 2H), 5.79 (s, 2H), 7.28 (s, 1H), 7.72-7.76 (m, 1H), 7.93-7.97 (m, 1H), 8.31-8.33 (m, 2H) 9.08 (s, 1H).

Example 13. 7-((2-chlorophenoxy)methyl)-6-(5-hydroxypentyl)-1-isobutyl-3-methylpteridine-2,4 (1H,3H)-dione

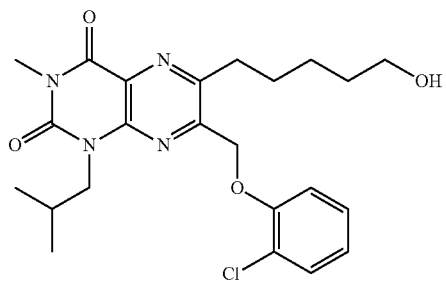

Follows Example 3 using the appropriate heteroaryl alcohol in the Mitsunobu step. Step 4B product, 5-(7-((2-chlorophenoxy)methyl)-1-isobutyl-3-methyl-2,4-dioxo-1,2,3,4-tetrahydropteridin-6-yl)pentyl acetate:

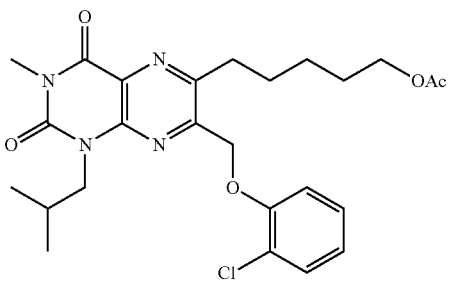 [SMILES: CC(=O)OCCCCCc1nc2c(=O)n(C)c(=O)n(CC(C)C)c2nc1COc1ccccc1Cl]

Colorless oil. $R_f$=0.40 (Hex:EA=1:1); LC-MS (ESI): m/z 503 [M+1]$^+$.

Step 5 (final) product 7-((2-chlorophenoxy)methyl)-6-(5-hydroxypentyl)-1-isobutyl-3-methylpteridine-2,4-(1H,3H)-dione: white solid. >98% purity in analytical HPLC; LC-MS (ESI): m/z 461 [M+1]$^+$. $^1$H NMR (400 MHz, CDCl$_3$) δ (ppm) 0.78 (d, J=6.8 Hz, 6H), 1.40-1.60 (m, 4H), 1.75-1.90 (m, 2H), 2.00 (sep, J=6.8 Hz, 1H), 3.00 (t, J=7.6 Hz, 2H), 3.43 (s, 3H), 3.60 (t, J=5.8 Hz, 2H), 3.98 (d, J=7.6 Hz, 2H), 5.32 (s, 2H), 6.83-6.88 (m, 2H), 7.06-7.11 (m, 1H), 7.29-7.32 (m, 1H); $^{13}$C NMR (100 MHz, CDCl$_3$) δ (ppm) 19.9, 25.5, 27.1, 28.1, 29.0, 32.3, 33.4, 49.3, 62.4, 69.1, 113.7, 122.4, 123.0, 126.0, 127.6, 130.7, 145.7, 150.6, 152.4, 152.6, 153.4, 160.3.

Example 14. 7-(([1,1'-biphenyl]-4-yloxy)methyl)-6-(5-hydroxypentyl)-1-isobutyl-3-methylpteridine-2,4 (1H,3H)-dione

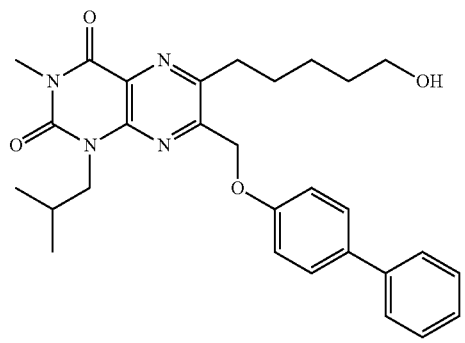 [SMILES: CC(C)Cn1c(=O)n(C)c(=O)c2nc(CCCCCO)c(COc3ccc(-c4ccccc4)cc3)nc21]

Follows Example 3 using the appropriate heteroaryl alcohol in the Mitsunobu step. Step 4B product, 5-(7-(([1,1'-biphenyl]-4-yloxy)methyl)-1-isobutyl-3-methyl-2,4-dioxo-1,2,3,4-tetrahydropteridin-6-yl)pentyl acetate:

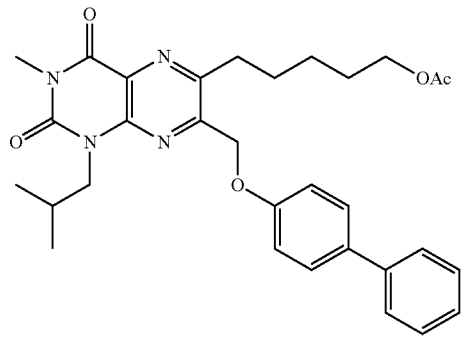 [SMILES: CC(=O)OCCCCCc1nc2c(=O)n(C)c(=O)n(CC(C)C)c2nc1COc1ccc(-c2ccccc2)cc1]

Colorless oil. $R_f$=0.50 (Hex:EA=1:1); LC-MS (ESI): m/z 545 [M+1]$^+$.

Step 5 (final) product 7-(([1,1'-biphenyl]-4-yloxy)methyl)-6-(5-hydroxypentyl)-1-isobutyl-3-methylpteridine-2,4-(1H,3H)-dione: white solid. Single peak in analytical HPLC; LC-MS (ESI): m/z 503 [M+1]$^+$. $^1$H NMR (400 MHz, CDCl$_3$) δ (ppm) 0.80 (d, J=6.8 Hz, 6H), 1.40-1.60 (m, 4H), 1.78-1.90 (m, 2H), 2.07 (sep, J=6.8 Hz, 1H), 2.98 (t, J=7.6 Hz, 2H), 3.45 (s, 3H), 3.61 (t, J=6.4 Hz, 2H), 4.02 (d, J=7.6 Hz, 2H), 5.27 (s, 2H), 6.95 (dd, J=2.0, 6.4 Hz, 2H), 7.22-7.26 (m, 1H), 7.32-7.36 (m, 2H), 7.43-7.46 (m, 4H).

Example 15. 6-(5-hydroxypentyl)-1-isobutyl-3-methyl-7-(phenoxymethyl)pteridine-2,4(1H, 3H)-dione

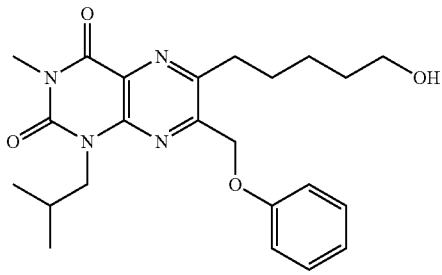 [SMILES: CC(C)Cn1c(=O)n(C)c(=O)c2nc(CCCCCO)c(COc3ccccc3)nc21]

Follows Example 3 using the appropriate heteroaryl alcohol in the Mitsunobu step. Step 4B product, 5-(1-isobutyl-3-methyl-2,4-dioxo-7-(phenoxymethyl)-1,2,3,4-tetrahydropteridin-6-yl)pentyl acetate:

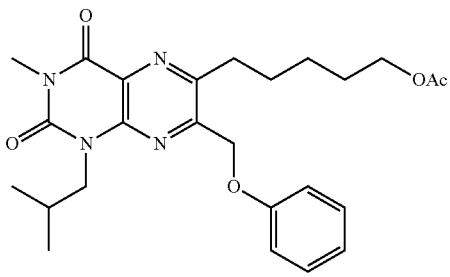

Colorless oil. $R_f$=0.30 (Hex:EA=1:1); LC-MS (ESI): m/z 469 [M+1]$^+$.

Step 5 (final) product 6-(5-hydroxypentyl)-1-isobutyl-3-methyl-7-(phenoxymethyl)pteridine-2,4-(1H,3H)-dione: white solid. Single peak in analytical HPLC; LC-MS (ESI): m/z 427 [M+1]$^+$. $^1$H NMR (400 MHz, CDCl$_3$) δ (ppm) 0.90 (d, J=6.8 Hz, 6H), 1.50-1.66 (m, 4H), 1.88-1.96 (m, 2H), 2.16 (sep, J=6.4 Hz, 1H), 3.06 (t, J=7.6 Hz, 2H), 3.54 (s, 3H), 3.69 (t, J=6.2 Hz, 2H), 4.11 (d, J=7.6 Hz, 2H), 5.32 (s, 2H), 6.97-7.04 (m, 3H), 7.29-7.34 (m, 2H).

Example 16. 6-(5-hydroxypentyl)-1-isobutyl-3-methyl-7-((3-(trifluoromethyl)phenoxy)methyl)pteridine-2,4(1H,3H)-dione

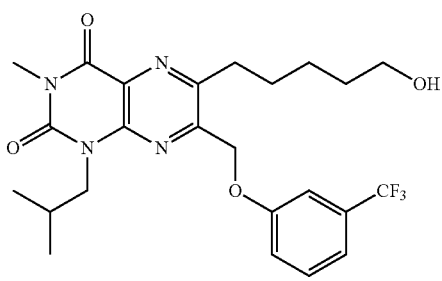

Follows Example 3 using the appropriate heteroaryl alcohol in the Mitsunobu step. Step 4B product, 5-(1-isobutyl-3-methyl-2,4-dioxo-7-((3-trifluoromethyl)phenoxy)methyl)-1,2,3,4-tetrahydropteridin-6-yl)pentyl acetate:

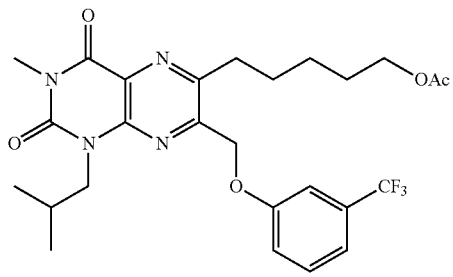 [SMILES: CC(=O)OCCCCCc1nc2c(=O)n(C)c(=O)n(CC(C)C)c2nc1COc1cccc(C(F)(F)F)c1]

Colorless oil. $R_f$=0.40 (Hex:EA=1:1); LC-MS (ESI): m/z 537 [M+1]$^+$.

Step 5 (final) product 6-(5-hydroxypentyl)-1-isobutyl-3-methyl-7-((3-(trifluoromethyl)phenoxy)methyl)pteridine-2,4-(1H,3H)-dione: white solid. >98% purity in analytical HPLC; LC-MS (ESI): m/z 495 [M+1]$^+$. $^1$H NMR (400 MHz, CDCl$_3$) δ (ppm) 0.87 (d, J=6.8 Hz, 6H), 1.50-1.70 (m, 4H), 1.83-1.95 (m, 2H), 2.14 (sep, J=6.8 Hz, 1H), 3.05 (t, J=7.6 Hz, 2H), 3.53 (s, 3H), 3.70 (t, J=5.8 Hz, 2H), 4.08 (d, J=7.6 Hz, 2H), 5.37 (s, 2H), 7.14 (dd, J=2.4, 8.4 Hz, 1H), 7.23-7.29 (m, 2H), 7.43 (t, J=8.0 Hz, 1H); $^{19}$F NMR (400 MHz, CDCl$_3$) δ (ppm) −62.7; $^{13}$C NMR (100 MHz, CDCl$_3$) δ (ppm) 19.9, 25.5, 27.1, 28.2, 29.1, 32.2, 33.2, 49.3, 62.4, 68.6, 111.4, 118.4, 122.4, 125.1, 126.2, 130.2, 131.9, 132.3, 145.7, 150.6, 152.4, 158.1, 160.2.

Example 17. 7-((2-fluorophenoxy)methyl)-6-(5-hydroxypentyl)-1-isobutyl-3-methylpteridine-2,4 (1H,3H)-dione

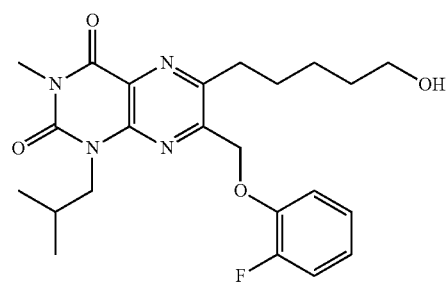

Follows Example 3 using the appropriate heteroaryl alcohol in the Mitsunobu step. Step 4B product, 5-(7-((2-fluorophenoxy)methyl)-1-isobutyl-3-methyl-2,4-dioxo-1,2,3,4-tetrahydropteridin-6-yl)pentyl acetate:

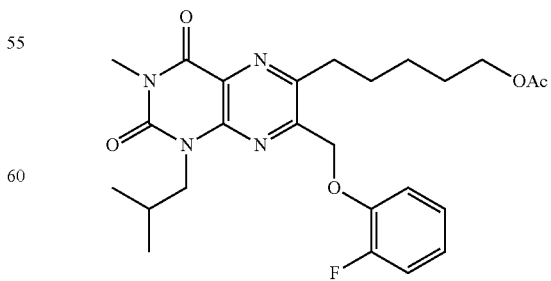

Colorless oil. $R_f$=0.45 (Hex:EA=1:1); LC-MS (ESI): m/z 487 [M+1]$^+$.

Step 5 (final) product 7-((2-fluorophenoxy)methyl)-6-(5-hydroxypentyl)-1-isobutyl-3-methylpteridine-2,4-(1H,3H)-dione: white solid. >98% purity in analytical HPLC; LC-MS (ESI): m/z 445 [M+1]$^+$. $^1$H NMR (400 MHz, CDCl$_3$) δ (ppm) 0.87 (d, J=6.8 Hz, 6H), 1.49-1.69 (m, 4H), 1.85-1.95 (m, 2H), 2.11 (sep, J=6.8 Hz, 1H), 3.06 (t, J=7.6 Hz, 2H), 3.52 (s, 3H), 3.68 (t, J=5.8 Hz, 2H), 4.06 (d, J=7.6 Hz, 2H), 5.38 (s, 2H), 6.94-7.13 (m, 4H); $^{19}$F NMR (400 MHz, CDCl$_3$) δ (ppm) −133.7; $^{13}$C NMR (100 MHz, CDCl$_3$) δ (ppm) 19.9, 25.5, 27.1, 28.3, 29.0, 32.3, 33.3, 49.3, 62.4, 69.6, 115.5, 116.6, 122.3, 124.2, 126.0, 145.8, 150.6, 151.5, 152.5, 152.8, 154.0, 160.3.

Example 18. 6-(5-hydroxypentyl)-1-isobutyl-3-methyl-7-((quinolin-6-yloxy)methyl)pteridine-2,4(1H,3H)-dione

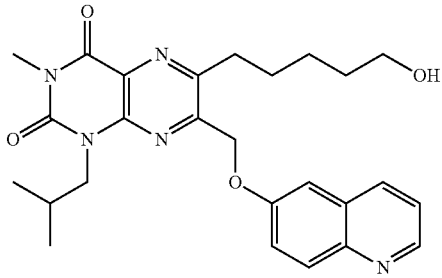 [SMILES: CC(C)Cn1c(=O)n(C)c(=O)c2nc(CCCCCO)c(COc3ccc4ncccc4c3)nc21]

Follows Example 3 using the appropriate heteroaryl alcohol in the Mitsunobu step. Step 4B product, 5-(1-isobutyl-3-methyl-2,4-dioxo-7-((quinolin-6-yloxy)methyl)-1,2,3,4-tetrahydropteridin-6-yl)pentyl acetate:

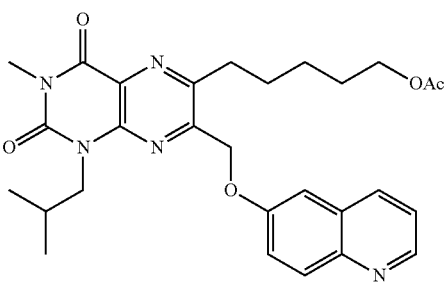 [SMILES: CC(=O)OCCCCCc1nc2c(=O)n(C)c(=O)n(CC(C)C)c2nc1COc1ccc2ncccc2c1]

Yellow solid. R$_f$=0.15 (Hex:EA=1:1); LC-MS (ESI): m/z 520 [M+1]$^+$.

Step 5 (final) product 6-(5-hydroxypentyl)-1-isobutyl-3-methyl-7-((quinolin-6-yloxy)methyl)pteridine-2,4-(1H,3H)-dione (acetate removal conditions: K$_2$CO$_3$, MeOH, room temperature, 1 h): yellow solid (TFA salt). Single peak in analytical HPLC; LC-MS (ESI): m/z 478 [M+1]$^+$. $^1$H NMR (400 MHz, CDCl$_3$) δ (ppm) 0.80 (d, J=6.8 Hz, 6H), 1.44-1.57 (m, 4H), 1.80-1.90 (m, 2H), 2.08 (sep, J=6.4 Hz, 1H), 2.98 (t, J=7.4 Hz, 2H), 3.45 (s, 3H), 3.62 (t, J=6.2 Hz, 2H), 4.01 (d, J=7.6 Hz, 2H), 5.42 (s, 2H), 7.31-7.33 (m, 1H), 7.65-7.77 (m, 2H), 8.45 (d, J=9.2 Hz, 1H), 8.52 (d, J=8.4 Hz, 1H), 9.02 (d, J=8.4 Hz, 1H).

Example 19. 7-((2,4-dibromophenoxy)methyl)-6-(5-hydroxypentyl)-1-isobutyl-3-methylpteridine-2,4(1H,3H)-dione

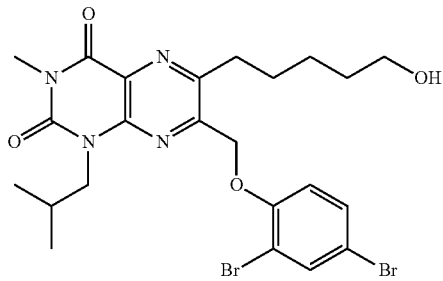

Follows Example 3 using the appropriate heteroaryl alcohol in the Mitsunobu step. Step 4B product, 5-(7-((2,4-dibromophenoxy)methyl)-1-isobutyl-3-methyl-2,4-dioxo-1,2,3,4-tetrahydropteridin-6-yl)pentyl acetate:

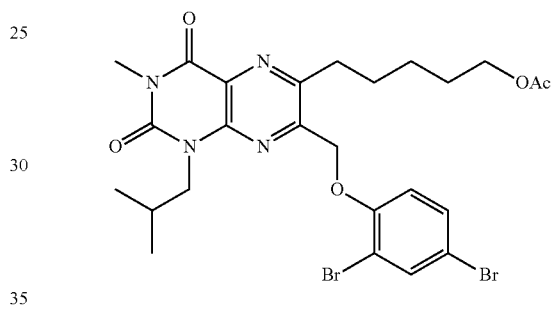

Colorless oil. R$_f$=0.40 (Hex:EA=1:1); LC-MS (ESI): m/z 625 [M+1]$^+$.

Step 5 (final) product 7-((2,4-dibromophenoxy)methyl)-6-(5-hydroxypentyl)-1-isobutyl-3-methylpteridine-2,4-(1H,3H)-dione: white solid. Single peak in analytical HPLC; LC-MS (ESI): m/z 583 [M+1]$^+$. $^1$H NMR (400 MHz, CDCl$_3$) δ (ppm) 0.79 (d, J=6.8 Hz, 6H), 1.40-1.671 (m, 4H), 1.75-1.86 (m, 2H), 2.04 (sep, J=6.8 Hz, 1H), 2.98 (t, J=7.86 Hz, 2H), 3.45 (s, 3H), 3.61 (t, J=6.2 Hz, 2H), 3.98 (d, J=7.2 Hz, 2H), 5.29 (s, 2H), 6.73 (d, J=8.8 Hz, 1H), 7.24 (dd, J=2.4, 8.8 Hz, 1H), 7.62 (d, J=2.4 Hz, 1H).

Example 20. 6-(5-hydroxypentyl)-1-isobutyl-3-methyl-7-((quinolin-7-yloxy)methyl)pteridine-2,4(1H,3H)-dione

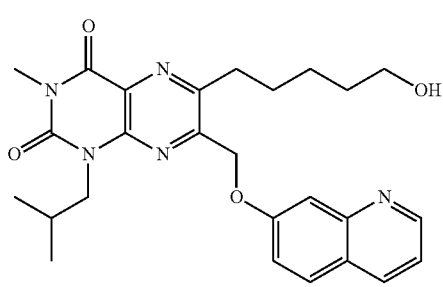

Follows Example 3 using the appropriate heteroaryl alcohol in the Mitsunobu step. Step 4B product, 5-(1-isobutyl- 3-methyl-2,4-dioxo-7-((quinolin-7-yloxy)methyl)-1,2,3,4-tetrahydropteridin-6-yl)pentyl acetate:

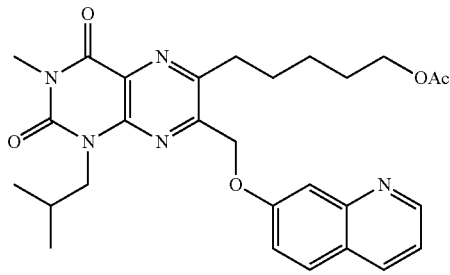 [SMILES: CC(=O)OCCCCCc1nc2c(=O)n(C)c(=O)n(CC(C)C)c2nc1COc1ccc2cccnc2c1]

Yellow solid. $R_f$=0.10 (Hex:EA=1:1); LC-MS (ESI): m/z 520 [M+1]$^+$.

Step 5 (final) product 6-(5-hydroxypentyl)-1-isobutyl-3-methyl-7-((quinolin-7-yloxy)methyl)pteridine-2,4-(1H,3H)-dione: white solid (TFA salt). >95% purity in analytical HPLC; LC-MS (ESI): m/z 478 [M+1]$^+$. $^1$H NMR (400 MHz, CDCl$_3$) δ (ppm) 0.85 (d, J=6.8 Hz, 6H), 1.51-1.67 (m, 4H), 1.90-1.98 (m, 2H), 2.15 (sep, J=6.4 Hz, 1H), 3.08 (t, J=7.6 Hz, 2H), 3.56 (s, 3H), 3.72 (t, J=6.4 Hz, 2H), 4.07 (d, J=7.6 Hz, 2H), 5.63 (s, 2H), 7.54-7.58 (m, 1H), 7.71-7.75 (m, 1H), 8.04 (d, J=9.2 Hz, 1H), 8.26 (d, J=2.0 Hz, 1H), 8.70 (d, J=8.0 Hz, 1H), 9.10 (d, J=5.6 Hz, 1H).

Example 21. 7-((2-bromo-4-chlorophenoxy)methyl)-6-(5-hydroxypentyl)-1-isobutyl-3-methylpteridine-2,4(1H,3H)-dione

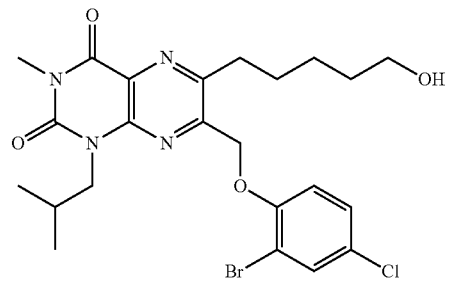 [SMILES: CC(C)Cn1c(=O)n(C)c(=O)c2nc(CCCCCO)c(COc3ccc(Cl)cc3Br)nc21]

Follows Example 3 using the appropriate heteroaryl alcohol in the Mitsunobu step. Step 4B product, 5-(7-((2-bromo-4-chlorophenoxy)methyl)-1-isobutyl-3-methyl-2,4-dioxo-1,2,3,4-tetrahydropteridin-6-yl)pentyl acetate:

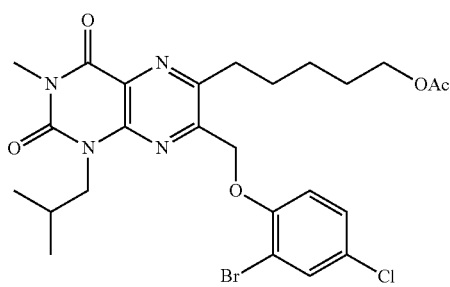 [SMILES: CC(=O)OCCCCCc1nc2c(=O)n(C)c(=O)n(CC(C)C)c2nc1COc1ccc(Cl)cc1Br]

Colorless oil. $R_f$=0.40 (Hex:EA=1:1); LC-MS (ESI): m/z 581 [M+1]$^+$.

Step 5 (final) product, 7-((2-bromo-4-chlorophenoxy)methyl)-6-(5-hydroxypentyl)-1-isobutyl-3-methylpteridine-2,4-(1H,3H)-dione: white solid. Single peak in analytical HPLC; LC-MS (ESI): m/z 539 [M+1]$^+$. $^1$H NMR (400 MHz, CDCl$_3$) δ (ppm) 0.89 (d, J=6.8 Hz, 6H), 1.50-1.71 (m, 4H), 1.85-1.95 (m, 2H), 2.09 (sep, J=6.8 Hz, 1H), 3.09 (t, J=7.6 Hz, 2H), 3.52 (s, 3H), 3.71 (t, J=6.2 Hz, 2H), 4.09 (d, J=7.6 Hz, 2H), 5.39 (s, 2H), 6.88 (d, J=8.8 Hz, 1H), 7.21 (dd, J=2.4, 8.8 Hz, 1H), 7.59 (d, J=2.4 Hz, 1H).

Example 22. 6-(5-hydroxypentyl)-1-isobutyl-3-methyl-7-((4-(trifluoromethyl)phenoxy)methyl)pteridine-2,4(1H,3H)-dione

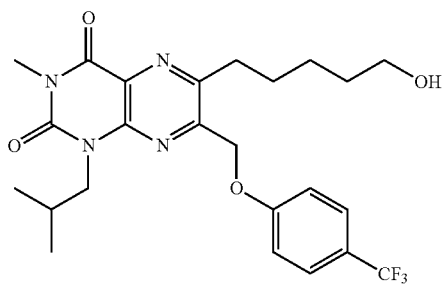 [SMILES: CC(C)Cn1c(=O)n(C)c(=O)c2nc(CCCCCO)c(COc3ccc(C(F)(F)F)cc3)nc21]

Follows Example 3 using the appropriate heteroaryl alcohol in the Mitsunobu step. Step 4B product, 5-(1-isobutyl-3-methyl-2,4-dioxo-7-((4-trifluoromethyl)phenoxy)methyl)-1,2,3,4-tetrahydropteridin-6-yl)pentyl acetate:

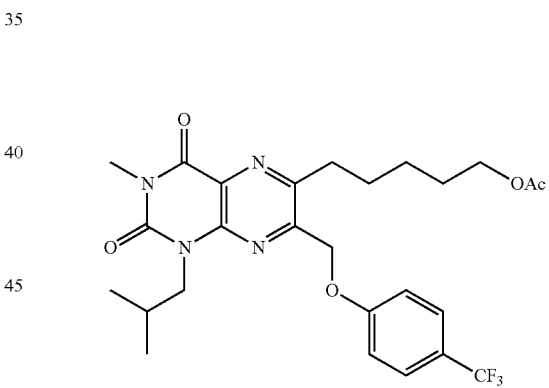

Colorless oil. $R_f$=0.40 (Hex:EA=1:1); LC-MS (ESI): m/z 537 [M+1]$^+$.

Step 5 (final) product 6-(5-hydroxypentyl)-1-isobutyl-3-methyl-7-((4-(trifluoromethyl)phenoxy)methyl)pteridine-2,4-(1H,3H)-dione: white solid. >98% purity in analytical HPLC; LC-MS (ESI): m/z 495 [M+1]$^+$. $^1$H NMR (400 MHz, CDCl$_3$) δ (ppm) 0.77 (d, J=6.8 Hz, 6H), 1.40-1.60 (m, 4H), 1.80-1.90 (m, 2H), 1.98 (sep, J=6.8 Hz, 1H), 2.98 (t, J=7.4 Hz, 2H), 3.44 (s, 3H), 3.60 (t, J=5.6 Hz, 2H), 3.97 (d, J=7.2 Hz, 2H), 5.29 (s, 2H), 6.95 (d, J=8.4 Hz, 2H), 7.47 (d, J=8.4 Hz, 2H); $^{19}$F NMR (400 MHz, CDCl$_3$) δ (ppm) −61.7; $^{13}$C NMR (100 MHz, CDCl$_3$) δ (ppm) 19.9, 25.5, 27.1, 28.2, 29.1, 32.2, 33.2, 49.3, 62.4, 68.4, 114.7, 120.1, 122.8, 123.9, 125.5, 126.1, 127.0, 127.1, 128.2, 145.7, 150.6, 152.3, 160.2.

Example 23. 7-(([1,1'-biphenyl]-2-yloxy)methyl)-6-(5-hydroxypentyl)-1-isobutyl-3-methylpteridine-2,4(1H,3H)-dione

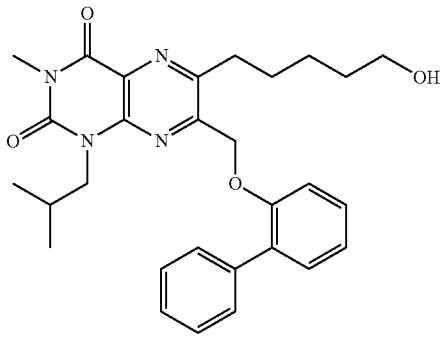 [SMILES: CC(C)Cn1c(=O)n(C)c(=O)c2nc(CCCCCO)c(COc3ccccc3-c3ccccc3)nc21]

Follows Example 3 using the appropriate heteroaryl alcohol in the Mitsunobu step. Step 4B product, 5-(7-((([1,1'-biphenyl]-2-yloxy)methyl)-1-isobutyl-3-methyl-2,4-dioxo-1,2,3,4-tetrahydropteridin-6-yl)pentyl acetate:

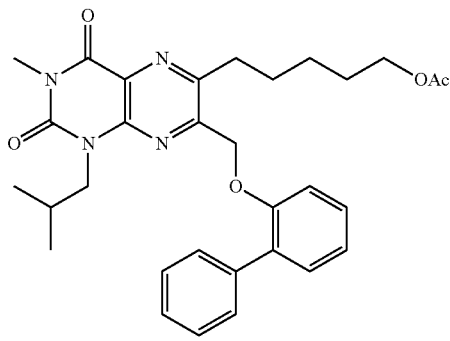 [SMILES: CC(=O)OCCCCCc1nc2c(=O)n(C)c(=O)n(CC(C)C)c2nc1COc1ccccc1-c1ccccc1]

Colorless oil. $R_f$=0.50 (Hex:EA=1:1); LC-MS (ESI): m/z 545 [M+1]$^+$.

Step 5 (final) product, 7-(([1,1'-biphenyl]-2-yloxy)methyl)-6-(5-hydroxypentyl)-1-isobutyl-3-methylpteridine-2,4-(1H,3H)-dione: white solid. Single peak in analytical HPLC; LC-MS (ESI): m/z 503 [M+1]$^+$. $^1$H NMR (400 MHz, CDCl$_3$) δ (ppm) 0.75 (d, J=6.8 Hz, 6H), 1.25-1.31 (m, 2H), 1.41-1.46 (m, 2H), 1.57-1.63 (m, 2H), 1.97 (sep, J=6.8 Hz, 1H), 2.77 (t, J=7.4 Hz, 2H), 3.43 (s, 3H), 3.56 (t, J=5.8 Hz, 2H), 3.98 (d, J=7.2 Hz, 2H), 5.19 (s, 2H), 6.91-7.00 (m, 2H), 7.16-7.28 (m, 5H), 7.38-7.41 (m, 2H); $^{13}$C NMR (100 MHz, CDCl$_3$) δ (ppm) 19.9, 25.3, 27.1, 27.8, 29.0, 32.2, 33.0, 49.2, 62.4, 69.2, 113.4, 122.2, 125.8, 127.1, 128.0, 128.5, 129.4, 131.3, 131.5, 138.1, 145.6, 150.7, 152.4, 153.3, 154.8, 160.3.

Example 24. 7-((2-bromo-5-fluorophenoxy)methyl)-6-(5-hydroxypentyl)-1-isobutyl-3-methylpteridine-2,4(1H,3H)-dione

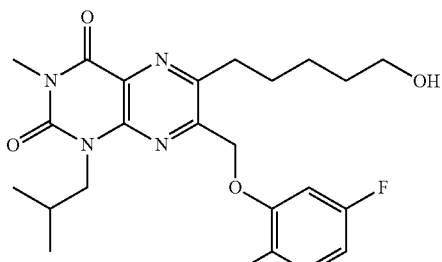

Follows Example 3 using the appropriate heteroaryl alcohol in the Mitsunobu step. Step 4B product, 5-(7-((2-bromo-5-fluorophenoxy)methyl)-1-isobutyl-3-methyl-2,4-dioxo-1,2,3,4-tetrahydropteridin-6-yl)pentyl acetate:

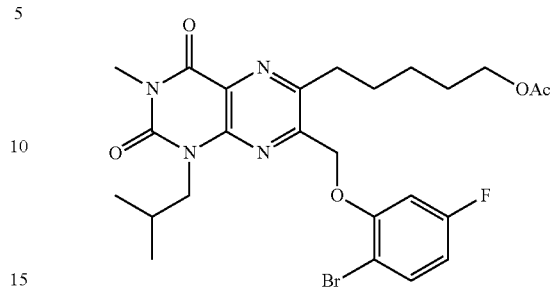

Colorless oil. $R_f$=0.45 (Hex:EA=1:1); LC-MS (ESI): m/z 565 [M+1]$^+$.

Step 5 (final) product, 7-((2-bromo-5-fluorophenoxy)methyl)-6-(5-hydroxypentyl)-1-isobutyl-3-methylpteridine-2,4-(1H,3H)-dione: white solid. Single peak in analytical HPLC; LC-MS (ESI): m/z 523 [M+1]$^+$. $^1$H NMR (400 MHz, CDCl$_3$) δ (ppm) 0.70 (d, J=6.8 Hz, 6H), 1.40-1.61 (m, 4H), 1.75-1.90 (m, 2H), 2.07 (sep, J=6.8 Hz, 1H), 3.00 (t, J=7.6 Hz, 2H), 3.44 (s, 3H), 3.60 (t, J=5.8 Hz, 2H), 4.00 (d, J=7.2 Hz, 2H), 5.30 (s, 2H), 6.53-6.57 (m, 1H), 6.64-6.67 (m, 1H), 7.41-7.44 (m, 1H); $^{19}$F NMR (400 MHz, CDCl$_3$) δ (ppm) −111.3; $^{13}$C NMR (100 MHz, CDCl$_3$) δ (ppm) 19.9, 25.5, 27.1, 28.1, 29.1, 32.3, 33.3, 49.4, 62.4, 69.3, 101.9, 106.3, 109.4, 126.3, 134.0, 145.7, 150.6, 152.0, 155.2, 160.1, 161.2, 163.7.

Example 25. 6-(5-hydroxypentyl)-1-isobutyl-7-((isoquinolin-8-yloxy)methyl)-3-methylpteridine-2,4(1H,3H)-dione

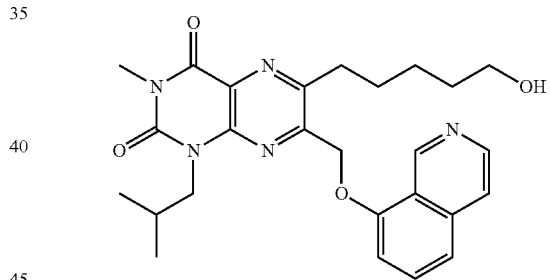

Follows Example 3 using the appropriate heteroaryl alcohol in the Mitsunobu step. Step 4B product, 5-(1-isobutyl-7-((isoquinolin-8-yloxy)methyl)-3-methyl-2,4-dioxo-1,2,3,4-tetrahydropteridin-6-yl)pentyl acetate:

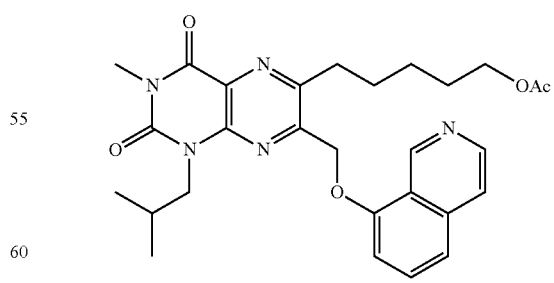

Yellow solid. $R_f$=0.10 (Hex:EA=1:1); LC-MS (ESI): m/z 520 [M+1]$^+$.

Step 5 (final) product, 6-(5-hydroxypentyl-1-isobutyl-7-((isoquinolin-8-yloxy)methyl)-3-methyl-pteridine-2,4-(1H,3H)-dione: white solid (TFA salt). Single peak in analytical HPLC; LC-MS (ESI): m/z 478 [M+1]⁺. ¹H NMR (400 MHz, CD₃OD) δ (ppm) 0.45 (d, J=6.8 Hz, 6H), 1.42-1.55 (m, 4H), 1.60-1.81 (m, 3H), 2.97 (t, J=7.8 Hz, 2H), 3.35 (s, 3H), 3.45 (t, J=6.4 Hz, 2H), 3.72 (d, J=7.6 Hz, 2H), 5.82 (s, 2H), 7.39 (d, J=8.0 Hz, 1H), 7.76 (d, J=8.0 Hz, 1H), 8.02 (t, J=8.0 Hz, 1H), 8.34 (s, 1H), 8.50 (s, 1H), 9.82 (s, 1H).

Example 26. 6-(5-hydroxypentyl)-1-isobutyl-3-methyl-7-((quinolin-8-yloxy)methyl)pteridine-2,4(1H,3H)-dione

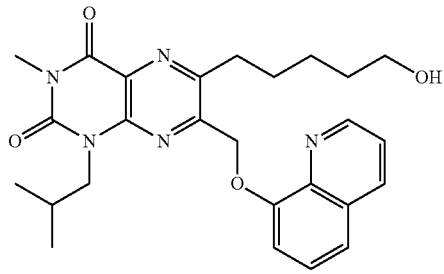 [SMILES: CC(C)Cn1c(=O)n(C)c(=O)c2nc(CCCCCO)c(COc3cccc4cccnc34)nc21]

Follows Example 3 using the appropriate heteroaryl alcohol in the Mitsunobu step. Step 4B product, 5-(1-isobutyl-3-methyl-2,4-dioxo-7-((quinolin-8-yloxy)methyl)-1,2,3,4-tetrahydropteridin-6-yl)pentyl acetate:

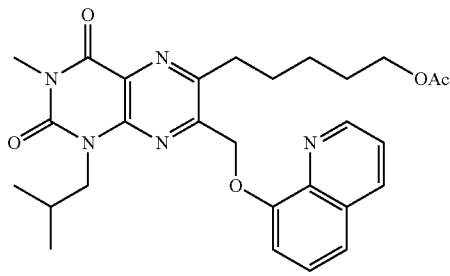 [SMILES: CC(=O)OCCCCCc1nc2c(=O)n(C)c(=O)n(CC(C)C)c2nc1COc1cccc2cccnc12]

Yellow solid. R_f=0.15 (EA); LC-MS (ESI): m/z 520 [M+1]⁺.

Step 5 (final) product, 6-(5-hydroxypentyl-1-isobutyl-3-methyl-7-((quinolin-8-yloxy)methyl)pteridine-2,4-(1H,3H)-dione (acetate removal conditions: K₂CO₃, MeOH, room temperature, 1 h): white solid (TFA salt). Single peak in analytical HPLC; LC-MS (ESI): m/z 478 [M+1]⁺. ¹H NMR (400 MHz, CDCl₃) δ (ppm) 0.68 (d, J=6.8 Hz, 6H), 1.39-1.50 (m, 4H), 1.70-1.83 (m, 2H), 1.99 (sep, J=6.8 Hz, 1H), 3.06 (t, J=7.2 Hz, 2H), 3.44 (s, 3H), 3.54 (s, 2H), 3.94 (d, J=7.2 Hz, 2H), 5.57 (s, 2H), 7.24 (d, J=6.8 Hz, 1H), 7.46-7.52 (m, 2H), 7.66 (d, J=8.0 Hz, 1H), 8.44 (d, J=8.0 Hz, 1H), 9.20 (s, 1H).

Example 27. 6-(5-hydroxypentyl)-1-isobutyl-7-((isoquinolin-3-yloxy)methyl)-3-methylpteridine-2,4(1H,3H)-dione

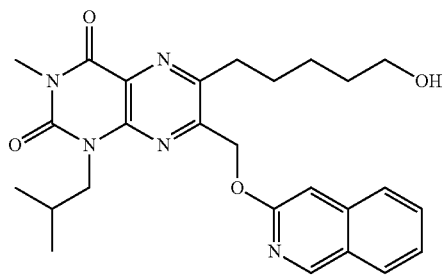

Follows Example 3 using the appropriate heteroaryl alcohol in the Mitsunobu step. Step 4B product, 5-(1-isobutyl-7-((isoquinolin-3-yloxy)methyl)-3-methyl-2,4-dioxo-1,2,3,4-tetrahydropteridin-6-yl)pentyl acetate:

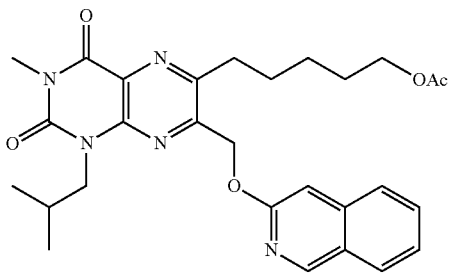 [SMILES: CC(=O)OCCCCCc1nc2c(=O)n(C)c(=O)n(CC(C)C)c2nc1COc1cc2ccccc2cn1]

Yellow solid. R_f=0.15 (Hex:EA=1:1); LC-MS (ESI): m/z 520 [M+1]⁺.

Step 5 (final) product, 6-(5-hydroxypentyl)-1-isobutyl-7-((isoquinolin-3-yloxy)methyl)-3-methylpteridine-2,4-(1H,3H)-dione (acetate removal conditions: K₂CO₃, MeOH, room temperature, 1 h): yellow solid (TFA salt). Single peak in analytical HPLC; LC-MS (ESI): m/z 478 [M+1]⁺. ¹H NMR (400 MHz, MeOD-d₄) δ (ppm) 0.40 (d, J=6.8 Hz, 6H), 1.40-1.62 (m, 4H), 1.75-1.90 (m, 3H), 2.94 (t, J=7.6 Hz, 2H), 3.32 (s, 3H), 3.48 (t, J=6.4 Hz, 2H), 3.71 (d, J=7.6 Hz, 2H), 5.74 (s, 2H), 7.17 (s, 1H), 7.30-7.35 (m, 1H), 7.52-7.56 (m, 1H), 7.68 (d, J=8.4 Hz, 1H), 7.84 (d, J=8.4 Hz, 1H), 8.77 (s, 1H).

Example 28. 6-(5-hydroxypentyl)-1-isobutyl-3-methyl-7-((pyridin-4-yloxy)methyl)pteridine-2,4(1H,3H)-dione

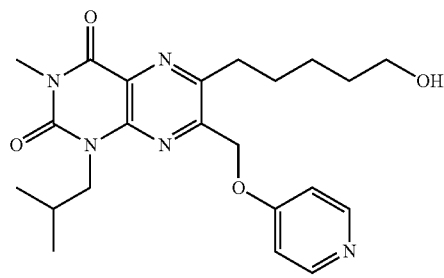

Follows Example 3 using the appropriate heteroaryl alcohol in the Mitsunobu step. Step 4B product, 5-(1-isobutyl-3-methyl-2,4-dioxo-7-((pyridin-4-yloxy)methyl)-1,2,3,4-tetrahydropteridin-6-yl)pentyl acetate:

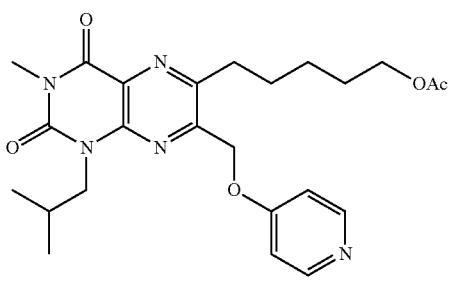 [SMILES: CC(=O)OCCCCCc1nc2c(=O)n(C)c(=O)n(CC(C)C)c2nc1COc1ccncc1]

Yellow solid. $R_f$=0.15 (Hex:EA=1:1); LC-MS (ESI): m/z 470 [M+1]⁺.

Step 5 (final) product, 6-(5-hydroxypentyl-1-isobutyl-3-methyl-7-((pyridin-4-yloxy)methyl)pteridine-2,4-(1H,3H)-dione: white solid (TFA salt). Single peak in analytical HPLC; LC-MS (ESI): m/z 428 [M+1]⁺. ¹H NMR (400 MHz, CD₃OD) δ (ppm) 0.67 (d, J=6.8 Hz, 6H), 1.40-1.53 (m, 4H), 1.75-1.91 (m, 3H), 2.90 (t, J=7.8 Hz, 2H), 3.36 (s, 3H), 3.48 (t, J=6.4 Hz, 2H), 3.79 (d, J=7.2 Hz, 2H), 5.81 (s, 2H), 7.57 (d, J=6.0 Hz, 2H), 8.63 (d, J=6.0 Hz, 2H).

Example 29. 7-(((6,8-dibromoisoquinolin-5-yl)oxy)methyl)-6-(5-hydroxypentyl)-1-isobutyl-3-methylpteridine-2,4(1H,3H)-dione

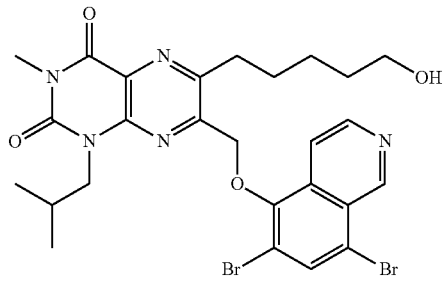 [SMILES: CC(C)Cn1c(=O)n(C)c(=O)c2nc(CCCCCO)c(COc3c(Br)cc(Br)c4cnccc34)nc21]

Follows Example 3 using the appropriate heteroaryl alcohol in the Mitsunobu step. Step 4B product, 5-(7-(((6,8-dibromoisoquinolin-5-yl)oxy)methyl)-1-isobutyl-3-methyl-2,4-dioxo-1,2,3,4-tetrahydropteridin-6-yl)pentyl acetate:

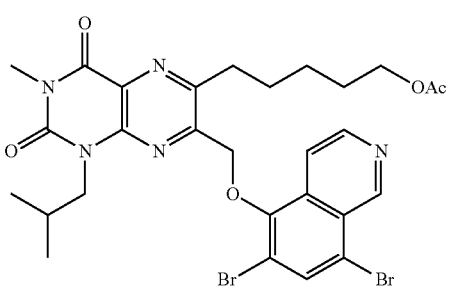 [SMILES: CC(=O)OCCCCCc1nc2c(=O)n(C)c(=O)n(CC(C)C)c2nc1COc1c(Br)cc(Br)c2cnccc12]

Yellow solid. $R_f$=0.20 (Hex:EA=1:1); LC-MS (ESI): m/z 676 [M+1]⁺.

Step 5 (final) product, 7-(((6,8-dibromoisoquinolin-5-yl)oxy)methyl)-6-(5-hydroxypentyl-1-isobutyl-3-methylpteridine-2,4-(1H,3H)-dione: white solid (TFA salt). Single peak in analytical HPLC; LC-MS (ESI): m/z 634 [M+1]⁺. ¹H NMR (400 MHz, CD₃OD) δ (ppm) 0.64 (d, J=6.8 Hz, 6H), 1.45-1.63 (m, 5H), 1.80-1.90 (m, 2H), 3.16 (t, J=7.8 Hz, 2H), 3.37 (s, 3H), 3.49 (t, J=6.2 Hz, 2H), 3.79 (d, J=7.6 Hz, 2H), 5.40 (s, 2H), 7.86 (s, 1H), 8.09 (s, 1H), 8.55 (s, 1H).

Example 30. 6-(5-hydroxypentyl)-1-isobutyl-3-methyl-7-((quinoxalin-5-yloxy)methyl)pteridine-2,4(1H,3H)-dione

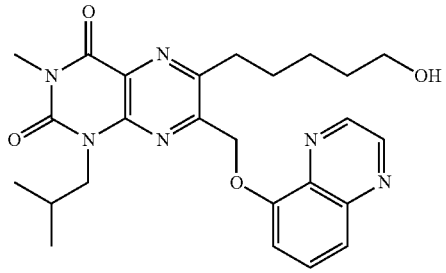

Follows Example 3 using the appropriate heteroaryl alcohol in the Mitsunobu step. Step 4B product, 5-(1-isobutyl-3-methyl-2,4-dioxo-7-((quinoxalin-5-yloxy)methyl)-1,2,3,4-tetrahydropteridin-6-yl)pentyl acetate:

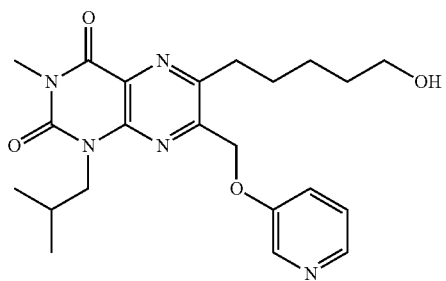 [SMILES: CC(C)Cn1c(=O)n(C)c(=O)c2nc(CCCCCO)c(COc3cccnc3)nc21]

Yellow solid. $R_f$=0.15 (Hex:EA=1:1); LC-MS (ESI): m/z 521 [M+1]⁺.

Step 5 (final) product, 6-(5-hydroxypentyl-1-isobutyl-3-methyl-7-((quinoxalin-5-yloxy)methyl)pteridine-2,4-(1H,3H)-dione: white solid (TFA salt). Single peak in analytical HPLC; LC-MS (ESI): m/z 479 [M+1]⁺. ¹H NMR (400 MHz, CD₃OD) δ (ppm) 0.43 (d, J=6.8 Hz, 6H), 1.38-1.46 (m, 4H), 1.74-1.83 (m, 3H), 2.97 (t, J=7.8 Hz, 2H), 3.34 (s, 3H), 3.43 (t, J=6.4 Hz, 2H), 3.72 (d, J=7.6 Hz, 2H), 5.69 (s, 2H), 7.21 (dd, J=2.0, 6.8 Hz, 1H), 7.59-7.63 (m, 2H), 8.77 (d, J=2.0 Hz, 1H), 8.84 (d, J=2.0 Hz, 1H).

Example 31. 6-(5-hydroxypentyl)-1-isobutyl-3-methyl-7-((pyridin-3-yloxy)methyl)pteridine-2,4(1H,3H)-dione Follows Example 3 using the appropriate heteroaryl alcohol in the Mitsunobu step. Step 4B product, 5-(1-isobutyl- 3-methyl-2,4-dioxo-7-((pyridine-3-yloxy)methyl)-1,2,3,4-tetrahydropteridin-6-yl)pentyl acetate:

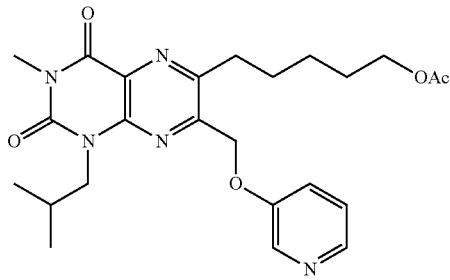 [SMILES: CC(=O)OCCCCCc1nc2c(=O)n(C)c(=O)n(CC(C)C)c2nc1COc1cccnc1]

Colorless oil. $R_f$=0.15 (Hex:EA=1:1); LC-MS (ESI): m/z 470 [M+1]$^+$.

Step 5 (final) product, 6-(5-hydroxypentyl)-1-isobutyl-3-methyl-7-((pyridine-3-yloxy)methyl)pteridine-2,4-(1H,3H)-dione: white solid (TFA salt). Single peak in analytical HPLC; LC-MS (ESI): m/z 428 [M+1]$^+$. $^1$H NMR (400 MHz, CDCl$_3$) δ (ppm) 0.80 (d, J=6.8 Hz, 6H), 1.50-1.71 (m, 4H), 1.80-1.91 (m, 2H), 2.02 (sep, J=6.8 Hz, 1H), 3.03 (t, J=7.8 Hz, 2H), 3.48 (s, 3H), 3.60 (t, J=6.2 Hz, 2H), 3.95 (d, J=7.2 Hz, 2H), 5.76 (s, 2H), 8.00 (s, 1H), 8.19-8.22 (m, 1H), 8.61 (br s, 2H).

Example 32. 6-(5-hydroxypentyl)-1-isobutyl-3-methyl-7-((3-nitrophenoxy)methyl)pteridine-2,4(1H,3H)-dione

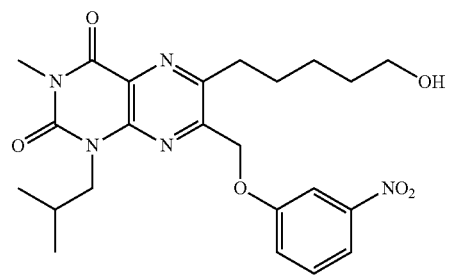

Follows Example 3 using the appropriate heteroaryl alcohol in the Mitsunobu step. Step 4B product, 5-(1-isobutyl-3-methyl-7-((3-nitrophenoxy)methyl)-2,4-dioxo-1,2,3,4-tetrahydropteridin-6-yl)pentyl acetate:

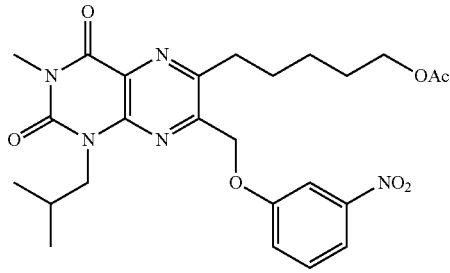

Colorless oil. $R_f$=0.30 (Hex:EA=1:1); LC-MS (ESI): m/z 514 [M+1]$^+$.

Step 5 (final) product, 6-(5-hydroxypentyl)-1-isobutyl-3-methyl-7-((3-nitrophenoxy)methyl)pteridine-2,4-(1H,3H)-dione: yellow solid. Single peak in analytical HPLC; LC-MS (ESI): m/z 472 [M+1]$^+$. $^1$H NMR (400 MHz, CDCl$_3$) δ (ppm) 0.80 (d, J=6.8 Hz, 6H), 1.40-1.62 (m, 4H), 1.82-1.90 (m, 2H), 2.07 (sep, J=6.8 Hz, 1H), 2.97 (t, J=7.0 Hz, 2H), 3.45 (s, 3H), 3.62 (t, J=6.2 Hz, 2H), 4.01 (d, J=7.2 Hz, 2H), 5.32 (s, 2H), 7.21-7.24 (m, 1H), 7.37-7.41 (m, 1H), 7.78-7.82 (m, 2H).

Example 33. 7-((3-aminophenoxy)methyl)-6-(5-hydroxypentyl)-1-isobutyl-3-methylpteridine-2,4 (1H,3H)-dione

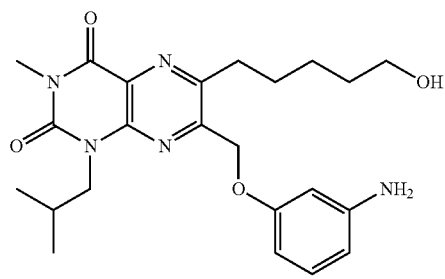

Prepared from the product of Example 32 by catalytic hydrogenation using Pd/C. Data: yellow solid (TFA salt). Single peak in analytical HPLC; LC-MS (ESI): m/z 442 [M+1]$^+$. $^1$H NMR (400 MHz, CDCl$_3$) δ (ppm) 0.80 (d, J=6.8 Hz, 6H), 1.30-1.52 (m, 4H), 1.65-1.80 (m, 2H), 2.06 (sep, J=6.8 Hz, 1H), 2.87 (t, J=7.0 Hz, 2H), 3.42 (s, 3H), 3.55 (t, J=6.2 Hz, 2H), 4.00 (d, J=7.2 Hz, 2H), 5.22 (s, 2H), 6.61-6.69 (m, 3H), 7.12-7.16 (m, 1H).

Example 34. 2-((6-(5-hydroxypentyl)-1-isobutyl-3-methyl-2,4-dioxo-1,2,3,4-tetrahydropteridin-7-yl)methoxy)benzonitrile

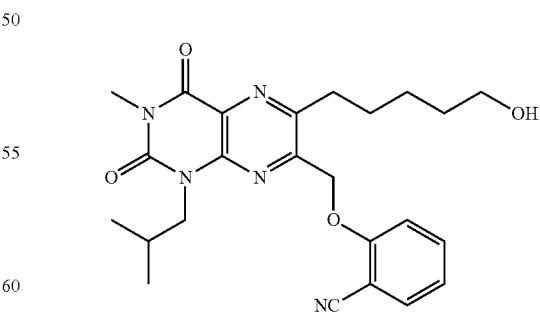

Follows Example 3 using the appropriate heteroaryl alcohol in the Mitsunobu step. Step 4B product, 5-(7-((2-cyanophenoxy)methyl)-1-isobutyl-3-methyl-2,4-dioxo-1,2,3,4-tetrahydropteridin-6-yl)pentyl acetate:

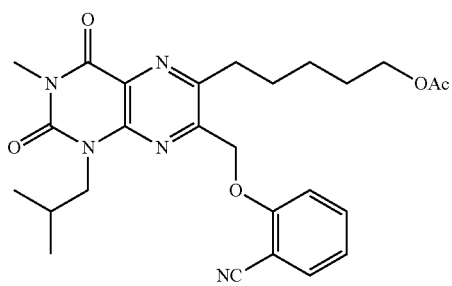 [SMILES: CC(=O)OCCCCCc1nc2c(=O)n(C)c(=O)n(CC(C)C)c2nc1COc1ccccc1C#N]

Colorless oil. $R_f$=0.15 (Hex:EA=1:1); LC-MS (ESI): m/z 494 [M+1]$^+$.

Step 5 (final) product, 2-((6-(5-hydroxypentyl)-1-isobutyl-3-methyl-2,4-dioxo-1,2,3,4-tetrahydropteridine-7-yl)methoxy)benzonitrile: orange solid. Single peak in analytical HPLC; LC-MS (ESI): m/z 452 [M+1]$^+$. $^1$H NMR (400 MHz, DMSO-d$_6$) δ (ppm) 0.88 (d, J=6.8 Hz, 6H), 1.40-1.69 (m, 6H), 2.18 (sep, J=6.8 Hz, 1H), 3.20 (t, J=7.8 Hz, 2H), 3.33 (s, 3H), 3.45 (t, J=6.4 Hz, 2H), 3.97 (d, J=7.6 Hz, 2H), 4.32 (t, J=5.2 Hz, 1H), 7.08 (s, 2H), 7.22-7.27 (m, 1H), 7.44-7.47 (m, 2H), 7.91 (d, J=7.6 Hz, 1H).

Certain compounds of the invention were made using the product of Example 1 as the starting material and following the procedures of General Scheme 3:

General Scheme 3

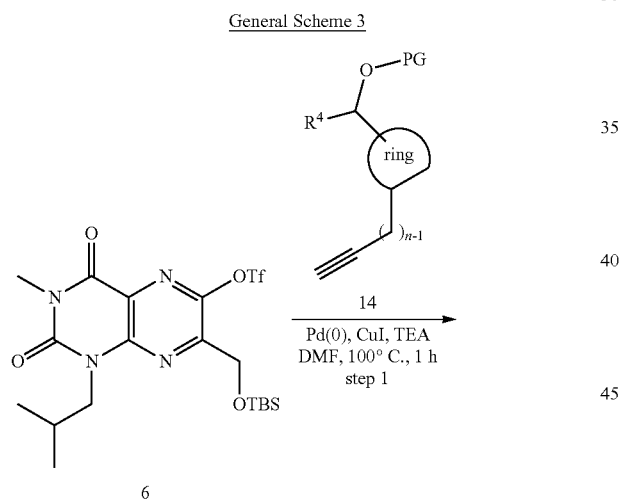

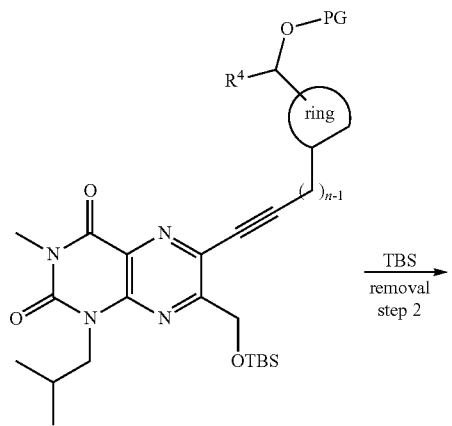

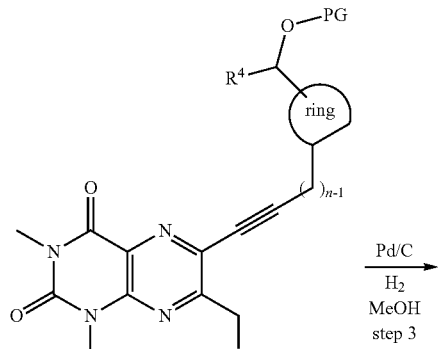

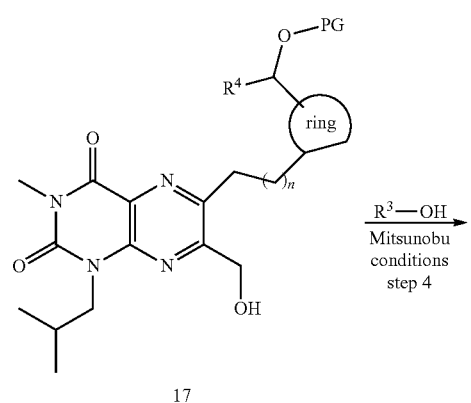

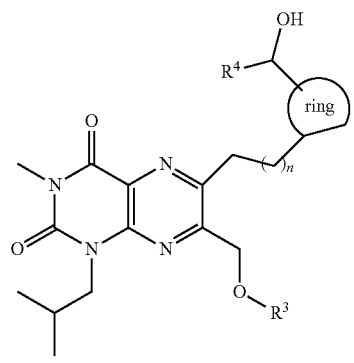

PG = protecting group

The following compounds were made according to the methods of General Scheme 3:

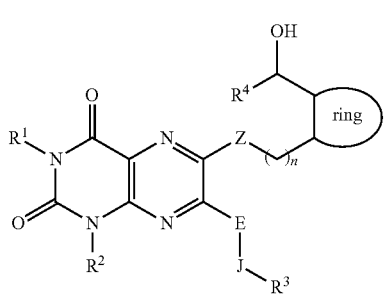

TABLE 2

B  R¹ = Me, R² = i-Bu, R⁴ = H, Z = CH₂, n = 1, E = CH₂, J = O,

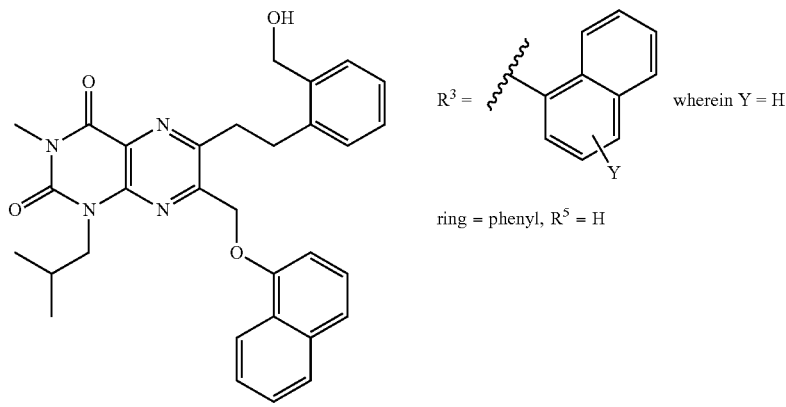

ring = phenyl, R⁵ = H

Example 35. 6-(2-(hydroxymethyl)phenethyl)-1-isobutyl-3-methyl-7-((naphthalen-1-yloxy)methyl)pteridine-2,4(1H,3H)-dione

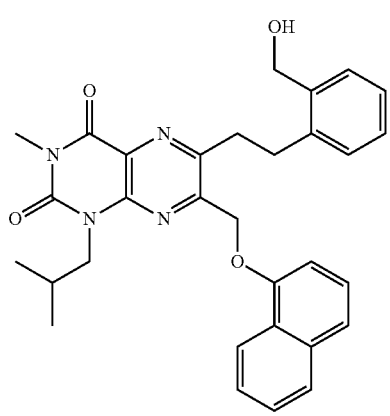 [SMILES: CC(C)Cn1c(=O)n(C)c(=O)c2nc(CCc3ccccc3CO)c(COc3cccc4ccccc34)nc21]

Step 1

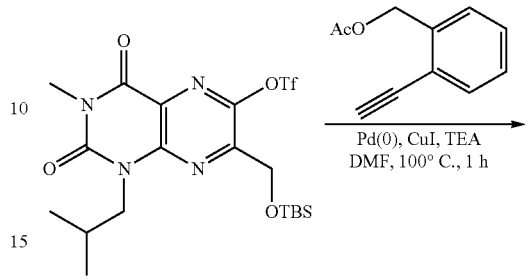

-continued

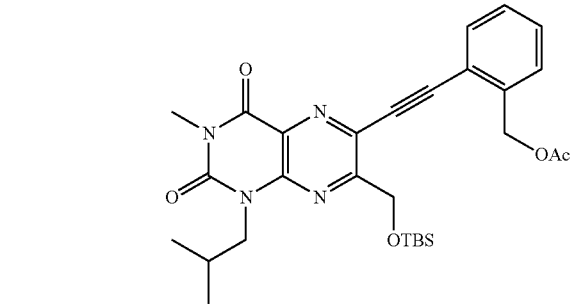

2-((7-(((tert-butyldimethylsilyl)oxy)methyl)-1-isobutyl-3-methyl-2,4-dioxo-1,2,3,4-tetrahydropteridin-6-yl)ethynyl)benzyl acetate: A mixture of 7-(((tert-butyldimethylsilyl)oxy)methyl)-1-isobutyl-3-methyl-2,4-dioxo-1,2,3,4-tetrahydropteridin-6-yl trifluoromethanesulfonate (1.37 g, 2.61 mmol), 2-ethynylbenzyl acetate (0.591 g, 3.39 mmol), and CuI (75 mg, 0.39 mmol) in DMF (39 mL) was degassed. Pd(PPh₃)₄ (151 mg, 0.13 mmol) was added followed by TEA (1.58 g, 15.7 mmol), and degassed. The reaction was stirred at 100° C. for 1 hour, then cooled to room temperature. The reaction was quenched with saturated NH₄Cl, extracted with EA. The combined organic extracts were washed with brine, dried over Na₂SO₄. The solvent was removed and the residue was purified by column (Hex:

EA=3:1) to afford 1.31 g (91%) of 2-((7-(((tert-butyldimethylsilyl)oxy)methyl)-1-isobutyl-3-methyl-2,4-dioxo-1,2,3,4-tetrahydropteridin-6-yl)ethynyl)benzyl acetate as a yellow solid. $R_f$=0.65 (Hex:EA=1:1); LC-MS (ESI): m/z 551 [M+1]$^+$. $^1$H NMR (400 MHz, CDCl$_3$) δ (ppm) 0.17 (s, 6H), 0.97 (s, 9H), 1.02 (d, J=6.0 Hz, 6H), 2.15 (s, 3H), 2.32 (hep, J=6.4 Hz, 1H), 3.56 (s, 3H), 4.26 (d, J=7.6 Hz, 2H), 5.17 (s, 2H), 5.40 (s, 2H), 7.24-7.69 (m, 4H).

Steps 2 and 3

LC-MS (ESI): m/z 441 [M+1]$^+$. $^1$H NMR (400 MHz, CDCl$_3$) δ (ppm) 0.96 (d, J=6.8 Hz, 6H), 2.11 (s, 3H), 2.24 (hep, J=6.4 Hz, 1H), 3.16-3.20 (m, 4H), 3.56 (s, 3H), 4.18 (d, J=7.6 Hz, 2H), 4.67 (s, 2H), 5.18 (s, 2H), 7.10-7.37 (m, 4H).

Step 4

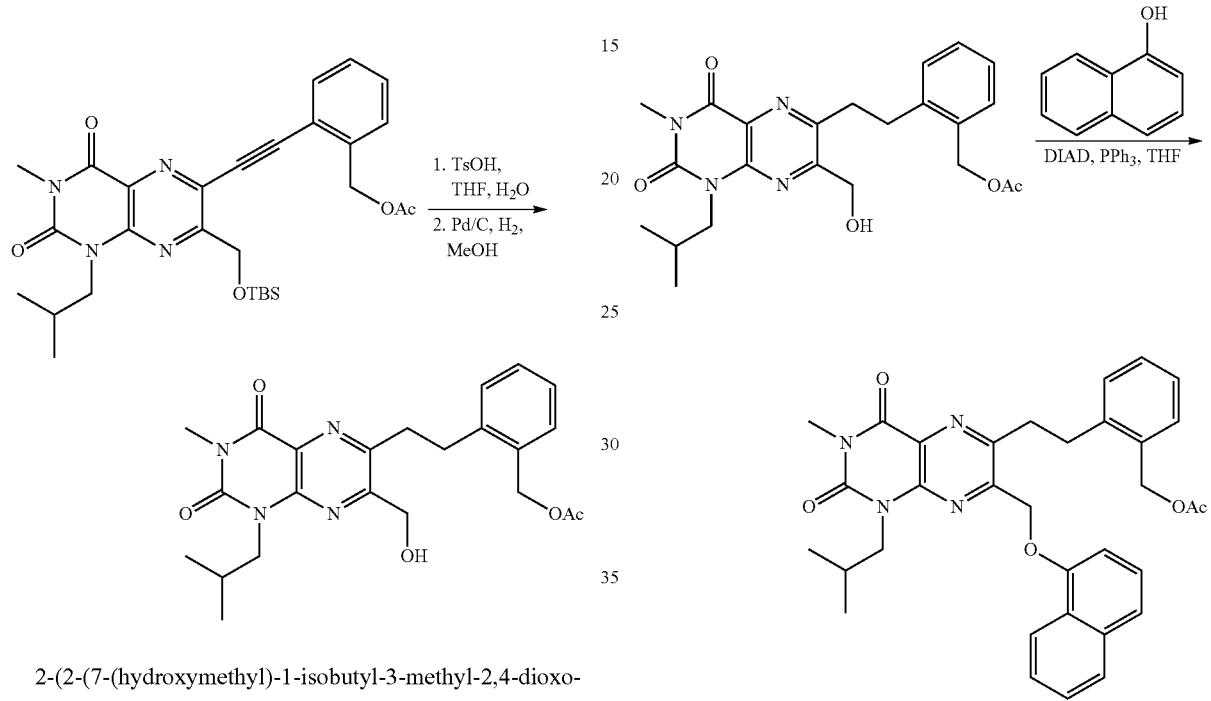

2-(2-(7-(hydroxymethyl)-1-isobutyl-3-methyl-2,4-dioxo-1,2,3,4-tetrahydropteridin-6-yl)ethyl)benzyl acetate: A solution of 2-((7-(((tert-butyldimethylsilyl)oxy)methyl)-1-isobutyl-3-methyl-2,4-dioxo-1,2,3,4-tetrahydropteridin-6-yl)ethynyl)benzyl acetate (1.19 g, 2.16 mmol) in THF (65 mL) was treated with a solution of TsOH (0.41 g, 2.16 mmol) in H$_2$O (13 mL). The reaction was stirred at room temperature for 24 hours. The reaction was diluted with EA, washed with brine, dried over Na$_2$SO$_4$. The solvent was removed and the residue was purified by column (Hex: EA=1:1) to afford 2-((7-(hydroxymethyl)-1-isobutyl-3-methyl-2,4-dioxo-1,2,3,4-tetrahydropteridin-6-yl)ethynyl)benzyl acetate as a yellow solid, which was used directly for the next step. $R_f$=0.25 (Hex:EA=1:1); LC-MS (ESI): m/z 437 [M+1]$^+$. A solution of 2-(2-(7-(hydroxymethyl)-1-isobutyl-3-methyl-2,4-dioxo-1,2,3,4-tetrahydropteridin-6-yl)ethynyl)benzyl acetate in MeOH (100 mL) and THF (20 mL) was treated with Pd/C (160 mg, 10% on charcoal) and stirred under atmosphere of H$_2$ for 1 h. The reaction was filtered and concentrated. The crude product was purified by column (Hex:EA=1:1) to afford 293 mg (31% for two steps) of 2-((7-(((tert-butyldimethylsilyl)oxy)methyl)-1-isobutyl-3-methyl-2,4-dioxo-1,2,3,4-tetrahydropteridin-6-yl)ethynyl)benzyl acetate as a white solid. $R_f$=0.20 (Hex:EA=1:1);

2-(2-(1-isobutyl-3-methyl-7-((naphthalen-1-yloxy)methyl)-2,4-dioxo-1,2,3,4-tetrahydropteridin-6-yl)ethyl)benzyl acetate: A mixture of 2-((7-(((tert-butyldimethylsilyl)oxy)methyl)-1-isobutyl-3-methyl-2,4-dioxo-1,2,3,4-tetrahydropteridin-6-yl)ethynyl)benzyl acetate (44 mg, 0.10 mmol), naphthalen-1-ol (22 mg, 0.15 mmol), and PPh$_3$ (39 mg, 0.15 mmol) in THF (4 mL) was treated with DIAD (30 mg, 0.15 mmol). The reaction was stirred at room temperature for 24 hours. The reaction was diluted with EA, washed with brine, dried over Na$_2$SO$_4$. The solvent was removed and the residue was purified by column (Hex:EA=3:1) to afford 35 mg (62%) of 2-(2-(1-isobutyl-3-methyl-7-((naphthalen-1-yloxy)methyl)-2,4-dioxo-1,2,3,4-tetrahydropteridin-6-yl)ethyl)benzyl acetate as a yellow oil. $R_f$=0.45 (Hex: EA=1:1); LC-MS (ESI): m/z 567 [M+1]$^+$. $^1$H NMR (400 MHz, CDCl$_3$) δ (ppm) 0.77 (d, J=6.4 Hz, 6H), 2.00 (s, 3H), 2.08 (hep, J=6.4 Hz, 1H), 3.27 (t, J=7.4 Hz, 2H), 3.44 (t, J=7.4 Hz, 2H), 3.58 (s, 3H), 4.03 (d, J=7.6 Hz, 2H), 5.12 (s, 2H), 5.21 (s, 2H), 6.65 (d, J=7.1 Hz, 1H), 7.06 (dd, J=1.6, 6.8 Hz, 1H), 7.20-7.52 (m, 7H), 7.81 (d, J=8.0 Hz, 1H), 8.21 (d, J=8.4 Hz, 1H).

Step 5

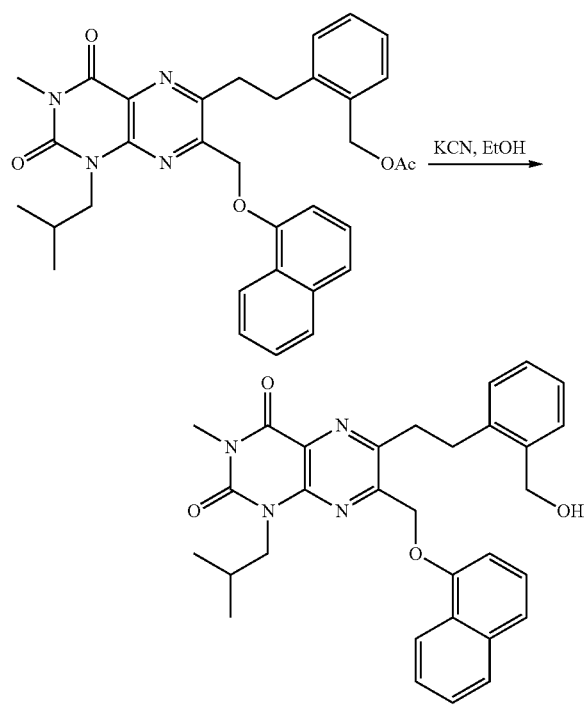

6-(2-(hydroxymethyl)phenethyl)-1-isobutyl-3-methyl-7-((naphthalen-1-yloxy)methyl)pteridine-2,4(1H,3H)-dione: A solution of 2-(2-(1-isobutyl-3-methyl-7-((naphthalen-1-yloxy)methyl)-2,4-dioxo-1,2,3,4-tetrahydropteridin-6-yl)ethyl)benzyl acetate (35 mg, 0.062 mmol) in EtOH (10 mL, 95%) was treated with KCN (45 mg). The reaction was stirred at room temperature for 24 h. The reaction was concentrated and purified by preparative HPLC to afford 25 mg (77%) of 6-(2-(hydroxymethyl)phenethyl)-1-isobutyl-3-methyl-7-((naphthalen-1-yloxy)methyl)pteridine-2,4(1H, 3H)-dione as a white solid. LC-MS (ESI): m/z 525 [M+1]$^+$. $^1$H NMR (400 MHz, CDCl$_3$) δ (ppm) 0.79 (d, J=6.8 Hz, 6H), 2.10 (hep, J=6.4 Hz, 1H), 3.32 (t, J=6.8 Hz, 2H), 3.50 (t, J=6.8 Hz, 2H), 3.54 (s, 3H), 4.05 (d, J=7.6 Hz, 2H), 4.75 (s, 2H), 5.36 (s, 2H), 6.75 (d, J=7.6 Hz, 1H), 7.11-7.55 (m, 8H), 7.83 (d, J=7.6 Hz, 1H), 8.24 (d, J=8.0 Hz, 1H).

Biological Activity

Example 36. Biological Activity of Selected Compounds of the Invention

Specific Examples of compounds of the invention, with estimated EC$_{50}$ values determined using an MTT assay for 4-day viability of Raji (Burkitt's) lymphoma cells, a cell line known to highly express MCT1 and to be sensitive to small molecule MCT inhibitors,[4] are shown in Table 3. Assay protocols follow those described in the literature.[4] Other assays that are not described here but that are standard in the field, such as an assay for competitive inhibition of transport of radiolabeled lactic acid, an MCT substrate, may also be useful in establishing mechanism of action of these compounds.

TABLE 3

| Example | approximate potency (EC$_{50}$ nM) |
|---|---|
| 2 | <50 |
| 3 | <50 |
| 4 | <50 |
| 5 | <50 |
| 6 | <50 |
| 7 | <50 |
| 8 | 300 |
| 9 | <50 |
| 10 | <50 |
| 11 | <50 |
| 12 | <50 |
| 13 | <50 |
| 14 | ≤100 |
| 15 | ≤100 |
| 16 | ≤100 |
| 17 | ≤100 |
| 18 | ≤100 |
| 19 | ≤250 |
| 20 | ≤250 |
| 21 | ≤250 |
| 22 | ≤250 |
| 23 | ≤250 |
| 24 | ≤250 |
| 25 | ≤250 |
| 26 | ≤500 |
| 27 | ≤500 |
| 28 | ≤1000 |
| 29 | ≤1000 |
| 30 | ≤1000 |
| 31 | ≤1000 |
| 32 | ≤1000 |
| 33 | ≤100 |
| 34 | ≥2000 |
| 35 | ≤100 |

Example 37. Mouse Xenograft Studies

The in vivo effects of a few selected agents have been evaluated in mouse xenograft models and found to be effective. Protocols follow those described in the literature.[4]

Mice were transplanted with cultured tumor cells and after an incubation period (typically 8-12 days), mice were left untreated or were treated daily with a 30 mg/kg dose of the test compound. Tumor volumes were measured with calipers over ~20 days of treatment. Tumors were excised and weighed at the end of treatment. In some experiments the mice were co-treated daily with a 30 mg/kg dose of the test compound and 5 mg/kg of metformin.

Figure 3:
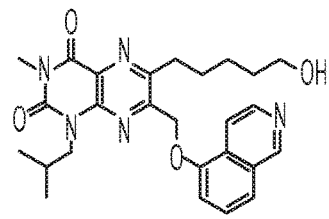
FIG. 3 shows tumor volume results from a mouse tumor xenograft study
Figure 4:
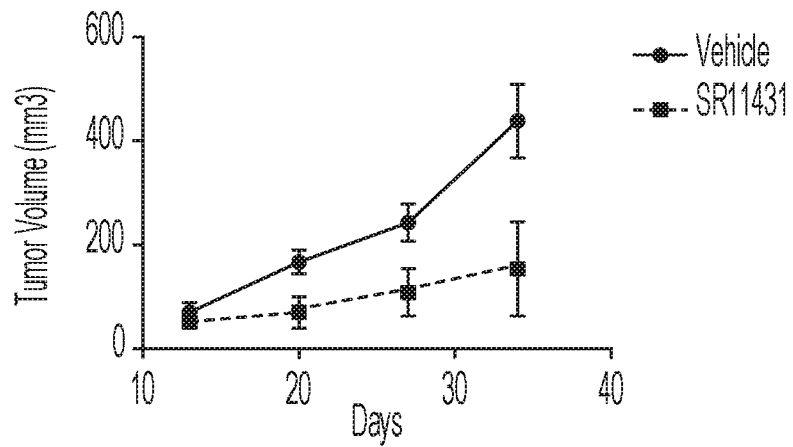
FIG. 4 shows final tumor weight results from a mouse tumor xenograft study.
Figure 5:
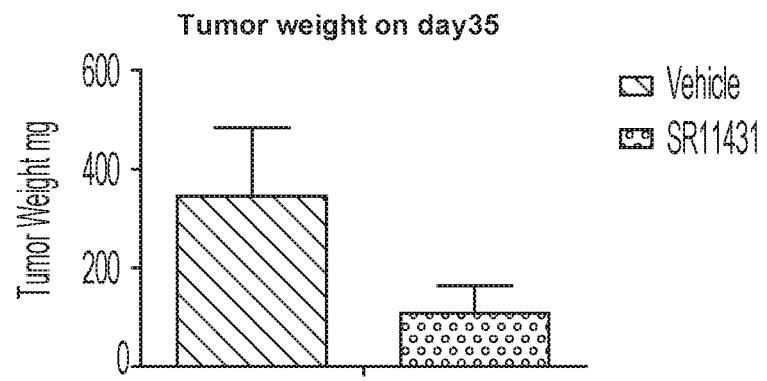
FIG. 5 shows the structure of SR-11431, the product of Example 3, used in the mouse tumor xenograft study referred to in FIGS. 3 and 4.

In a xenograft experiment using T47D tumor cells, and estrogen receptor-positive breast cancer cell line that also selectively express MCT1[4], and test compound SR-11431 (the product of Example 3, FIG. 3) there was a significant reduction of tumor volume (FIG. 4). A corresponding reduction in final tumor mass (FIG. 5) was also observed versus vehicle treated transplanted animals.

Figure 6:
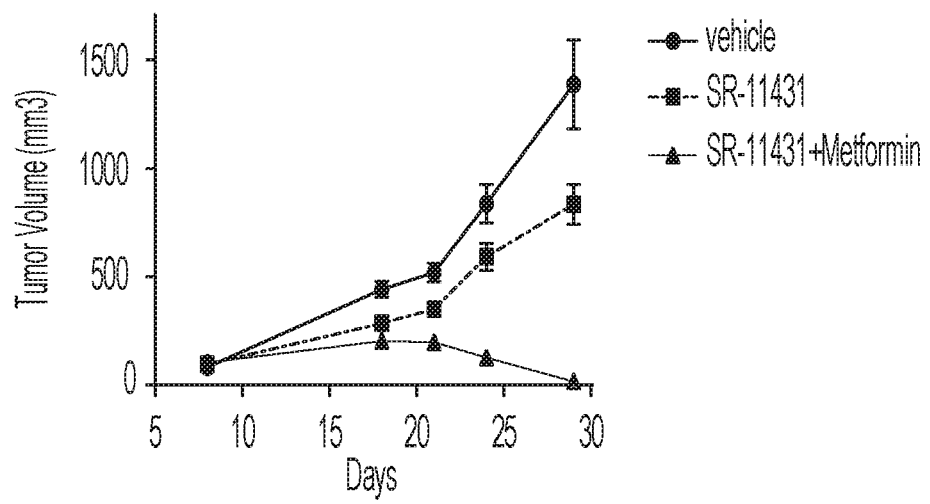
FIG. 6 shows a graph of a time course study of tumor volume for mice to whom was administered SR-11431 and SR-11431 plus Metformin, versus vehicle.
Figure 7:
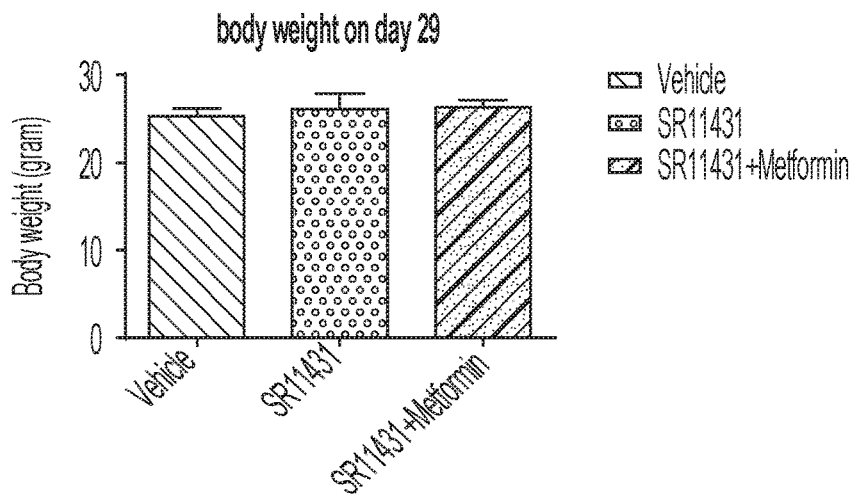
FIG. 7 shows a comparison of test animal body weights from the study of FIG. 6 at day 29.
Figure 8:
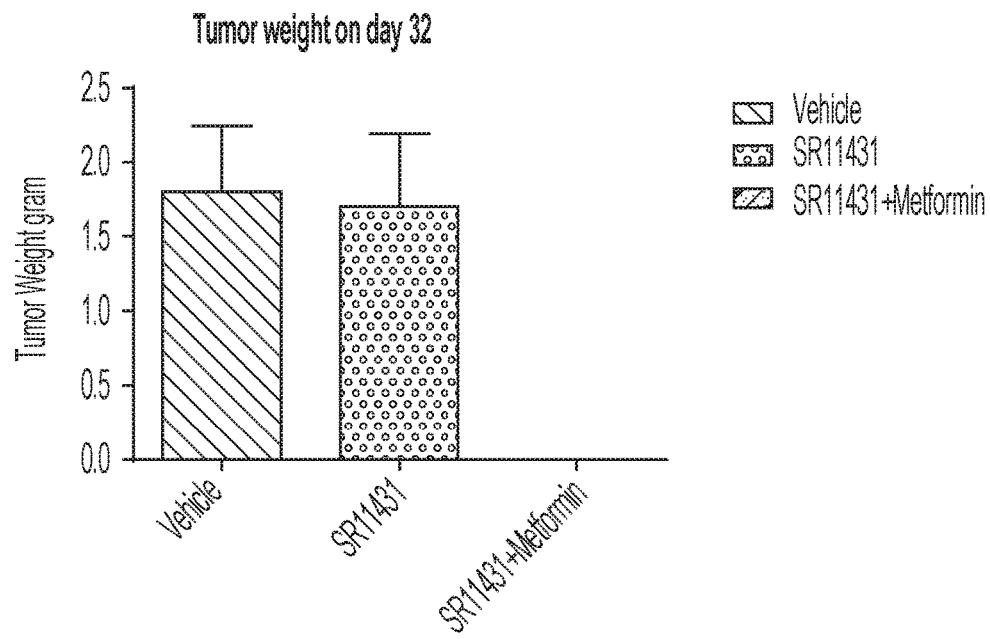
FIG. 8 shows a comparison of tumor weight from the study of FIG. 6 at day 32.

In a separate experiment, this same compound was used in a study using implanted tumors derived from Raji Burkitt lymphoma cells, implanted into nude mice and treated as before with vehicle, with SR-11431, or with SR-11431 plus metformin. Reduction of tumor volume over time (FIG. 6) was observed for both SR-11431-treated and (SR-11431+metformin)-treated animals. The (SR-11431+metformin)-treated cohort of animals showed a profound regression of tumor volume over the 30-day time course (triangles, FIG. 6). These animals exhibited no significant changes in body weight over the treatment period (FIG. 7). Final tumor weight in was not significantly changed in SR-11431-treated animals, but the (SR-11431+metformin)-treated animals lacked any detectable tumors at the end of the treatment period (FIG. 8).

DOCUMENTS CITED

1. Warburg, O. On the origin of cancer cells. *Science* 1956, 123, 309-314.
2. Koppenol, W. H.; Bounds, P. L.; Dang, C. V. Otto Warburg's contributions to current concepts of cancer metabolism. *Nature Rev. Cancer* 2011, 11, 325-327.
3. Halestrap, A. P. The SLC16 gene family—structure, role and regulation in health and disease. *Mol. Asp. Med.* 2013, 34, 337-349.
4. Doherty, J. R.; Yang, C.; Scott, K.; Cameron M. D.; Fallahi, M.; Li, W; Hall, M. A.; Amelio, A. L.; Mishra, J. K.; Li, F; Tortosa, M.; Genau, H. M.; Rounbehler, R. J.; Yungi, L.; Dang, C. V.; Kumar, K. G.; Butler, A. A.; Bannister, T. D.; Hooper, A. T.; Unsal-Kacmaz, K.; Roush, W. R.; and Cleveland, J. L. Blocking lactate export by inhibiting the myc target MCT1 disables glycolysis and glutathione synthesis. *Cancer Res.* 2014, 74, 908-920.
5. Ullah, M. S.; Davies, A. J.; Halestrap, A. P. The plasma membrane lactate transporter MCT4, but not MCT1, is up-regulated by hypoxia through a HIF-1α-dependent mechanism. *J. Biol. Chem.* 2006, 281, 9030-9037.
6. Dang, C. V. The interplay between MYC and HIF in the Warburg effect. *Ernst Schering Found Symp. Proc.* 2007, 35-53.
7. Vaupel, P.; Mayer, A. Hypoxia in cancer: significance and impact on clinical outcome. *Cancer Metastasis Rev.* 2007, 26, 225-239.
8. Kizaka-Kondoh, S.; Inoue, M.; Harada, H.; Hiraoka, M. Tumor hypoxia: a target for selective cancer therapy. *Cancer Sci.* 2003, 94, 1021-1028.
9. Le Floch, R.; Chiche, J.; Marchiq, I.; Naiken, T.; Ilk, K.; Murray, C. M.; Critchlow, S. E.; Roux, D.; Simon, M. P.; Pouyssegur, J. CD147 subunit of lactate/$H^+$ symporters MCT1 and hypoxia-inducible MCT4 is critical for energetics and growth of glycolytic tumors. *Proc. Natl. Acad. Sci. USA* 2011, 108, 16663-16668.
10. Sonveaux, P.; Vegran, F.; Schroeder, T.; Wergin, M. C.; Verrax, J.; Rabbani, Z. N.; De Saedeleer, C.; J.; Kennedy, K. M.; Diepart, C.; Jordan, B. F.; Kelley, M. J.; Gallez, B.; Wahl, M. L.; Feron, O.; Dewhirst, M. W. Targeting lactate-fueled respiration selectively kills hypoxic tumor cells in mice. *J. Clin Invest.* 2008, 118, 3930-3942.
11. Broer, S.; Schneider, H.; Broer, A.; Rahman, B.; Hamprecht, B.; Deitmer, J. W. Characterization of the monocarboxylate transporter 1 expressed in *Xenopus laevis* oocytes by changes in cytosolic pH. *Biochem. J.* 1998, 333, 167-174.
12. Jackson, V, N.; Halestrap, A. P. The kinetics, substrate, and inhibitor specificity of the monocarboxylate (lactate) transporter of rat liver cells determined using the fluorescent intracellular pH indicator, 2',7'-bis(carboxyethyl)-5 (6)-carboxyfluorescein. *J. Biological Chem.* 1996, 271, 861-868.
13. Kobayashi, M.; Itagaki, S.; Hirano, T.; Iseki, K. mechanism of L-lactic acid transport in L6 skeletal muscle cells. *Drug Metab. Pharmacokin.* 2004, 19, 363-368.
14. Wang, Q.; Morris, M. E. Flavonoids modulate monocarboxylate transporter-1-mediated transport of γ-hydroxybutyrate in vitro and in vivo. *Drug Metabolism and Disposition* 2007, 35, 201-208.
15. Draoui, N.; Schicke, O.; Fernandes A.; Drozak, X.; Fady, N.; Dumont, A.; Douxfils, J.; Hermans, E.; Dogné, J-M.; Corbau, R.; Marchand, A.; Chaltin, P.; Sonveaux, P.; Feron, O.; Riant, O. Synthesis and pharmacological evaluation of carboxycoumarins as a new antitumor treatment targeting lactate transport in cancer cells. *Bioorg. Med. Chem.* 2013, 21, 7107-7117.
16. Mereddy, V. R.; Drewes, L. R.; Alam, M. A.; Jonnalagadda, S. K.; Gurrapu, S. Preparation of benzopyran derivatives and related compounds as MCT1 inhibitors. PCT Int. Appl. 2013, WO2013109972 A2 20130725.
17. Wang, H, and Bannister, T. D.; Synthesis and Structure-Activity Relationships of Pteridine Diane and Trione Monocarboxylate Transporter 1 Inhibitors, *J. Med. Chem.*, 2014, 57 (17), 7317-7324
18. Murray, C. M.; Hutchinson, R.; Bantick, J. R.; Belfield, G. P.; Benjamin, A. D.; Brazma, D.; Bundick, R. V.; Cook, I. D.; Craggs, R. I.; Edwards, S.; Evans, L. R.; Harrison, R.; Holness, E.; Jackson, A. P.; Jackson, C. G.; Kingston, L. P.; Perry, M. W. D.; Ross, A. R. J.; Rugman, P. A.; Sidhu, S. S.; Sullivan, M.; Taylor-Fishwick, D. A.; Walker, P. C.; Whitehead, Y. M.; Wilkinson, D. J.; Wright, A.; Donald, D. Monocarboxylate transporter MCT1 is a target for immunosuppression. *Nat. Chem. Biol.* 2005, 1, 371-376.
19. Guile, S. D.; Bantick, J. R.; Cheshire, D. R.; Cooper, M. E.; Davis, A. M.; Donald, D. K.; Evans, R.; Eyssade, C.; Ferguson, D. D.; Hill, S.; Hutchinson, R.; Ingall, A. H.; Kingston, L. P.; Marin, I.; Martin, B. P.; Mohammed, R. T.; Murry, C.; Perry, M. W. D.; Reynolds, R. H.; Thorne, P. V.; Wilkinson, D. J.; Withnall, J. Potent blockers of the monocarboxylate transporter MCT1: novel immunomodulatory compounds. *Bioorg. Med. Chem. Lett.* 2006, 16, 2260-2265.
20. Guile, S. D.; Bantick, J. R.; Cooper, M. E.; Donald, D. K.; Eyssade, C.; Ingall, A. H.; Lewis, R. J.; Martin, B. P.; Mohammed, R. T.; Potter, T. J.; Reynolds, R. H.; St-Gallay, S. A.; Wright, A. D. Optimization of monocarboxylate transporter 1 blockers through analysis and modulation of atropisomer interconversion properties. *J. Med. Chem.* 2007, 50, 254-263.
21. Bueno, V.; Binet, I.; Steger, U.; Bundick, R.; Ferguson, D.; Murray, C.; Donald, D.; Wood, K. The specific monocarboxylate transporter (MCT1) inhibitor, AR-C117977, a novel immunosuppressant, prolongs allograft survival in the mouse. *Transplantation* 2007, 84, 1204-1207.
22. Ovens, M. J.; Davies, A. J.; Wilson, M. C.; Murray, C. M.; Halestrap, A. P. AR-C155858 is a potent inhibitor of monocarboxylate transporters MCT1 and MCT2 that binds to an intracellular site involving transmembrane helices 7-10. *Biochem. J.* 2010, 425, 523-530.
23. Critchlow, S, E.; Tate, L. Use of a MCT1 inhibitor in the treatment of cancers expressing MCT1 over MCT4. PCT Int. Appl. 2010, WO2010089580 A1 20100812.
24. http://clinicaltrials.gov/show/NCT01791595
25. Polanski, R.; Hodgkinson, C. L.; Fusi, A.; Nonaka, D.; Priest, L.; Kelly, P.; Trapani, F.; Bishop, P. W.; White, A.; Critchlow, S. E.; Smith, P. D.; Blackhall F.; Dive, C.; Morrow, C. J. Activity of the monocarboxylate transporter 1 inhibitor AZD3965 in small cell lung cancer. *Clin. Cancer Res.* 2014, 20, 926-937.
26. Michne, W. F.; Schroeder, J. D.; Guiles, J. W.; Treasurywala, A. M.; Weigelt, C. A.; Stansberry, M. F.; McAvoy, E.; Shah, C. R.; Bump, E.; Schlegel, D. Novel Inhibitors of the Nuclear Factor of Activated T Cells (NFAT)-Mediated Transcription of .beta.-Galactosidase: Potential Immunosuppressive and Antiinflammatory Agents. *J. Med. Chem.*, 1995, 38 (14), 2557-2569.

27. Otonkoski, T; Jiao, H; Kaminen-Ahola, N; et al. Physical exercise-induced hypoglycemia caused by failed silencing of monocarboxylate transporter 1 in pancreatic beta cells. *Am J Hum Genet* 2007; 81, 467-474.
28. Zhao, C.; Wilson, M. C.; Schuit, F.; Halestrap, A. P.; Rutter, G. A. Expression and distribution of lactate/monocarboxylate transporter isoforms in pancreatic islets and the exocrine pancreas. *Diabetes* 2001; 50, 361-366.
29. Sekine, N.; Cirulli, V.; Regazzi, R.; et al. Low lactate dehydrogenase and high mitochondrial glycerol phosphate dehydrogenase in pancreatic beta-cells. Potential role in nutrient sensing. *J Biol Chem* 1994, 269, 4895-4902.
30. Otonkoski, T.; Kaminen, N.; Ustinov, J.; et al. Physical exercise-induced hyperinsulinemic hypoglycemia is an autosomal-dominant trait characterized by abnormal pyruvate-induced insulin release. *Diabetes* 2003; 52, 199-204.
31. Pullen T. J.; Sylow, L.; Sun, G.; Halestrap, A. P.; Richter, E. A.; Rutter, G. A. Overexpression of Monocarboxylate Transporter-1 (Slc16a1) in Mouse Pancreatic beta-Cells Leads to Relative Hyperinsulinism During Exercise. *Diabetes* 2012, 61, 1719-1725.
32. Best, L.; Yates, A. P.; Meats, J. E.; Tomlinson, S. Effects of lactate on pancreatic islets: Lactate efflux as a possible determinant of islet-cell depolarization by glucose. *Biochem. J.* 1989; 259, 507-511.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:
1. A MCT-inhibitory compound of formula A or of formula B

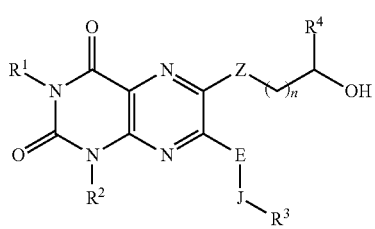

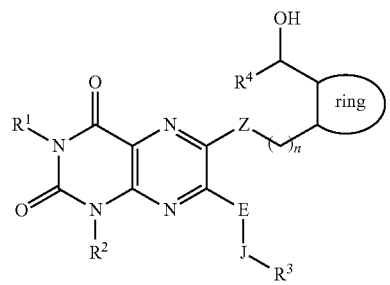

wherein
$R^1$ and $R^2$ are each independently selected from the group consisting of hydrogen, $(C_1-C_6)$alkyl, $(C_3-C_6)$ branched alkyl, $(C_3-C_7)$cycloalkyl, $(C_1-C_6)$fluoroalkyl, a $(C_6-C_{10})$aryl ring system, a 5- to 9-membered heteroaryl ring system, a $(C_1-C_6)$alkyl-$(C_6-C_{10})$aryl ring system, and a $(C_1-C_6)$alkyl-(5- to 9-membered)heteroaryl ring system;
provided that when $R^2$ comprises an aryl or heteroaryl ring system, the ring system bears 0-2 independently selected substituents from the group consisting of fluoro, chloro, trifluoromethyl, $(C_1-C_6)$alkoxy, and $(C_1-C_6)$fluoroalkoxy;
E is $CH_2$, $CH(C_1-C_6)$alkyl, or $CH(C_3-C_7)$cycloalkyl;
J is O, S, S(O), $S(O)_2$, NH, $N(C_1-C_6)$alkyl, or NC(=O)$(C_1-C_6)$alkyl;
$R^3$ is a monocyclic or bicyclic $(C_6-C_{10})$aryl or a monocyclic or bicyclic (5- to 10-membered) heteroaryl group wherein the aryl or heteroaryl can be substituted or unsubstituted;
$R^4$ is hydrogen, $(C_1-C_6)$alkyl, $(C_3-C_6)$branched alkyl, $(C_1-C_6)$fluoroalkyl, $(C_3-C_7)$cycloalkyl, a (4- to 7-membered)heteroaryl, or a monocyclic or bicyclic $(C_6-C_{10})$aryl or a monocyclic or bicyclic (5- to 10-membered) heteroaryl group wherein the aryl or heteroaryl can be substituted or unsubstituted;
Z is a bond, or is —O—, —$CH_2$—, —CH(Me)-, —S—, —NH—, or —$N(C_1-C_6)$alkyl;
n=1, 2, 3, or 4;
the cyclic group indicated as "ring" is an aryl or heteroaryl group of any one of the following formulas:

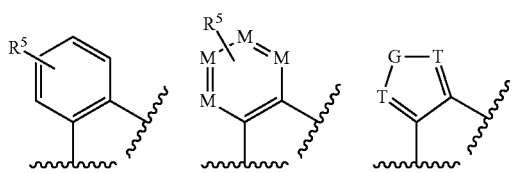

wherein wavy lines indicate points of bonding, and wherein each M is an independently selected CH or N, provided that M group is a nitrogen atom in one or two instances;
G is S, O, NH, NMe, or $NCF_3$;
T is independently at each occurrence CH or N;
wherein $R^5$ is optionally present, $R^5$ being one to four instances of independently selected F, Cl, Br, $CF_3$, $(C_1-C_6)$alkyl, $OCF_3$, $O(C_1-C_6)$alkyl, or CO—$(C_1-C_6)$alkyl;

or,
the cyclic group indicated as "ring" is a ($C_3$-$C_7$)cycloalkyl or a saturated (3- to 7-membered)heterocyclyl comprising 1-2 heteroatoms selected from the group consisting of O, NH, N(C1-C6)alkyl, and N(C1-C6)fluoroalkyl; wherein the points of bonding may be cis or trans;
or a pharmaceutically acceptable salt thereof.

2. The compound of claim 1, wherein a monocyclic $R^3$ is any one of

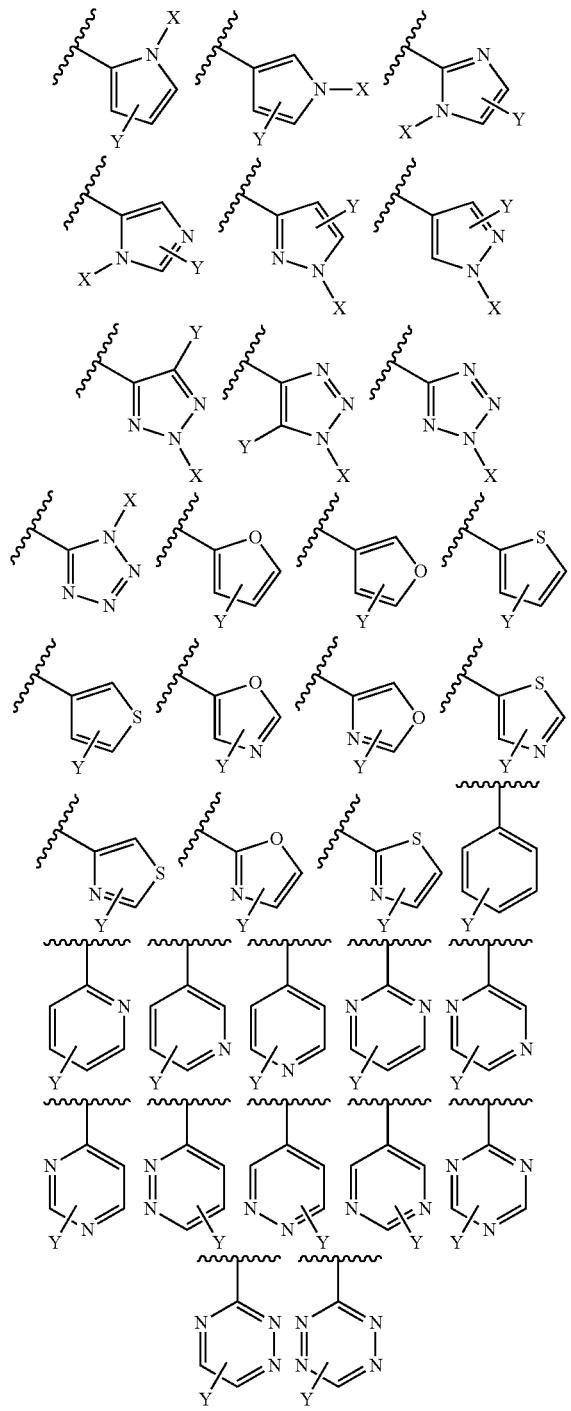

wherein X is H, ($C_1$-$C_6$)alkyl, or $CF_3$; and wherein Y is optionally present and, when present, Y is 1-3 instances of a substituent selected from the group consisting of F, Cl, Br, $CF_3$, $CH_3$, Et, $NH_2$, NH—$(CH_2)_j$—$CH_2$-Q, and

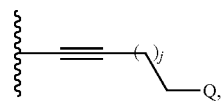

wherein j=2-6, and wherein Q is one of the following groups

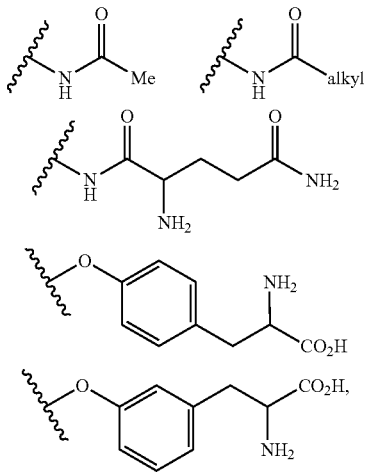

wherein a wavy line indicates a point of bonding.

3. The compound of claim 1, wherein a bicyclic $R^3$ is any one of

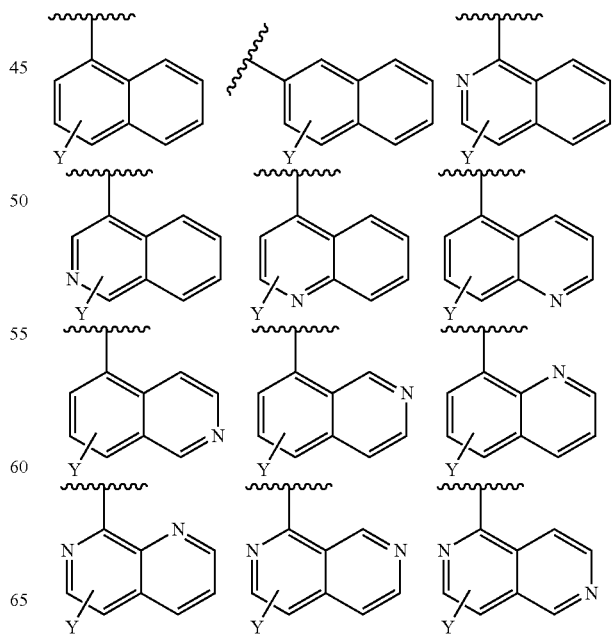

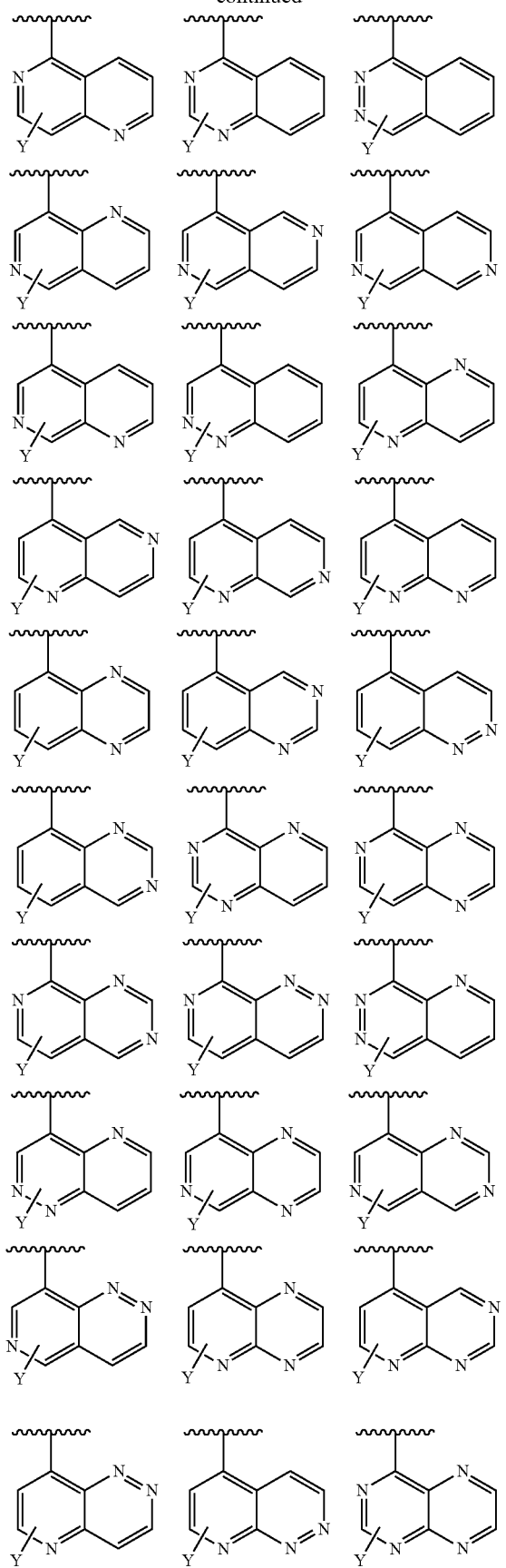
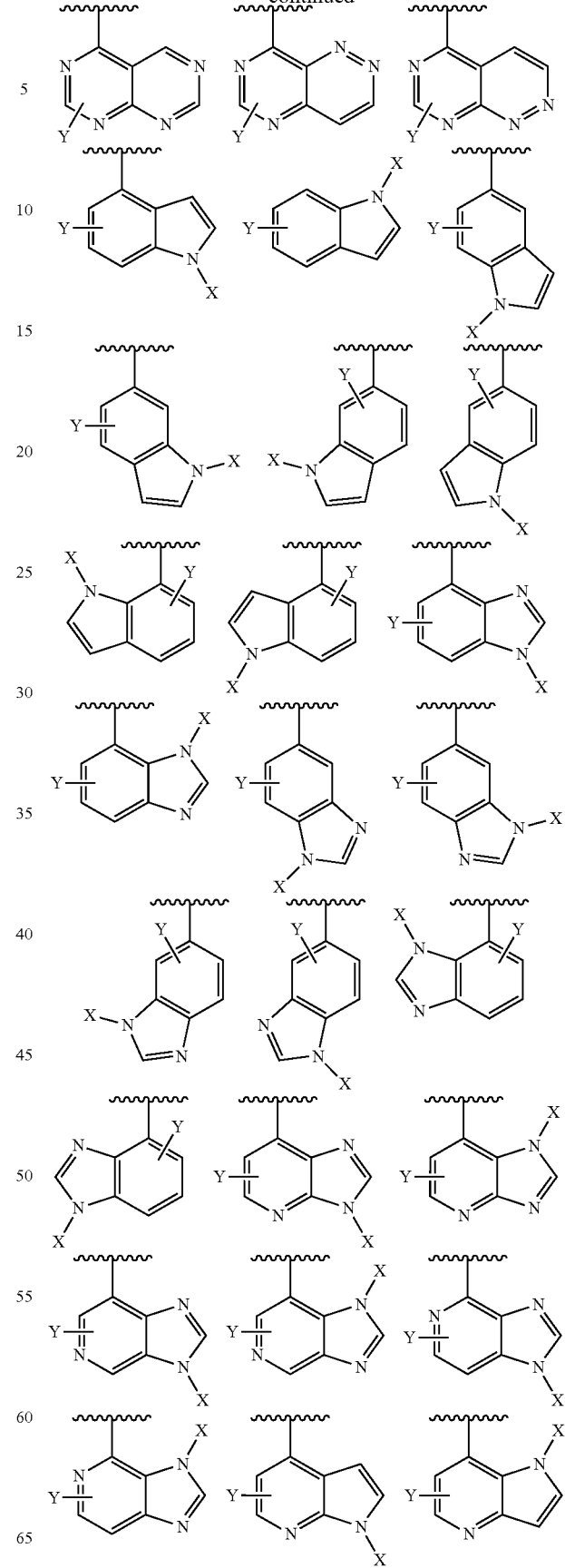

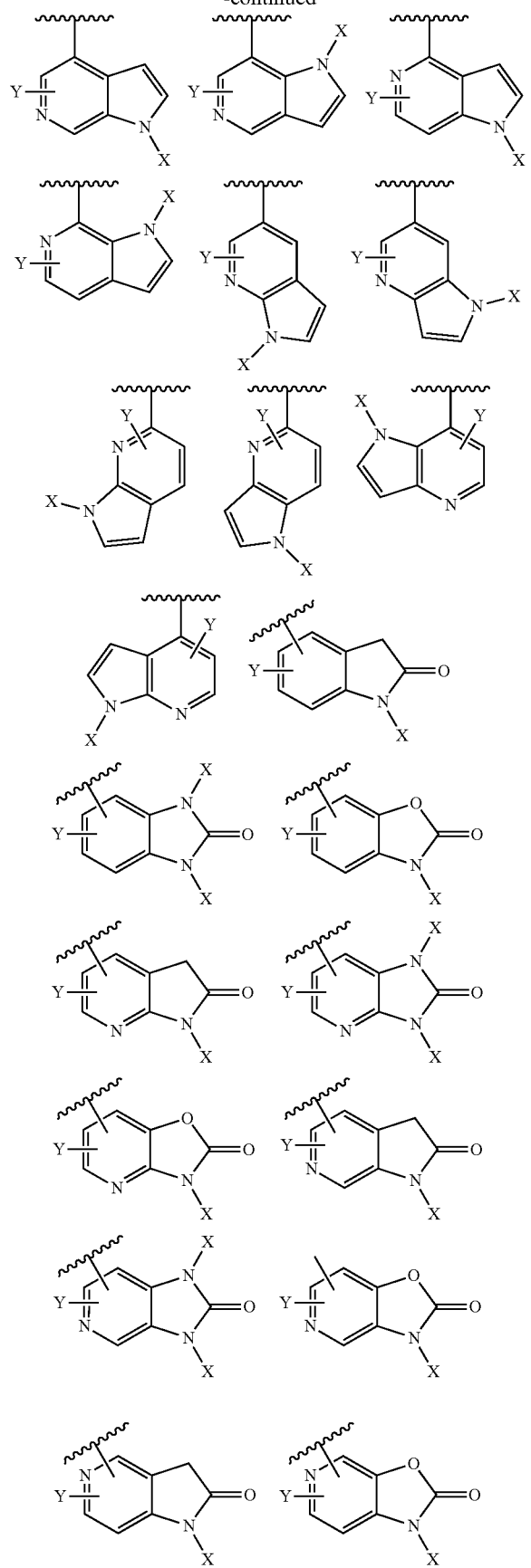
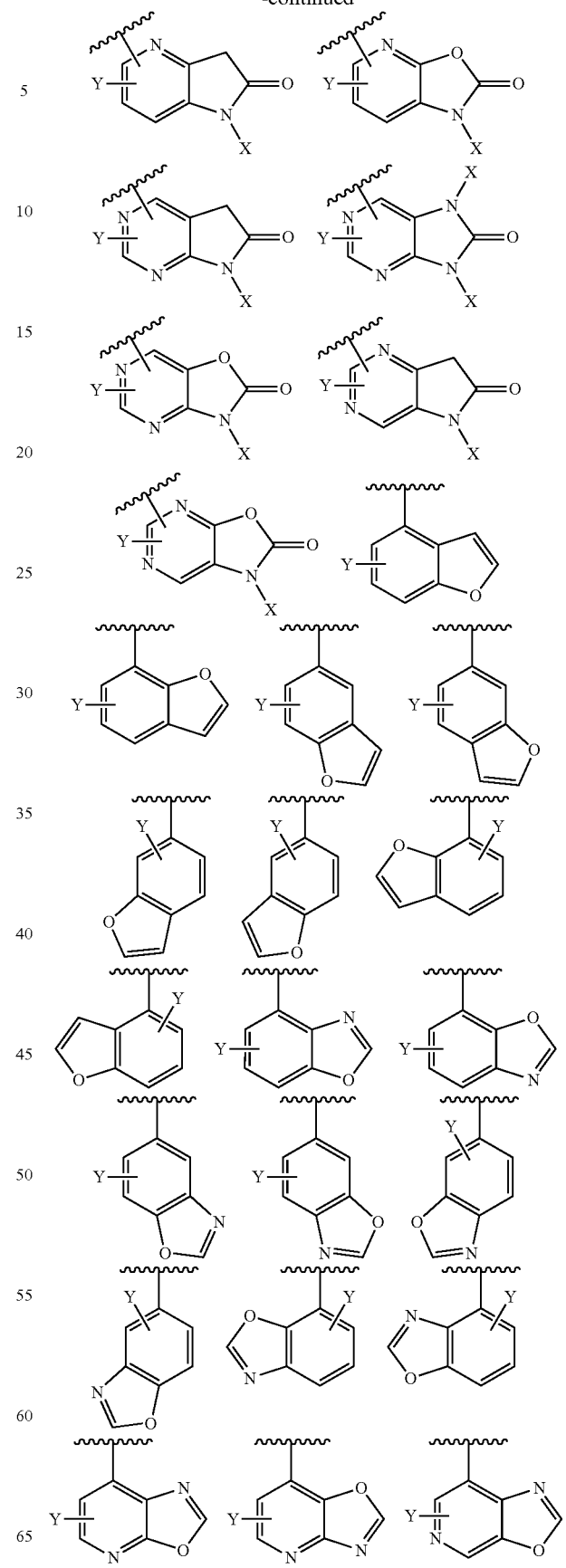

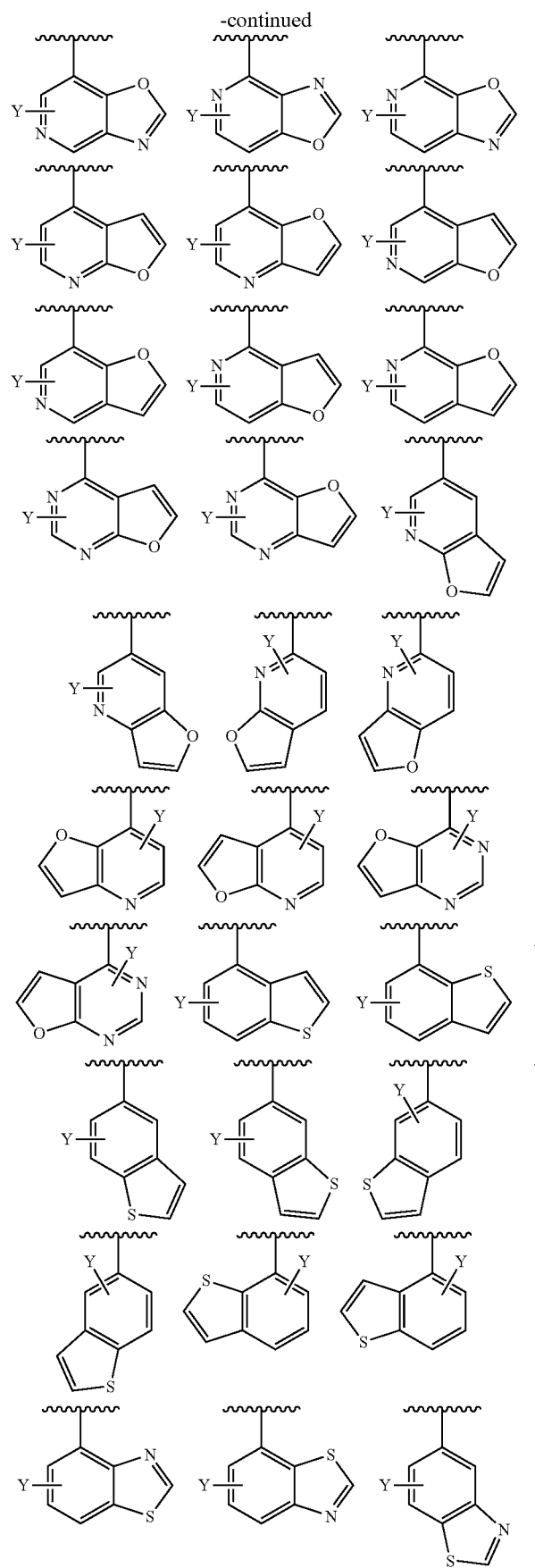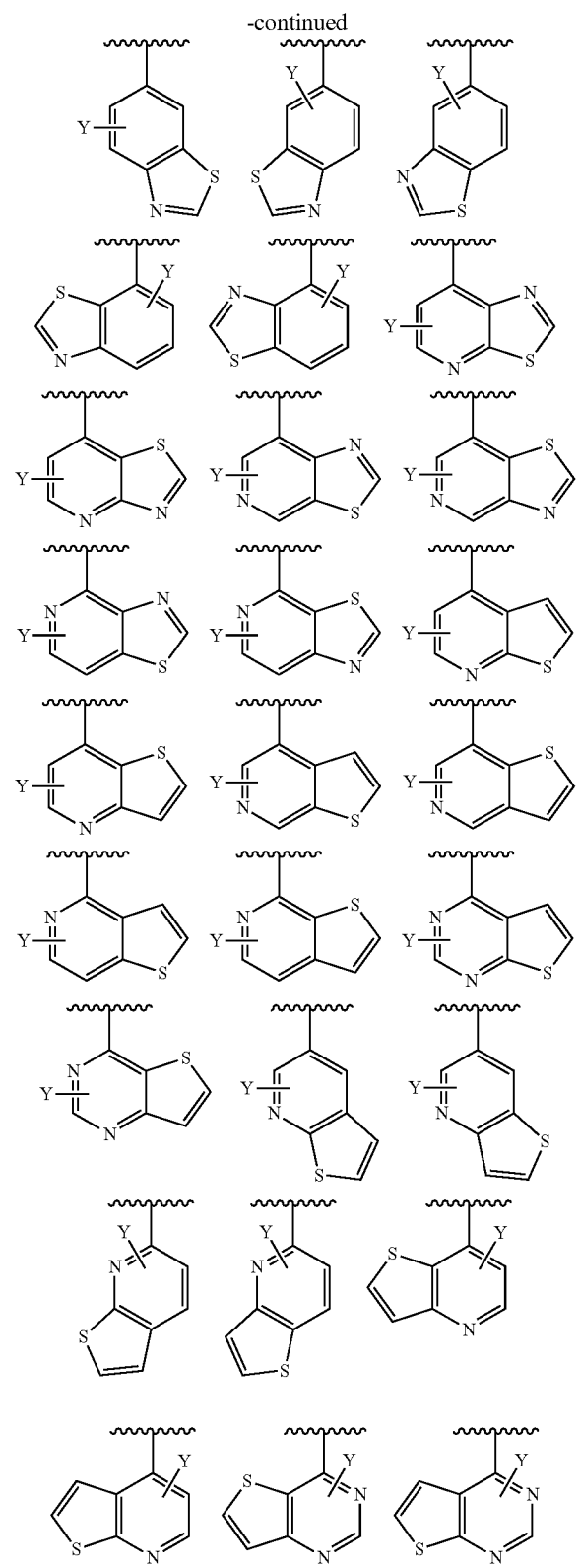
wherein X is H, $(C_1-C_6)$alkyl, or $CF_3$; and
wherein Y is optionally present and, when present, Y is 1-3 instances of a substituent selected from the group consisting of F, Cl, Br, $CF_3$, $CH_3$, Et, $NH_2$, NH—$(CH_2)_j$—$CH_2$-Q, and

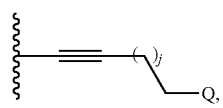

wherein j=2-6, and wherein Q is one of the following groups

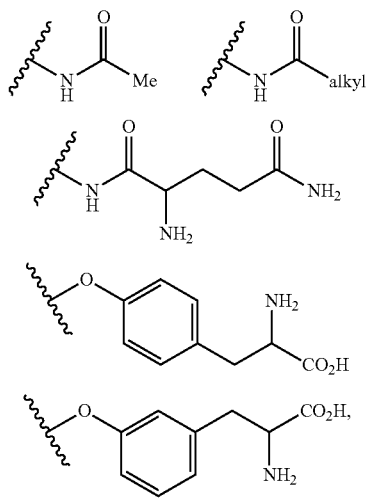

wherein a wavy line indicates a point of bonding, and wherein Y can be disposed on any ring of a multi-ring system.

4. The compound of claim 1, wherein $R^1$=Me, $R^2$=i-Bu, $R^4$=H, Z=$CH_2$, and other groups are as specified in claim 1.

5. The compound of claim 1 of formula A wherein n=3.

6. The compound of claim 1, wherein the compound is any one of the following, including all stereoisomeric forms, all isotopic forms, all crystalline and amorphous forms, and all pharmaceutically acceptable salt forms thereof:

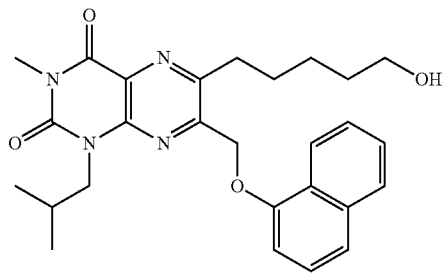

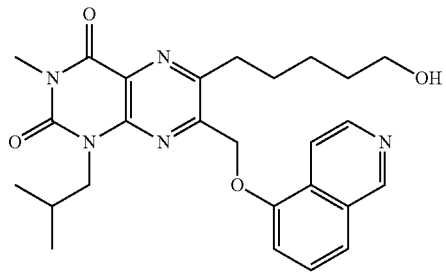

-continued

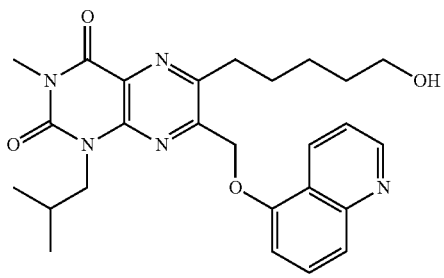

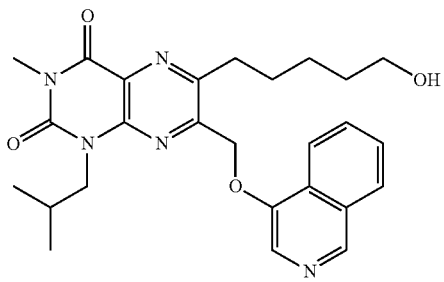

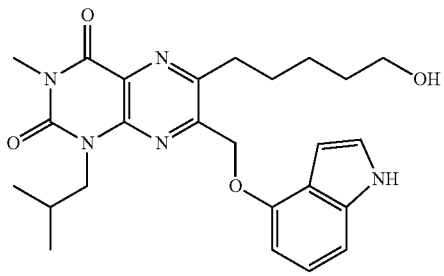

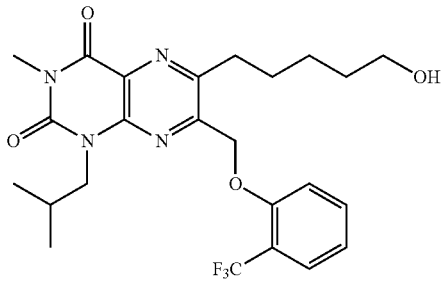

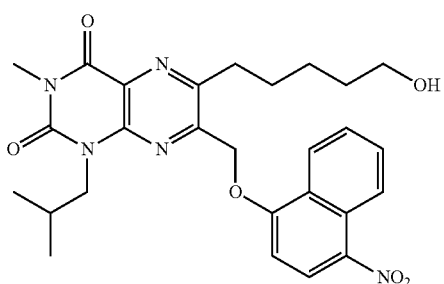

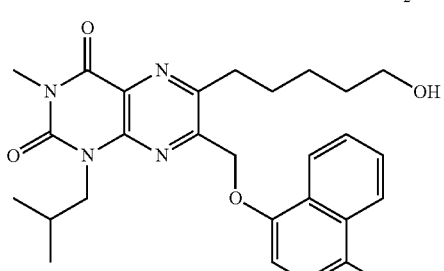

91
-continued
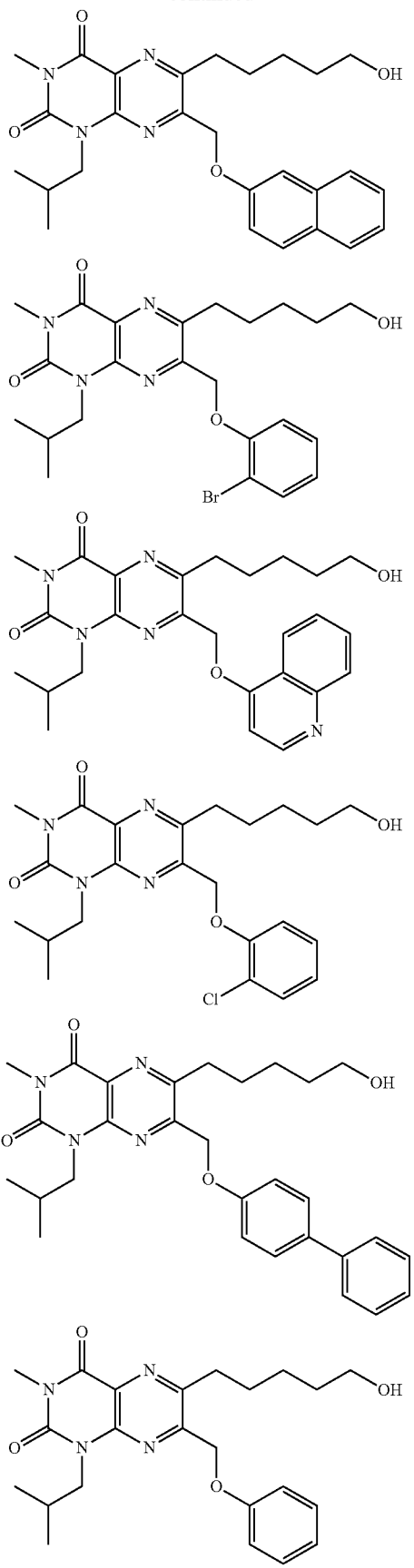
92
-continued
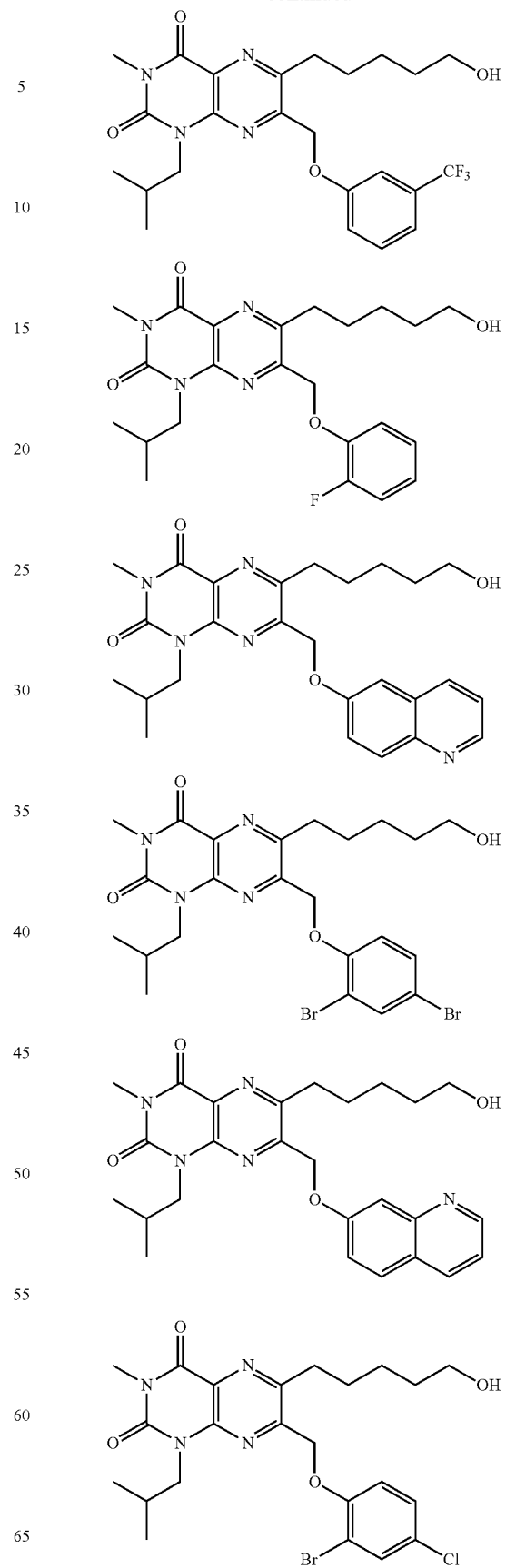

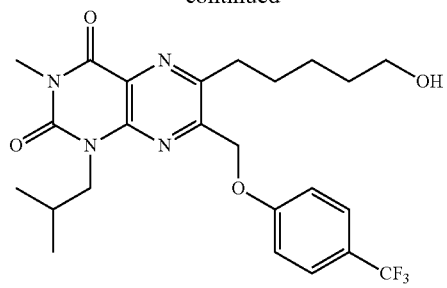
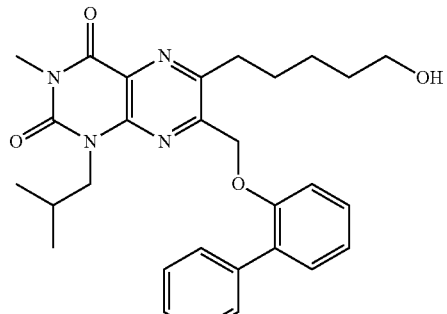
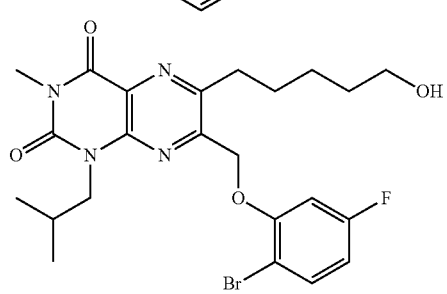
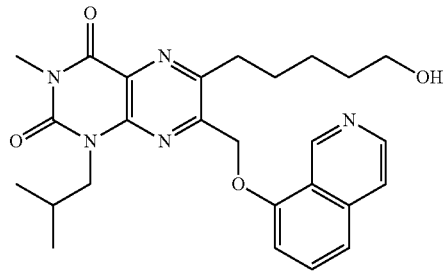
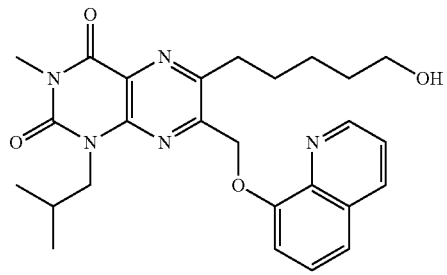
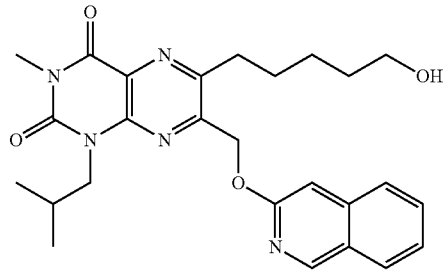
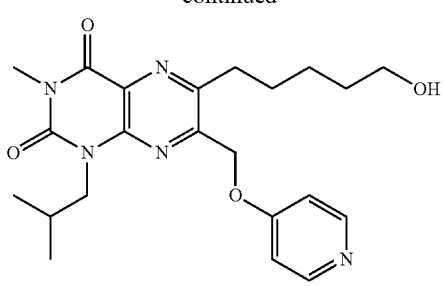
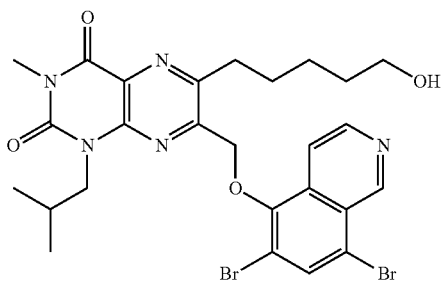
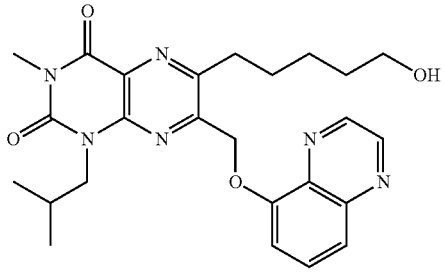
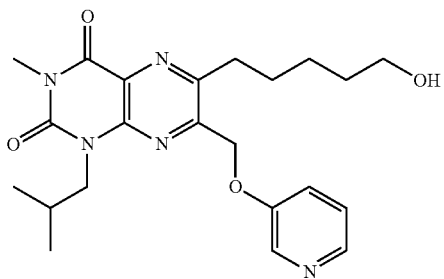
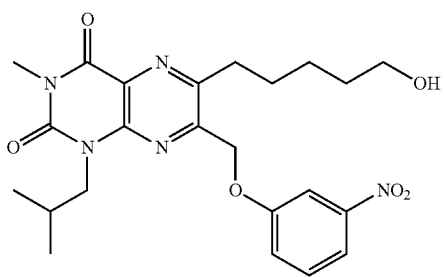
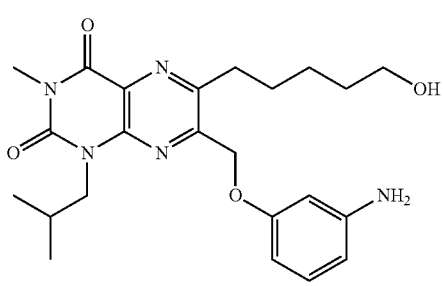

-continued
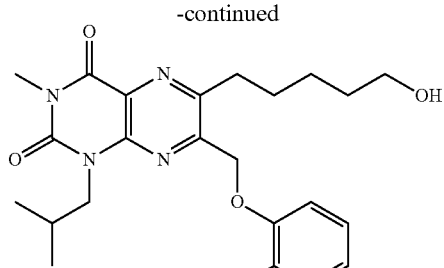
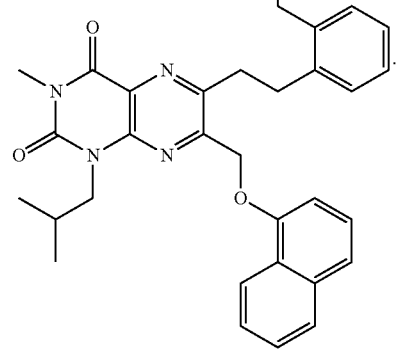
7. A pharmaceutical composition comprising a compound of claim 1 and a pharmaceutically acceptable excipient.
* * * * *